United States Patent
Palpant et al.

(10) Patent No.: US 12,173,322 B2
(45) Date of Patent: Dec. 24, 2024

(54) GENOME-EDITED INDUCED PLURIPOTENT STEM CELLS, AND CELLS DERIVED THEREFROM, AND USES THEREOF

(71) Applicant: The University of Queensland, St. Lucia (AU)

(72) Inventors: Nathan Palpant, St. Lucia (AU); Meredith Ann Redd, St. Lucia (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 566 days.

(21) Appl. No.: 17/116,332

(22) Filed: Dec. 9, 2020

(65) Prior Publication Data

US 2022/0177846 A1    Jun. 9, 2022

(51) Int. Cl.
| | | |
|---|---|---|
| C12N 5/077 | (2010.01) | |
| A61K 45/06 | (2006.01) | |
| A61P 9/10 | (2006.01) | |

(52) U.S. Cl.
CPC ............ *C12N 5/0657* (2013.01); *A61K 45/06* (2013.01); *A61P 9/10* (2018.01)

(58) Field of Classification Search
None
See application file for complete search history.

(56) References Cited

U.S. PATENT DOCUMENTS

| | | | |
|---|---|---|---|
| 9,206,393 | B2 | 12/2015 | Kruse |
| 9,663,764 | B2 | 5/2017 | Palecek et al. |
| 9,994,812 | B2 | 6/2018 | Kim et al. |
| 10,155,927 | B2 | 12/2018 | Burcin et al. |
| 2006/0040389 | A1 | 2/2006 | Murry et al. |
| 2008/0089874 | A1 | 4/2008 | Li et al. |
| 2010/0166714 | A1 | 7/2010 | Chien et al. |
| 2017/0058263 | A1 | 3/2017 | Sun et al. |

FOREIGN PATENT DOCUMENTS

| | | | | |
|---|---|---|---|---|
| JP | 5271953 B2 * | 8/2013 | ............. | A61K 38/18 |
| WO | 2019035032 A2 | 2/2019 | | |

OTHER PUBLICATIONS

Wemmie, John A., et al. "The acid-activated ion channel ASIC contributes to synaptic plasticity, learning, and memory." Neuron 34.3 (2002): 463-477. (Year: 2002).*
Scheuer, S. E., et al. "Hi1a, an ASIC1a inhibitor, significantly improves the tolerance of donor allografts to ischaemia in a rodent model of DCD heart transplantation." The Journal of Heart and Lung Transplantation 38.4 (2019): S182. (Year: 2019).*
JP-5271953-B2 machine translated by Google (Year: 2013).*
Redd, Meredith A., et al. "Therapeutic inhibition of acid-sensing ion channel 1a recovers heart function after ischemia-reperfusion injury." Circulation 144.12 (2021): 947-960. (Year: 2021).*
Friedman et al., Single-Cell Transcriptomic Analysis of Cardiac Differentiation from Human PSCs Reveals HOPXDependent Cardiomyocyte Maturation, Cell Stem Cell, 2018, 23, 586-598.
Laflamme et al., Cardiomyocytes derived from human embryonic stem cells in pro-survival factors enhance function of infarcted rat hearts, Nature Biotech, 2007, 25: 1015-1024.
Laflamme et al., Formation of Human Myocardium in the Rat Heart from Human Embryonic Stem Cells, American Journal of Pathology, 2005, vol. 167, No. 3.
Lian et al., Directed cardiomyocyte differentiation from human pluripotent stem cells by modulating Wnt/β-catenin signaling under fully defined conditions, Nat Protoc., 2013, 8(1): 162-175.
Redd etal., Pharmacological inhibition of acid sensing ion channel 1a protects the heart from ischemia-reperfusion injury, bioRxiv preprint doi: https://doi.org/10.1101/869826, Dec. 10, 2019.
Unknown, Characterization by flow cytometry PSC-derived cardiomyocyte subtypes, Miltenyi Biotec MACS®, 2017.
Xu et al., Characterization and Enrichment of Cardiomyocytes Derived From Human Embryonic Stem Cells, Circ Res., 2002, DOI: 10.1161/01.RES.0000035254.80718.91.

* cited by examiner

*Primary Examiner* — Emily A Cordas
*Assistant Examiner* — Constantina E Stavrou
(74) *Attorney, Agent, or Firm* — Nixon & Vanderhye P.C.

(57) ABSTRACT

This invention relates to compositions and uses of genome edited iPSCs and cells derived therefrom. In particular the iPSCs and cells derived therefrom and compositions comprising the same according to the present invention may be used in cell-based therapies for tissue repair or regeneration. The invention relates to the treatment and/or prevention of injury to the myocardium, and/or ischemia reperfusion injury in the myocardium and other vascularized tissues.

6 Claims, 8 Drawing Sheets
Specification includes a Sequence Listing.

SEQUENCE LISTING

```
<160> NUMBER OF SEQ ID NOS: 21

<210> SEQ ID NO 1
<211> LENGTH: 3886
<212> TYPE: DNA
<213> ORGANISM: Homo sapiens

<400> SEQUENCE: 1 cccctcccc tcccgccgcc tcccggccgg acgatggatc cctgcagatc ccagggctga      60
gagcaccgcg caccgcgccg agcccgggca gaccgagccg aggcgagcga gccagcgagc     120
```

-continued

```
cagcgcgcgc gggcgggcgg acagatcgga gccgagcggg gccgggcggg gcgctccctg    180
cagggctctg cgcggcgtgc cgcggcggcc gcgggctccg gccccgggcc atgagcccct    240
ccgcgactcg gcgctgagcc cgccaccggt ccagcgcccc aggacccgcc gccggctgcc    300
ggcttgccga agcccctca ggatcccctc aacaaggatg aactgaagg ccgaggagga    360
ggaggtgggt ggcgtccagc cggtgagcat ccaggccttc gccagcagct ccacactgca    420
cggcctggcc cacatcttct cctacgagcg gctgtctctg aagcgggcac tgtgggccct    480
gtgcttcctg ggctccctgg ctgtgctgct gtgtgtgtgc acggagcgtg tgcagtacta    540
cttccactac caccatgtca ccaagctcga cgaggtggct gcctctcagc ttaccttccc    600
tgctgtcacg ctgtgcaacc tcaacgagtt ccgctttagc caagtctcca agaatgacct    660
gtatcatgct ggggagctgc tggccctgct caacaacagg tatgagatac agacacaca    720
gatggcagat gaaaagcagc tggagatact gcaggacaaa gccaacttcc gcagcttcaa    780
acccaaaccc ttcaacatgc gtgagttcta cgaccgagct gggcacgaca ttcgagacat    840
gctgctctcc tgccacttcc gggggaggt ctgcagcgcg gaagacttca aggtggtctt    900
cacacgctat ggaaagtgct acacgttcaa ctcgggccga gatgggcggc gcggctgaa    960
gaccatgaag ggtgggacgg gcaatgggct ggaaatcatg ctggacatcc agcaggacga   1020
gtacctgcct gtgtggggg agactgacga cgtccttc gaagcaggca tcaaagtgca   1080
gatccatagt caggatgaac ctccttcat cgaccagctg gctttggcg tggccccagg   1140
cttccagacc tttgtggcct gccaggagca gcggctcatc tacctgcccc caccctgggg   1200
cacctgcaaa gctgttacca tggactcgga tttggatttc ttcgactcct acagcatcac   1260
tgcctgccgc atcgactgtg agacgcgcta cctggtggag aactgcaact gccgcatggt   1320
gcacatgcca ggggatgccc catactgtac tccagagcag tacaaggagt gtgcagatcc   1380
tgctctggac ttcctggtgg agaaggacca ggagtactgc gtgtgtgaaa tgccttgcaa   1440
cctgacccgc tatggcaaag agctgtccat ggtcaagatc cccagcaaag cctcagccaa   1500
gtacctggcc aagaagttca acaaatctga gcaatacata ggggagaaca tcctggtgct   1560
ggacattttc tttgaagtcc tcaactatga gaccattgaa cagaagaagg cctatgagat   1620
tgcagggctc ctgggtgaca tcgggggcca gatgggggctg ttcatcgggg ccagcatcct   1680
cacggtgctg gagctctttg actacgccta cgaggtcatt aagcacaagc tgtgccgacg   1740
aggaaaatgc cagaaggagg ccaaaaggag cagtgcggac aagggcgtgg ccctcagcct   1800
ggacgacgtc aaaagacaca acccgtgcga gagccttcgg ggccaccctg ccgggatgac   1860
atacgctgcc aacatcctac ctcaccatcc ggcccgaggc acgttcgagg actttacctg   1920
ctgagccccg caggccgctg aaccaaaggc ctagatgggg aggactagga gagcgagggg   1980
gcccccagct gcctcctcac atctgccctg gggactcccc acactccggg gcagatcttt   2040
cctcttgtct gtggtaagga aggagtcttg accatagagt cctctctctg cctctatccc   2100
attctttta catttaacaa aactaatcta aaaaagaact aaaaagggag aacgggcaa   2160
gggacctcag gctgcccctc tctcctccat gctgcctccc ctagctccca gcctgaattc   2220
tgtctatcta gctgtctgcc atctgagtgt ccatctacat tctgctgcca ccagtcacca   2280
aaggcccttc ccagtgaggg gtggaaggga tctctggggt ctggaatttg gccccaaacc   2340
agagaatgta ccttaagggg gagggctagt gtgggggagg gaggcttccc cagccttaag   2400
agaccctctc agcccagtga ctgtcccaa acccaagtct cctggcagga actaaaacct   2460
cagccccact ctctcacacc atgtggaatc tcgtgggggt cggggatccc cttaagaagt   2520
```

```
ggtaatgggg acaagatgcg gccctggtgc tgtaggctac atcctgatac ctataagttc    2580
acccccaccc cacagctgct ggagagaaat cccaagaggc agcccttcct caccatccca    2640
ttaaagaccg ggctggttag cgtccagctc agggagaagg gcgctagtgc ctaacctcac    2700
tggtccctct cccggaggcc cttgtagagg gccacgtcca taaattttct tatggaactc    2760
tcccacatcc tcttccccaa cttcatttgc ttctctcaac aacctcatct gcattttcta    2820
tttctatatg atacagactc tatattgcta tatctctgta tatactttcc cagccctgtc    2880
tgtctccacc ccatccctc ttgtctctga gaaccattct cccaccccaa gttccacctt    2940
ctatgtttct actccctccc tggtctctga atgccttcgc ctgtataaag agttggactc    3000
tctcccctgg tgtctgtact gtgtacacac atccctctga aagcacaag gagacgacac    3060 gcgcattgta acctttgcac tgtctcagtg gcgacaaagg aagctgtgaa tcacaagctc    3120
tgcctctttc tggcctcacc ctctccccca acccgggcac cctcggccct cctgcagcc    3180 ttaacattct cttcccctgc tcctcctatc ccattgccct ctgccagct gacagtggca    3240 tccccaggga aggggttgct gtagagatag cccccaccca ggggatggag gtctaccctg    3300
gacactaagc caagtgtgtc agagacagaa gggagctggg gattggcgac tcctgaagtt    3360
ggggcagtgg gatgctgaca ggcagaagct gaggtcctca gtcagtggcc tttcctcctt    3420
ctgggtgccc agccccttt cctcacctga tacccaagcc caccactttt attttctggt    3480
gaggtgggtt tggaggaaaa agagaggccta gaggaggagt tgaaagctct gctgttgtct    3540
caccctatct taatgagaga caagtgaggt ggagggcctg cccccctcc ctccaccaga    3600 cactccttcc aggcctgagc cccaaccct cttcaggcct tccttcccta gctgtgtctt    3660
ggtcttcaat cccagaacag gacctgtgag cagctgcatt ggcctggagc tggagagtaa    3720
ggctgtagga tctttggaat ctcttggttc ctaagagtttt cctcagagat catacctccc    3780
cagagggaag caggaatgag gccaaaaagt gtgcattgga taggggaaca gcaggcaggg    3840
ctctgggtga cgcatgcctc tggtctaata aactgggttt caacca                    3886
```

<210> SEQ ID NO 2
<211> LENGTH: 20
<212> TYPE: DNA
<213> ORGANISM: Mus musculus

<400> SEQUENCE: 2
ctgtaccatg ctggggaact                                                    20

<210> SEQ ID NO 3
<211> LENGTH: 20
<212> TYPE: DNA
<213> ORGANISM: Mus musculus

<400> SEQUENCE: 3
gctgcttttc atcagccatc                                                    20

<210> SEQ ID NO 4
<211> LENGTH: 19
<212> TYPE: DNA
<213> ORGANISM: Mus musculus

<400> SEQUENCE: 4
tgccagccat gtctttgtg                                                     19

<210> SEQ ID NO 5

```
<211> LENGTH: 18
<212> TYPE: DNA
<213> ORGANISM: Mus musculus

<400> SEQUENCE: 5
cacaggaagg cacccagt                                                    18

<210> SEQ ID NO 6
<211> LENGTH: 18
<212> TYPE: DNA
<213> ORGANISM: Mus musculus

<400> SEQUENCE: 6
gaggtgctgc tgatgtgc                                                    18

<210> SEQ ID NO 7
<211> LENGTH: 19
<212> TYPE: DNA
<213> ORGANISM: Mus musculus

<400> SEQUENCE: 7
ggcgttggga ttggtgact                                                   19

<210> SEQ ID NO 8
<211> LENGTH: 20
<212> TYPE: DNA
<213> ORGANISM: Artificial sequence
<220> FEATURE:
<223> OTHER INFORMATION: synthetic sequence

<400> SEQUENCE: 8
ccgctcgtag gagaagatgt                                                  20

<210> SEQ ID NO 9
<211> LENGTH: 20
<212> TYPE: DNA
<213> ORGANISM: Artificial Sequence
<220> FEATURE:
<223> OTHER INFORMATION: synthetic sequence

<400> SEQUENCE: 9
ccatgtcacc aagctcgacg                                                  20

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10
ggctaaagcg gaactcgttg                                                  20

<210> SEQ ID NO 11
<211> LENGTH: 25
<212> TYPE: DNA
<213> ORGANISM: Homo sapiens

<400> SEQUENCE: 11
cctcaacctc ggatgactat atctg                                            25

<210> SEQ ID NO 12
<211> LENGTH: 22
<212> TYPE: DNA
<213> ORGANISM: Homo sapiens
```

```
<400> SEQUENCE: 12
cgagctgttc tggactatgc tg                                              22

<210> SEQ ID NO 13
<211> LENGTH: 20
<212> TYPE: DNA
<213> ORGANISM: Homo sapiens

<400> SEQUENCE: 13
ccgctttagc caagtctcca                                                 20

<210> SEQ ID NO 14
<211> LENGTH: 20
<212> TYPE: DNA
<213> ORGANISM: Homo sapiens

<400> SEQUENCE: 14
ctgccatctg tgtgtctggt                                                 20

<210> SEQ ID NO 15
<211> LENGTH: 21
<212> TYPE: DNA
<213> ORGANISM: Homo sapiens

<400> SEQUENCE: 15
tgacactggc aaaacaatgc a                                               21

<210> SEQ ID NO 16
<211> LENGTH: 21
<212> TYPE: DNA
<213> ORGANISM: Homo sapiens

<400> SEQUENCE: 16
ggtccttttc accagcaagc t                                               21

<210> SEQ ID NO 17
<211> LENGTH: 78
<212> TYPE: PRT
<213> ORGANISM: Psalmopoeus cambridgei

<400> SEQUENCE: 17

Glu Asp Cys Ile Pro Lys Trp Lys Gly Cys Val Asn Arg His Gly Asp
1               5                  10                  15

Cys Cys Glu Gly Leu Glu Cys Trp Lys Arg Arg Ser Phe Glu Val
            20                  25                  30

Cys Val Pro Lys Thr Pro Thr Glu Asp Cys Ile Pro Lys Trp Lys Gly
        35                  40                  45

Cys Val Asn Arg His Gly Asp Cys Cys Glu Gly Leu Glu Cys Trp Lys
    50                  55                  60

Arg Arg Arg Ser Phe Glu Val Cys Val Pro Lys Thr Pro Thr
65                  70                  75

<210> SEQ ID NO 18
<211> LENGTH: 39
<212> TYPE: PRT
<213> ORGANISM: Psalmopoeus cambridgei

<400> SEQUENCE: 18

Glu Asp Cys Ile Pro Lys Trp Lys Gly Cys Val Asn Arg His Gly Asp
1               5                  10                  15
```

```
Cys Cys Glu Gly Leu Glu Cys Trp Lys Arg Ala Arg Ser Phe Glu Ala
            20                  25                  30

Cys Val Pro Lys Thr Pro Thr
        35

<210> SEQ ID NO 19
<211> LENGTH: 75
<212> TYPE: PRT
<213> ORGANISM: Hadronyche infensa

<400> SEQUENCE: 19

Asn Glu Cys Ile Arg Lys Trp Leu Ser Cys Val Asp Arg Lys Asn Asp
1               5                   10                  15

Cys Cys Glu Gly Leu Glu Cys Tyr Lys Arg His Ser Phe Glu Val
            20                  25                  30

Cys Val Pro Ile Pro Gly Phe Cys Leu Val Lys Trp Lys Gln Cys Asp
        35                  40                  45

Gly Arg Glu Arg Asp Cys Cys Ala Gly Leu Glu Cys Trp Lys Arg Ser
    50                  55                  60

Gly Asn Lys Ser Ser Val Cys Ala Pro Ile Thr
65                  70                  75

<210> SEQ ID NO 20
<211> LENGTH: 23
<212> TYPE: DNA
<213> ORGANISM: Artificial Sequence
<220> FEATURE:
<223> OTHER INFORMATION: synthetic sequence

<400> SEQUENCE: 20
ccgaggagga ggaggtgggt ggt                                         23

<210> SEQ ID NO 21
<211> LENGTH: 23
<212> TYPE: DNA
<213> ORGANISM: Artificial Sequence
<220> FEATURE:
<223> OTHER INFORMATION: synthetic sequence

<400> SEQUENCE: 21
gtaccatgct ggggaactgc tgg                                         23
```

GENOME-EDITED INDUCED PLURIPOTENT STEM CELLS, AND CELLS DERIVED THEREFROM, AND USES THEREOF

SEQUENCE LISTING

The instant application contains a Sequence Listing which has been submitted electronically in ASCII format and is hereby incorporated by reference in its entirety. Said ASCII copy, created on Mar. 10, 2021, is named 5713_0037_Sequence_Listing.txt and is 9,995 bytes in size.

FIELD

This invention relates to compositions and uses of genome edited iPSCs and cells derived therefrom. In particular the iPSCs and cells derived therefrom and compositions comprising the same according to the present invention may be used in cell-based therapies for tissue repair or regeneration. The invention relates to the treatment and/or prevention of injury to the myocardium, and/or ischemia reperfusion injury in the myocardium and other vascularized tissues.

BACKGROUND

Ischemia-reperfusion injury (IRI) is one of the major risk factors implicated in morbidity and mortality associated with cardiovascular disease. Although acute reperfusion therapies have improved patient outcomes, mortality remains high and MI is one of the largest attributable risks for heart failure (HF). Globally, 1 in 5 people develop HF, with annual healthcare costs of $108B. Heart transplantation remains the most effective treatment option for HF, but 75% of potential donor hearts are discarded, many due to sensitivity of the donor heart to ischemic injury. Myocardial sensitivity to IRI therefore remains a primary point of vulnerability underlying cardiovascular disease, which is the leading cause of morbidity and mortality worldwide.

Myocardial IRI is a complex pathophysiological process that underlies the cardiac injury sustained during cardiac surgery, heart transplant, MI, and cardiac arrest. During myocardial ischemia, reduced oxygen availability causes a shift from fatty acid metabolism to anaerobic glycolysis. The resulting lactic acidosis causes a significant drop in both extracellular and intracellular pH, reaching as low as 6.0-6.5. In patients suffering from acute MI, the severity of metabolic acidosis strongly correlates with patient mortality, with serum pH<7.35 associated with >60% mortality.

At the cellular level, acidosis results in the activation of several transmembrane ion channels and receptors, including the sodium-hydrogen exchanger (NHE), glutamate-gated NMDA receptors, and the TRP family of ion channels, each of which are thought to contribute to calcium overload, metabolic dysfunction, and eventually cell death. In line with this, a clinical trial of cariporide, an NHE inhibitor, showed significant protection against peri-operative MI in patients undergoing high-risk coronary artery bypass surgery. While this trial failed due to cerebrovascular complications, it demonstrated that pharmacological conditioning has the capacity to reduce the injury response to myocardial IRI.

Despite decades of preclinical therapeutic development, there are no drugs that block the acute injury response to cardiac ischemia. Human cell therapeutic approaches have also failed to reach expected outcomes in the repair and regeneration of cardiac tissues. This is due to the lack of survival of stem cell-derived cardiomyocytes following transplantation and their lack of stability in vivo. Therefore, new approaches to improve survival of human cells differentiated in vitro are needed to improve treatment outcomes for patients with cardiovascular disease, cardiac injuries, or other diseases that rely on stem cell or cell transplant therapies. Furthermore, the provision of cell-based therapies for tissue repair and regeneration of following ischemic injury represents an unmet need.

SUMMARY OF INVENTION

The methods and compositions described herein are related, in part, to the discovery that inhibition of proton-gated acid-sensing ion channel 1a (ASIC1a) plays a key role during cardiac ischemia and the surprising findings that inhibition of ASIC1a (via genetic ablation or pharmacological blockade of IRI) improves the tolerance of in vitro-differentiated cells and cardiac tissue to ischemia (enhances viability of cardiac tissue post-IRI) and improved functional recovery following global myocardial IRI and that acute exposure to ASIC1a inhibitors has no impact on cardiac ion channels regulating baseline electromechanical coupling and physiological performance.

In one aspect, described herein is a composition comprising human cells differentiated in vitro from stem cells which have been genetically modified to lack, or have decreased or disrupted expression and/or activity of ASIC1a. In one embodiment the stem cells are ASIC1a$^{-/-}$.

In one embodiment, the composition is a transplant composition.

In another embodiment, the cells differentiated in vitro from stem cells are of a mesodermal lineage.

In another embodiment, the cells differentiated in vitro are of a cell type selected from: cardiac progenitor cells, endothelial progenitor cells, cardiomyocytes, skeletal muscle cells, smooth muscle cells, kidney cells, endothelial cells, skin cells, adrenal cortex cells, bone cells, white blood cells, and microglial cells.

In another embodiment, the cells differentiated in vitro from stem cells are cardiomyocytes.

In another embodiment, the cells differentiated in vitro from stem cells are of an ectodermal lineage.

In another embodiment, the cells differentiated in vitro from stem cells are neural stem cells, neurons, astrocytes, oligodendrocytes, or glial cells.

In another embodiment, the in vitro-differentiated human cells are differentiated from induced pluripotent stem cells (iPSCs).

In another embodiment, the stem cells are derived from a healthy subject. In another embodiment the cells are derived from a subject to be treated (i.e. autologous cells).

In another embodiment, the composition further comprises an additional therapeutic agent. In one embodiment, the additional therapeutic agent is a small molecule, a polypeptide, a nucleic acid molecule or a vector comprising a nucleic acid molecule.

In another embodiment, the composition further comprises an additional agent which promotes the survival of the cells of said composition when administered to a subject. In one embodiment, the additional agent which promotes the survival of the cells of said composition is a small molecule, a polypeptide, a nucleic acid molecule or a vector comprising a nucleic acid molecule. In another embodiment, the agent which promotes the survival of the cells of said composition when administered to a subject is an apoptosis inhibitor, or a necrosis inhibitor.

In one embodiment composition comprises an agent that decreases the level or activity of ASIC1a. In another embodiment the agent which the decreases the level or activity of ASIC1a is selected from Hi1a and PcTx1. In a preferred embodiment the agent that decreases the level or activity of ASIC1a is Hi1a.

In one aspect, described herein is a composition comprising human cells differentiated in vitro from stem cells and an agent that decreases the level or activity of ASIC1a.

In one embodiment, the cells of the composition are differentiated in vitro from stem cells which have been genetically modified to lack, or have decreased expression and/or activity of ASIC1a. In one embodiment the stem cells are ASIC1a$^{-/-}$.

In one embodiment, the composition is a transplant composition.

In another embodiment, the cells differentiated in vitro from stem cells are of a mesodermal lineage.

In another embodiment, the in vitro-differentiated cells are of a cell type selected from: cardiac progenitor cells, endothelial progenitor cells, cardiomyocytes, skeletal muscle cells, smooth muscle cells, kidney cells, endothelial cells, skin cells, adrenal cortex cells, bone cells, white blood cells, and microglial cells.

In another embodiment, the cells differentiated in vitro from stem cells are cardiomyocytes.

In another embodiment, the cells differentiated in vitro from stem cells are of an ectodermal lineage.

In another embodiment, the cells differentiated in vitro from stem cells are neural stem cells, neurons, astrocytes, oligodendrocytes, or glial cells.

In another embodiment, the in vitro-differentiated human cells are differentiated from induced pluripotent stem cells (iPSCs).

In another embodiment, the stem cells are derived from a healthy subject. In another embodiment the cells are derived from a subject to be treated (i.e. autologous cells).

In another embodiment, the agent is a small molecule, a polypeptide, a nucleic acid molecule or a vector comprising a nucleic acid molecule.

In another embodiment the agent which decreases the level or activity of ASIC1a is selected from Hi1a and PcTx1. In a preferred embodiment the agent that decreases the level or activity of ASIC1a is Hi1a.

In another embodiment, the agent comprises or encodes a nucleic acid molecule comprising an antisense sequence, an aptamer or an RNA interference molecule (RNAi) that targets ASIC1a or its RNA transcript. In another embodiment, the vector is selected from the group consisting of: a plasmid and a viral vector.

In another embodiment, the composition further comprises an additional agent which promotes the survival of the cells of said composition when administered to a subject. In one embodiment, the additional agent which promotes the survival of the cells of said composition is a small molecule, a polypeptide, a nucleic acid molecule or a vector comprising a nucleic acid molecule. In another embodiment, the agent which promotes the survival of the cells of said composition when administered to a subject is an apoptosis inhibitor, or a necrosis inhibitor.

In another aspect, described herein is a method of transplanting in vitro-differentiated cells to a subject in need thereof, comprising administering to said subject a composition as described in any of the above described aspects or embodiments.

In another aspect, described herein is a method of transplanting in vitro-differentiated human mesodermal lineage cells, the method comprising transplanting into or onto a tissue or organ of a subject in vitro-differentiated human mesodermal lineage cells that have been derived from stem cells which have been genetically modified to lack or have decreased expression and/or activity of ASIC1a. In one embodiment the stem cells are ASIC1a$^{-/-}$.

In one embodiment of any of the aspects, the cells are cardiomyocytes. In another embodiment, the cells are cardiomyocytes and the subject has suffered a myocardial infarction.

In another embodiment, the human cardiomyocytes are differentiated from iPSCs. In another embodiment, the iPSCs are derived from the subject. In another embodiment, the iPSCs are derived from a healthy donor.

In another embodiment, the method further comprises administering an additional agent which promotes the survival of the cells when administered to a subject. In one embodiment, the additional agent which promotes the survival of the cells of said composition is a small molecule, a polypeptide, a nucleic acid molecule or a vector comprising a nucleic acid molecule. In another embodiment, the agent which promotes the survival of the cells of said composition when administered to a subject is an apoptosis inhibitor, or a necrosis inhibitor.

In another aspect, described herein is a method of promoting survival and/or engraftment of transplanted human, in vitro-differentiated cardiomyocytes, the method comprising administering to a subject in need thereof in vitro-differentiated cardiomyocytes that have been derived from stem cells which have been genetically modified to lack or have decreased expression and/or activity of ASIC1a. In one embodiment the stem cells are ASIC1a$^{-/-}$.

In another aspect, described herein is a method of promoting survival and/or engraftment of transplanted human, in vitro-differentiated cardiomyocytes, the method comprising contacting human, in vitro-differentiated cardiomyocytes with an agent that decreases the level or activity of ASIC1a in said cells, and transplanting the cells into cardiac tissue of a human subject in need thereof.

In one embodiment, the subject has suffered a myocardial infarct.

In one embodiment, the method comprises administering or transplanting said cells in combination with an agent which the decreases the level or activity of ASIC1a.

In another embodiment, the agent is a small molecule, a polypeptide, a nucleic acid molecule or a vector comprising a nucleic acid molecule.

In another embodiment the agent which the decreases the level or activity of ASIC1a is selected from Hi1a and PcTx1. In a preferred embodiment the agent that decreases the level or activity of ASIC1a is Hi1a.

In another embodiment, the agent comprises or encodes a nucleic acid molecule comprising an antisense sequence, an aptamer or an RNA interference molecule (RNAi) that targets ASIC1a or its RNA transcript. In another embodiment, the vector is selected from the group consisting of: a plasmid and a viral vector.

In another aspect, described herein is a method of promoting survival and/or engraftment of transplanted mesoderm lineage cells, the method comprising: administering to a subject in need thereof in vitro-differentiated mesoderm lineage cells that have been derived from stem cells which have been genetically modified to lack or have decreased expression and/or activity of ASIC1a. In one embodiment the stem cells are ASIC1a$^{-/-}$.

In another aspect, described herein is a method of promoting survival and/or engraftment of transplanted mesoderm lineage cells, the method comprising: administering to a subject in need thereof mesoderm lineage cells contacted or treated with an agent that decreases the level or activity of ASIC1a in the subject.

In another aspect, the present invention provides use of a composition as defined in any of the aspects or embodiments which comprise in vitro-differentiated mesoderm lineage cells as described above, in the manufacture of a medicament for the transplantation of vitro-differentiated mesoderm lineage cells to a subject in need thereof.

In another aspect, the present invention provides a composition as defined in any of the aspects or embodiments which comprise in vitro-differentiated mesoderm lineage cells as described above for use in transplantation of cells to a subject in need thereof.

In another aspect, the present invention provides use of a composition as defined in any of the aspects or embodiments which comprise in vitro-differentiated mesoderm lineage cells as described above, in the manufacture of a medicament for the treatment of a myocardial infarct of in a subject in need thereof.

In another aspect, the present invention provides a composition as defined in any of the aspects or embodiments which comprise in vitro-differentiated mesoderm lineage cells as described above for use in the treatment of a myocardial infarct of in a subject in need thereof.

In another aspect, the present invention provides use of a composition as defined in any of the aspects or embodiments which comprise in vitro-differentiated mesoderm lineage cells as described above, in the manufacture of a medicament for cardiovascular repair or regeneration in a subject in need thereof.

In another aspect, the present invention provides a composition as defined in any of the aspects or embodiments which comprise in vitro-differentiated mesoderm lineage cells as described above for use in cardiovascular repair or regeneration in a subject in need thereof.

In another aspect, described herein is a method of promoting survival and/or engraftment of transplanted ectodermal lineage cells, the method comprising: administering to a subject in need thereof in vitro-differentiated ectodermal lineage cells that have been derived from stem cells which have been genetically modified to lack or have decreased expression and/or activity of ASIC1a. In one embodiment the stem cells are ASIC1a$^{-/-}$. In one embodiment, the ectoderm-derived cells are neural stem cells, neurons, astrocytes, oligodendrocytes, or glial cells.

In another aspect, described herein is a method of promoting survival and/or engraftment of transplanted ectodermal lineage cells, the method comprising: administering to a subject in need thereof ectoderm lineage cells contacted or treated with an agent that decreases the level or activity of ASIC1a in the subject. In one embodiment, the ectoderm-derived cells are neural stem cells, neurons, astrocytes, oligodendrocytes, or glial cells.

In another aspect, the present invention provides a composition as defined in any of the aspects or embodiments which comprise in vitro-differentiated ectoderm lineage cells as described above for use in transplantation of cells to a subject in need thereof.

In another aspect, the present invention provides use of a composition as defined in any of the aspects or embodiments which comprise in vitro-differentiated ectoderm lineage cells as described above, in the manufacture of a medicament for the treatment of ischemic stroke in a subject in need thereof. In a preferred embodiment the ischemic stroke is small vessel stroke.

In another aspect, the present invention provides a composition as defined in any of the aspects or embodiments which comprise in vitro-differentiated ectoderm lineage cells as described above for use in the treatment of ischemic stroke in a subject in need thereof. In a preferred embodiment the ischemic stroke is small vessel stroke.

In an embodiment of the aforementioned methods, uses, and compositions for the recited uses, said cells are administered, or are formulated to be administered, in combination with an agent which the decreases the level or activity of ASIC1a.

In another embodiment, the agent is a small molecule, a polypeptide, a nucleic acid molecule or a vector comprising a nucleic acid molecule.

In another embodiment the agent which the decreases the level or activity of ASIC1a is selected from Hi1a and PcTx1. In a preferred embodiment the agent that decreases the level or activity of ASIC1a is Hi1a.

In another embodiment, the agent comprises or encodes a nucleic acid molecule comprising an antisense sequence, an aptamer or an RNA interference molecule (RNAi) that targets ASIC1a or its RNA transcript. In another embodiment, the vector is selected from the group consisting of: a plasmid and a viral vector.

In another embodiment, of the aforementioned methods, uses, and compositions for the recited uses, said cells are administered, or are formulated to be administered, in combination with an agent which promotes the survival of the cells when administered to a subject.

In one embodiment, the additional agent which promotes the survival of the cells of said composition is a small molecule, a polypeptide, a nucleic acid molecule or a vector comprising a nucleic acid molecule. In another embodiment, the agent which promotes the survival of the cells of said composition when administered to a subject is an apoptosis inhibitor, or a necrosis inhibitor.

Numbered statements of the invention are as follows:
1. A composition comprising cells differentiated in vitro from stem cells which have been genetically modified to lack, or have decreased or disrupted expression and/or activity of ASIC1a.
2. The composition of statement 1, the cells differentiated in vitro from stem cells are of a mesodermal lineage selected from: cardiac progenitor cells, endothelial progenitor cells, cardiomyocytes, skeletal muscle cells, smooth muscle cells, kidney cells, endothelial cells, skin cells, adrenal cortex cells, bone cells, white blood cells, and microglial cells; or are of an ectodermal lineage selected from: are neural stem cells, neurons, astrocytes, oligodendrocytes, or glial cells.
3. The composition of statement 2, wherein the cells differentiated in vitro from stem cells are cardiomyocytes.
4. The composition of statement 1, wherein the cells differentiated in vitro are differentiated from human induced pluripotent stem cells (iPSCs).
5. The composition of statement 1, wherein said stem cells are genetically modified to have a ASIC1a$^{-/-}$ phenotype.
6. The composition of statement 1, wherein the stem cells are derived from a healthy subject.
7. The composition of statement 1, wherein the cells are derived from a subject to be treated (i.e. autologous cells).
8. The composition of statement 1, wherein in vitro differentiated cells comprise a combination of one or more cell types of a mesodermal lineage 9. The composition of statement 1, wherein the transplant composition comprises a pharmaceutically acceptable carrier.
10. The composition of statement 1, wherein the composition further comprises an additional agent wherein the additional agent is a therapeutic agent or an agent that promotes the survival of the cells of said composition when administered to a subject.
11. The composition of statement 1, wherein the agent which promotes the survival of the cells of said composition when administered to a subject is an apoptosis inhibitor, or a necrosis inhibitor.
12. The composition of statement 1, wherein the additional agent is one that decreases the level or activity of ASIC1a.
13. The composition of statement 1, wherein the additional agent is selected from Hi1a and PcTx1.
14. A method of transplanting in vitro-differentiated human mesodermal lineage cells, the method comprising transplanting into or onto a tissue or organ of a subject in vitro-differentiated human mesodermal lineage cells that have been derived from stem cells which have been genetically modified to lack or have decreased expression and/or activity of ASIC1a.
15. The method of statement 14, wherein the stem cells have a ASIC1a−/− phenotype.
16. The method of statement 14, wherein, the in vitro-differentiated human mesodermal lineage cells are cardiomyocytes.
17. The method of statement 14, wherein the cells are cardiomyocytes and the subject has suffered a myocardial infarction.
18. The method of statement 14, wherein the human cardiomyocytes are differentiated from iPSCs.
19. The method of statement 18, wherein the iPSCs are derived from the subject.
20. A method of promoting survival and/or engraftment of transplanted human, in vitro-differentiated cardiomyocytes, the method comprising administering to a subject in need thereof in vitro-differentiated cardiomyocytes that have been derived from stem cells which have been genetically modified to lack or have decreased expression and/or activity of ASIC1a.

All patents and other publications identified are expressly incorporated herein by reference for the purpose of describing and disclosing, for example, the methodologies described in such publications that might be used in connection with the present disclosure. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

(D-G) Functional parameters including ejection fraction (D) cardiac index (E), as well as LV end systolic (F) and diastolic (G) internal volume measured by serial echocardiography at baseline, 1 week, and 4 weeks post injury. All data are expressed as mean±SEM (n=5-7/group). Statistical significance was determined using one-way (panel c) or two-way repeated measures (panels d-g) ANOVA with multiple comparisons (*p<0.05; p<0.01, *p<0.001).

Figure 4:
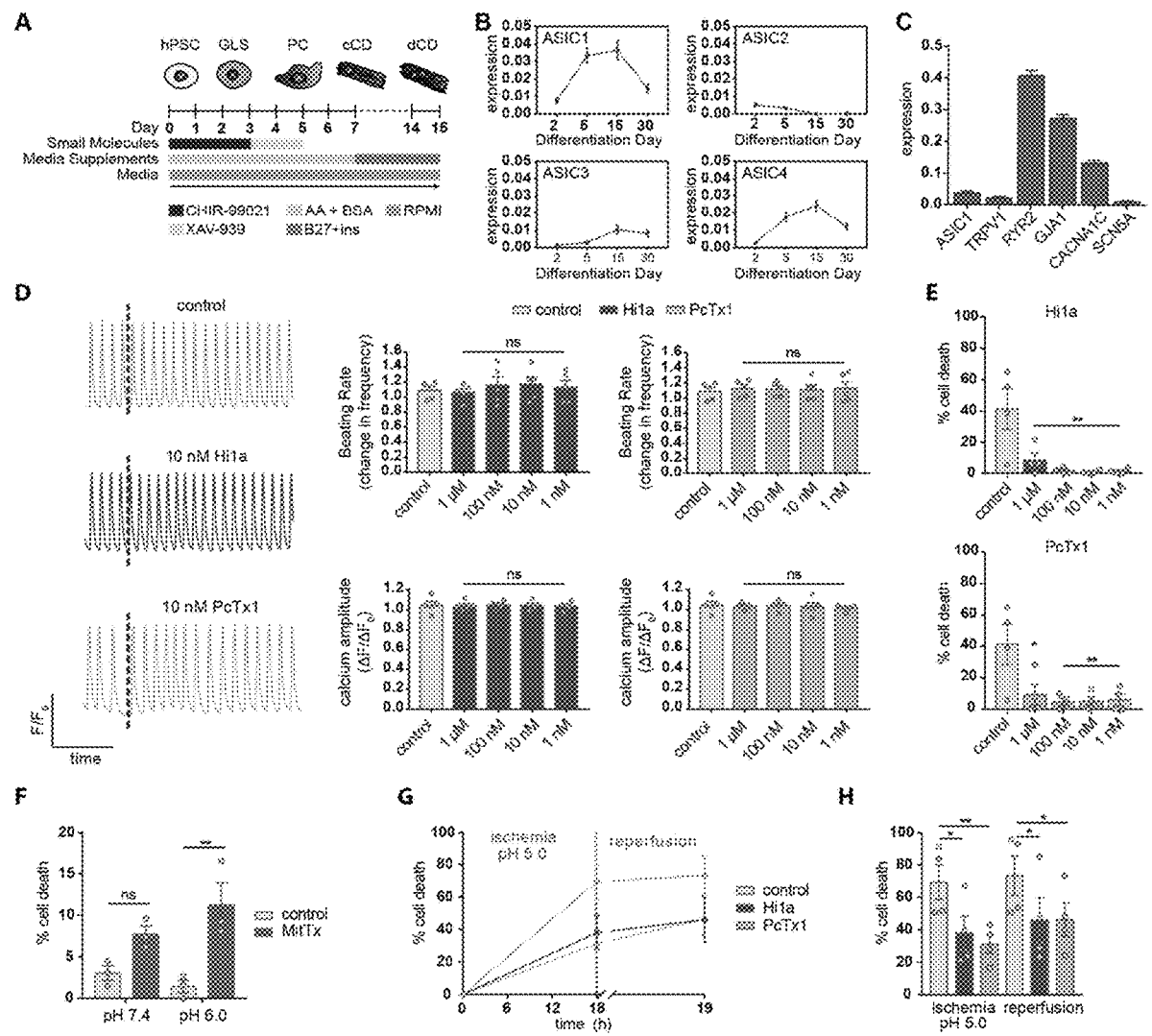

FIG. 4. Hi1a protects hiPSC-CMs from ischemic injury. (A) Schematic depicting directed differentiation of hiPSC-CMs (adapted from Ref. (1)). (B-C) Analysis of published transcriptomic data (scRNAseq) of cardiac differentiation (1). (B) Expression of ASIC1, ASIC2, ASIC3, and ASIC4 at day 0, 2, 5, 15, and 30 of differentiation. (C) Gene expression in day-15 hiPSC-CMs. Abbreviations: RYR2=ryanodine receptor 2; GJA1=gap junction alpha1 protein (connexin 43). (D) Fluorescent imaging of calcium transients (normalized arbitrary fluorescent units (F/F0)) before and after Hi1a or PcTx1 addition using a FLIPR Tetra system. Representative traces (black dotted line indicates time of peptide addition) and quantification of spontaneous beat rate and calcium amplitude are shown. Amplitude and beat rate are both expressed as a response over baseline (post-addition measurement normalized to pre-addition measurement). (E) Cell death (LDH secretion) analysis after overnight treatment in HBSS pH 5.0 with or without Hi1a (top) or PcTx1 (bottom). (F) Cell death (LDH) after overnight treatment with 20 nM MitTx in HBSS pH 7.4 or HBSS pH 6.0. (G-H) Cell death (LDH) after in vitro IRI with overnight hypoxic (0.5% O2) incubation in HBSS pH 5.0 followed by 1 h reperfusion with HBSS pH 7.4 in normoxic conditions. For panels e-h, data are expressed as percent cell death calculated from LDH levels in low (RPMI+B27™) and high (1% Triton™ X-100 in RPMI+B27™) controls. All data are expressed as mean±SEM (n=3-5 biological replicates with 3-6 technical replicates each). Statistical significance was determined using one-way (panel d-e) or two-way (panel f, g) ANOVA with multiple comparisons (*p<0.05; **p<0.01).

Figure 5:
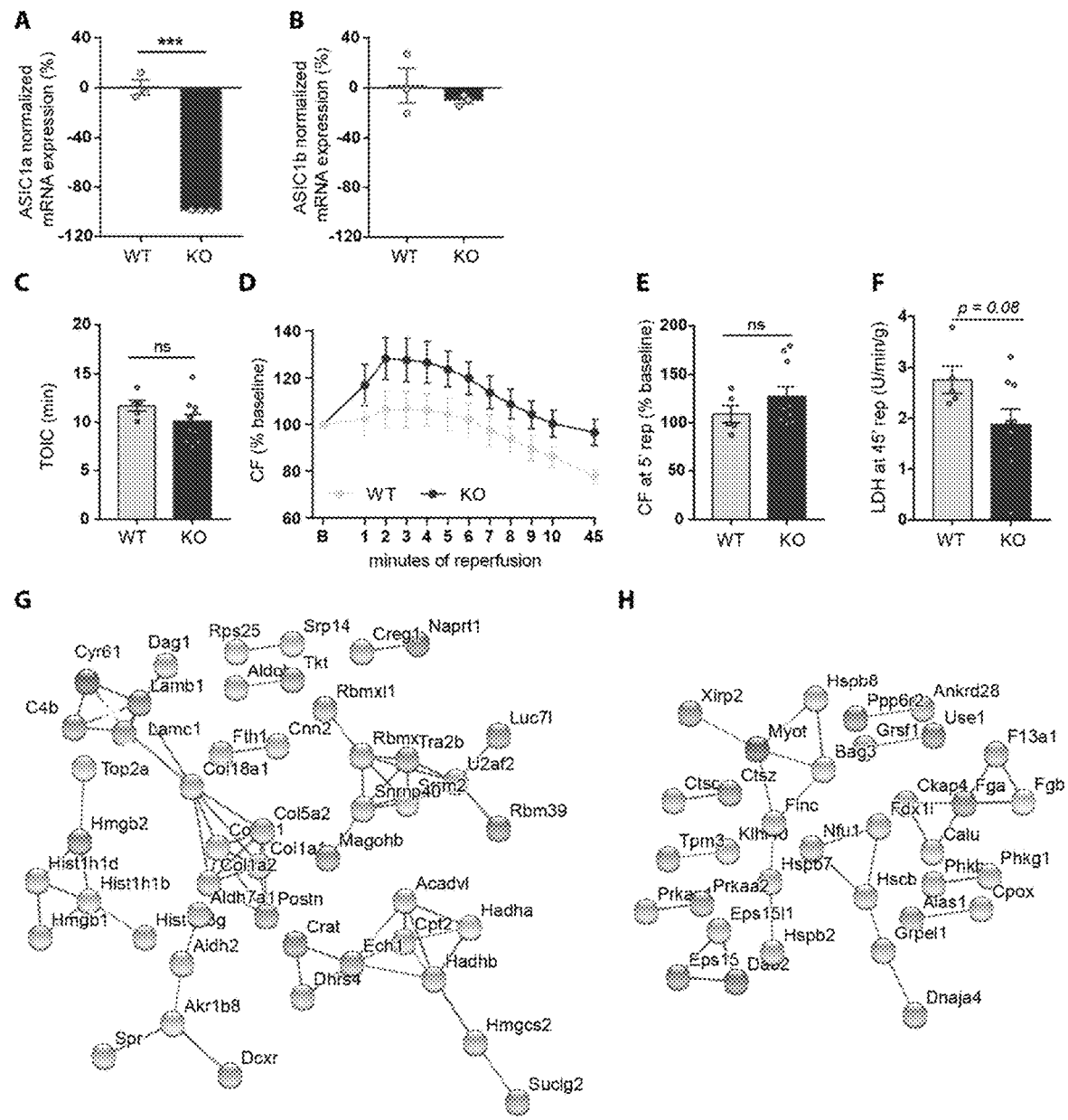

FIG. 5. ASIC1a knockout mouse analysis. (A-B) Normalized mRNA expression levels of (A) ASIC1a (p<0.0001, WT 0.3±6.0%, ASIC1a$_{-/-}$ –98.7±0.7%) and (B) ASIC1b (p=45, WT 1.9±13.8%, ASIC1a$_{-/-}$ –9.9±2.6%) from brain samples from WT (n=3) and ASIC1a$_{-/-}$ mice (n=3). Statistical significance was determined with two-tailed unpaired Student's t-test (***p<0.001). Data are presented as mean±SEM. (C-G) Hearts from ASIC1a KO (ASIC1a$_{-/-}$, n=10, dark gray) and WT (ASIC1a$_{+/+}$, n=5, light grey) mice were subjected to 25 min of global ischemia followed by 45 min of reperfusion. (C) Time to onset of ischemic contracture (TOIC, p=0.162). (D) Coronary flow (CF) at baseline (B, pre-ischemia), during the first 10 min of reperfusion, and at the end of the 45 min reperfusion period. (E) CF at 5 min reperfusion (p=0.26). (F) Cell death after 45 min of reperfusion (units of LDH normalized to reperfusion flow rate and heart weight, U/min/g, p=0.08). For all parameters, baseline values were obtained immediately prior to ischemia, and all data are expressed as mean±SEM. Statistical significance was evaluated with two-tailed unpaired Student's t-test (*p<0.05). (G-H) STRING analysis showing proteins significantly increased (G) and decreased (H) in ASIC1a KO hearts compared to WT hearts.

Figure 2:
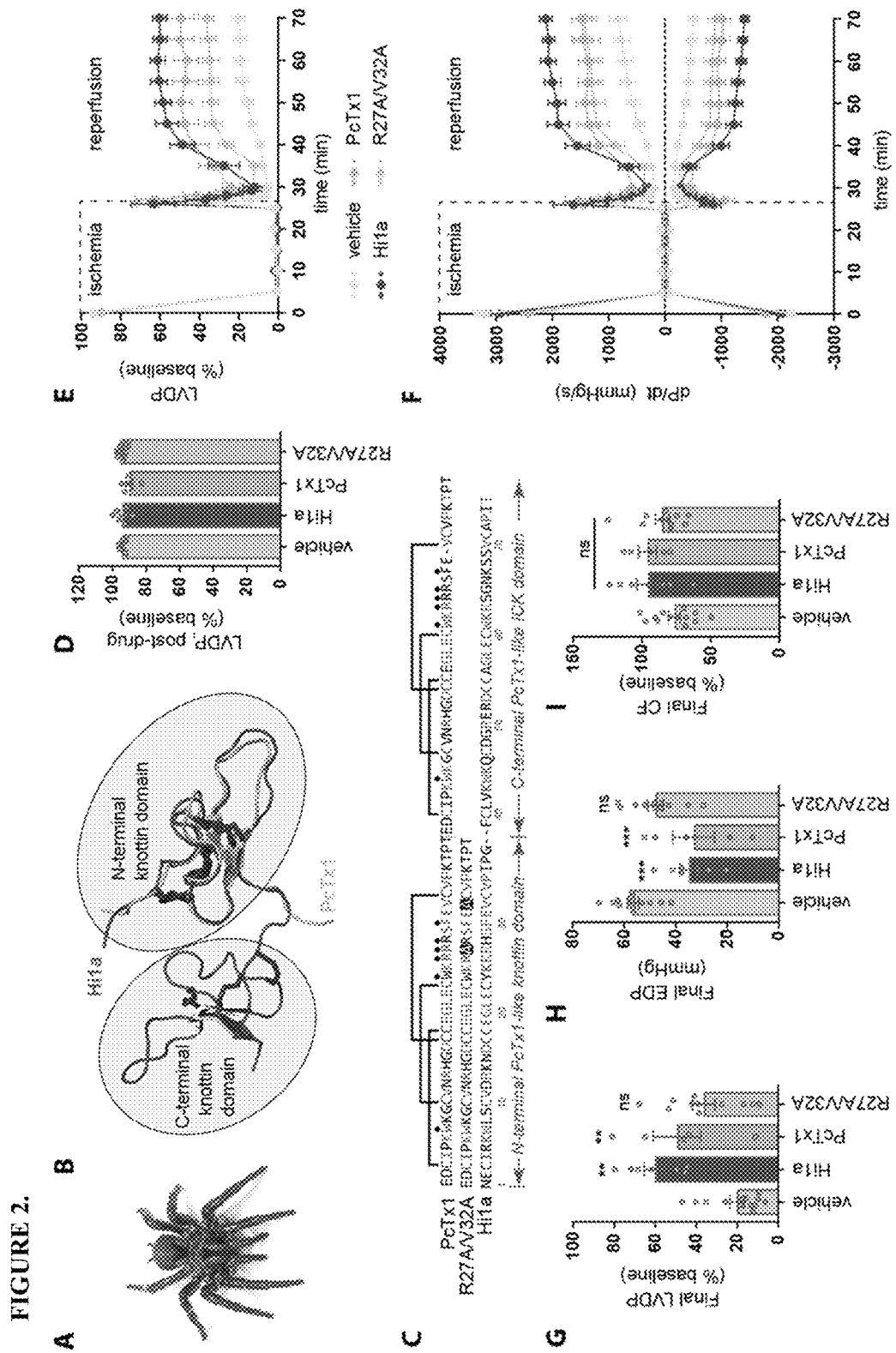
FIG. 2. ASIC1a inhibitors protect isolated mouse hearts from IRI. (A) Australian funnel-web spider, *Hadronyche infensa*, from which the ASIC1a inhibitor Hi1a was isolated. (B) Schematic of the 3D structure of Hi1a (PDB 2N8F (2)) highlighting the two knottin domains. The 3D structure of PcTx1 (PDB 2KNI (3)) is overlaid on the N-terminal knottin domain of Hi1a. The disulfide bonds in each structure are shown as tubes. (C) Sequence alignment of Hi1a, PcTx1, and the PcTx1-R27A/V32A analogue. Conserved residues are highlighted. Black circles indicate pharmacophore residues of PcTx1. (D-H) Langendorff-perfused hearts from adult (12-14 weeks old) male C57BL/6 mice were subjected to 25 min of global ischemia followed by 45 min of reperfusion. Control hearts (no treatment, n=21) were compared to hearts treated with 10 nM Hi1a (n=7), 10 nM PcTx1 (n=5), 10 nM PcTx1-R27A/V32A, n=11), or 0.1% BSA in water (vehicle control, n=13). For treated hearts, vehicle or peptide solution was infused for 10 min prior to ischemia and during the first 15 min of reperfusion. (D) Pre-ischemia LVDP, expressed as % baseline, after exposure to vehicle or peptide for 10 min. (E) LVDP over time. (F) Positive and negative rate of change in pressure over time in hearts treated with Hi1a or PcTx1 variants vs vehicle. (G-I) Functional parameters measured or calculated after 45 min of reperfusion including (G) LVDP (H) EDP and (I) CF. For LVDP and CF, baseline values were obtained prior to peptide/vehicle infusion, or 10 min prior to onset of ischemia (no-infusion controls). All data are expressed as mean±SEM. Statistical significance was determined using one-way ANOVA with multiple comparisons (p<0.01, *p<0.001).
Figure 3:
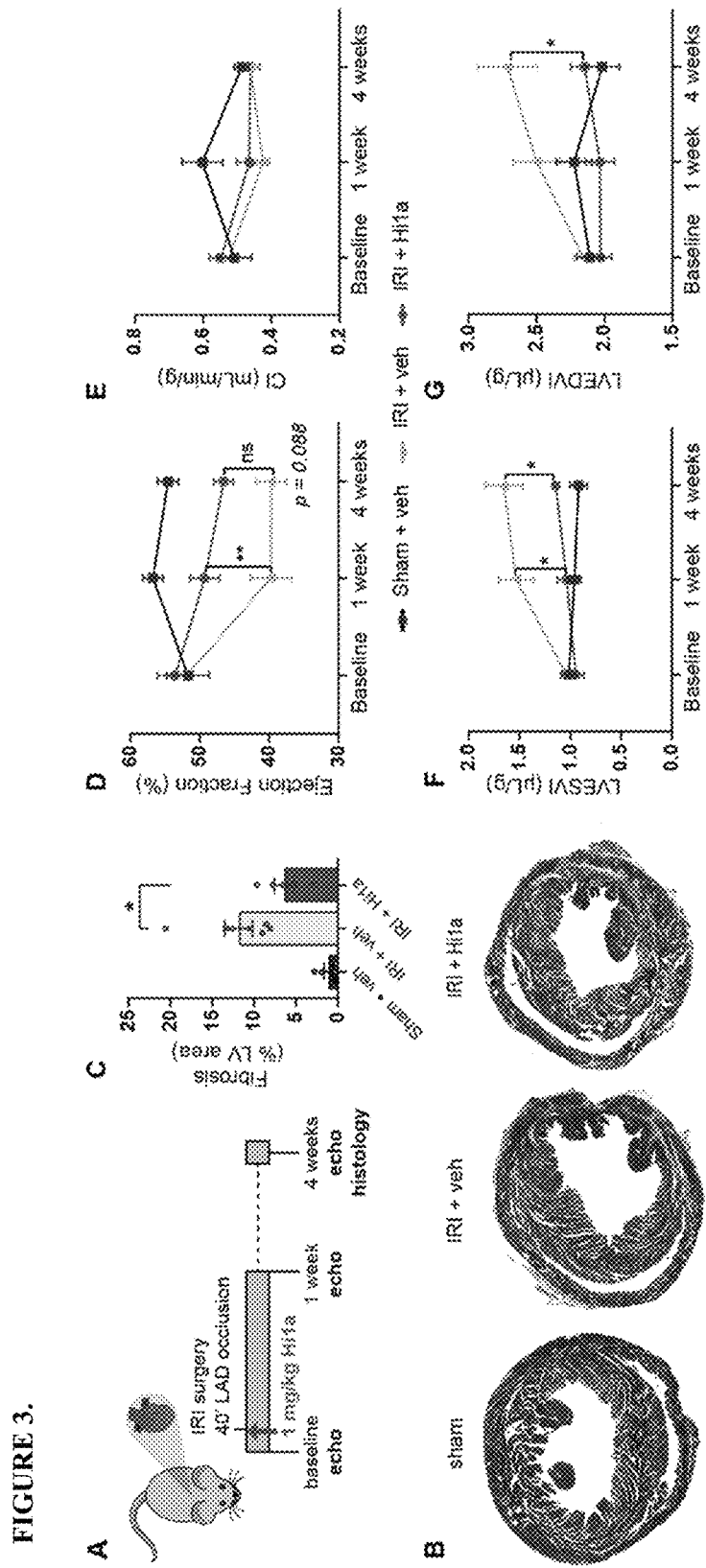
FIG. 3. Hi1a protects post-ischemic cardiac remodelling after IRI in vivo. (A) Schematic of experimental design. (B-C) Mason's trichrome staining of heart sections at 28 days post injury. (B) Representative images of sham, vehicle-treated, and Hi1a-treated hearts depicting healthy myocardium and collagen deposition/fibrosis. (C) Quantification of fibrosis as a percentage of left ventricular area.
Figure 6:
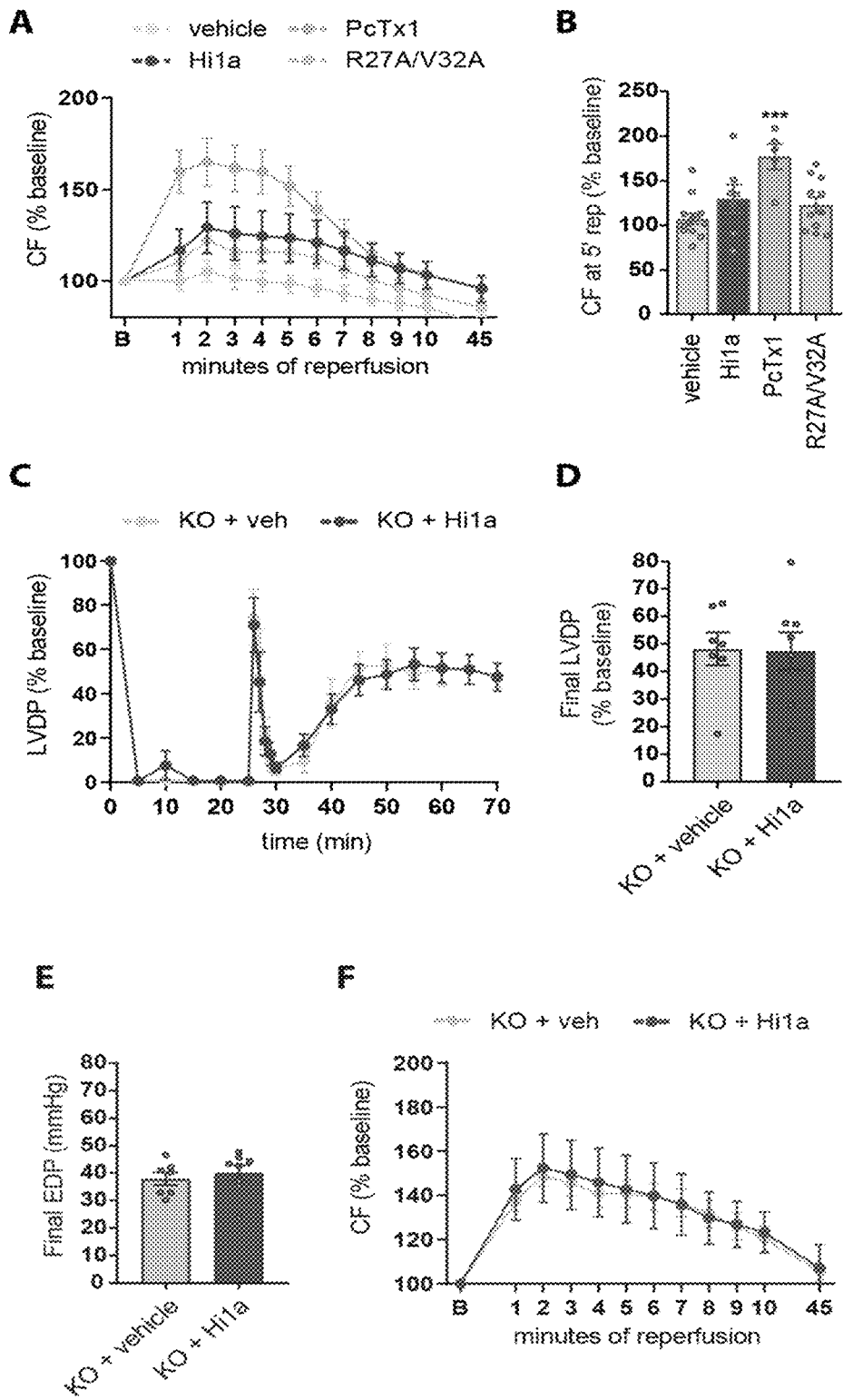

FIG. 6. ASIC1a inhibitors protect mouse hearts from ex vivo IRI. (A-B) Additional analysis of the experiment described in FIG. 2. (A) CF plotted versus time (min) at baseline (B, pre-ischemia), during the first 10 min of reperfusion, and at the end reperfusion (45 min). (B) CF at 5 min reperfusion. Statistical significance was determined using one-way ANOVA with multiple comparisons (***p<0.001). Data are presented as mean±SEM (n>5/group). (C-F) ASIC1a inhibitors do not significantly increase recovery of function in ASIC1a KO hearts (n=7-8/group) based on measures of LVDP (C-D), EDP (E), and CF (F).

Figure 7:
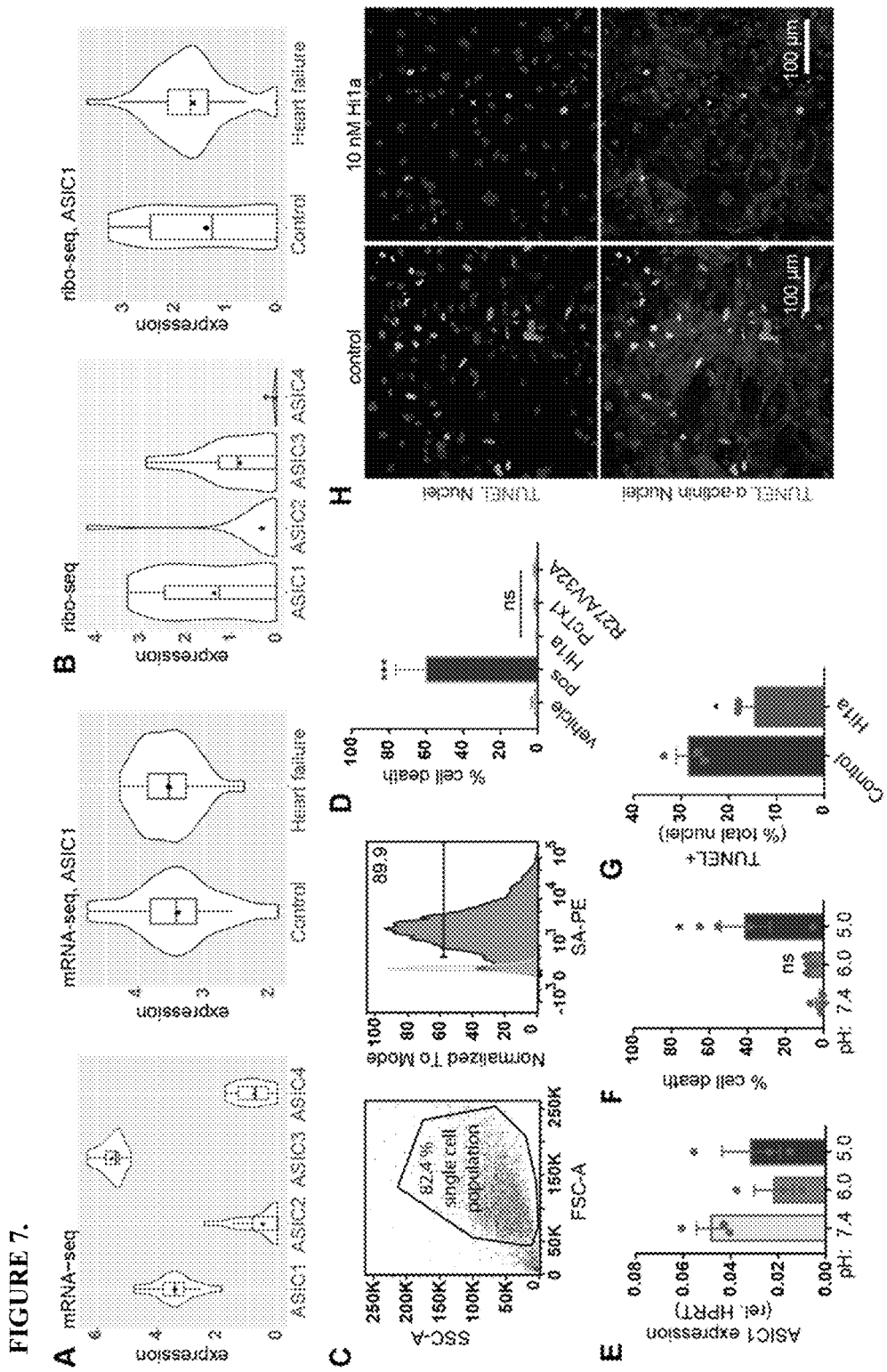

FIG. 7. ASIC expression in human heart muscle. Analysis of published (A) transcriptomic (mRNA-seq) and (B) translatomic (ribo-seq) data from the left ventricles of control (n=15) and heart failure (dilated cardiomyopathy) (n=65) patients (53). Data are presented as box blots where the middle box represents interquartile range (IQR), the middle line in the box is median (50th percentile of the data set), and points outside the plot are outliers. (C-G) Generation of hiPSC-CMs and treatment at low pH. (C) Flow cytometry analysis of differentiated hiPSC-CMs prior to replating. Single cell population from SSC-A (side scatter) versus FSC-A (forward scatter) plot (left) was analysed for the percentage of cells that stained positive for sarcomeric α-actinin (SA, PE-gated population) shown as a histogram (middle) and a scatter plot against an unstained fluorophore (right). Isotype-stained sample (grey) was used to create PE+ gate to analyse SA stained sample. (D) Replated hiPSC-CMs treated for 48 hours in RPMI+B27™ with vehicle (0.1% BSA in water), positive control (10 μM thapsigargin), 10 nM Hi1a, 10 nM PcTx1, or 10 nM PcTx1 R27A/V32A and evaluated for cell death (LDH) (E-F) Replated hiPSC-CMs treated overnight in HBSS at pH 7.4, 6.0, or 5.0 and analysed for (E) mRNA expression (qRT-PCR) of ASIC1 and (F) cell death (LDH). (G-H) Replated hiPSC-CMs treated overnight in HBSS at pH 5.0 with (G) quantification of cell death (TUNEL-positive nuclei normalized to total nuclei) following (H) immunohistochemistry for TUNEL and α-actinin with nuclei counterstained with DAPI. Top panel: TUNEL and DAPI merged image. Bottom panel: TUNEL, α-actinin, and DAPI merged image. All data are expressed as mean f SEM (n=3 biological replicates, 2-3 technical replicates each). Statistical significance was determined with one-way ANOVA (LDH results, panel c) or with a two-tailed unpaired student's t-test (TUNEL quantification, panel d) (*p<0.05).

Figure 8:
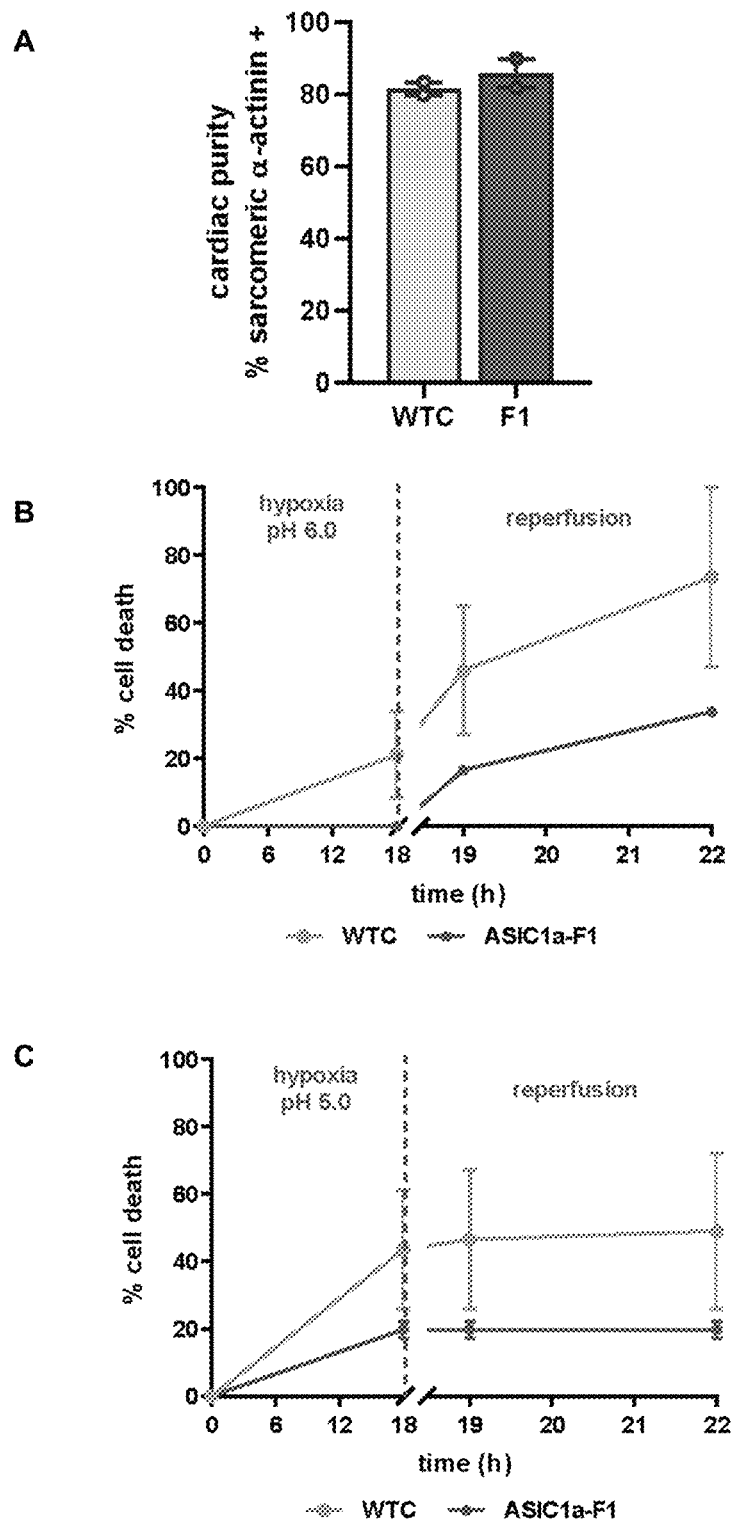

FIG. 8. (A) Flow cytometry analysis of day 15 cardiomyocyte preparations from ASIC1a KO and wildtype controls. Isotype-stained samples were used to gate populations positive for sarcomeric α-actinin (SA, PE-gated population) to determine the cardiomyocyte yield (expressed as percentage of population). (B-C) Cell death analysis (determined by supernatant levels of LDH) after in vitro IRI with overnight hypoxic (0.5% O2) incubation in HBSS pH 6.0 or HBSS pH 5.0 followed by 4 h reperfusion with HBSS pH 7.4 in normoxic conditions. Data are expressed as percent cell death calculated from LDH levels in low (RPMI+B27™) and high (1% Triton™ X-100 in RPMI+B27™) controls. All data are expressed as mean±SEM (n=2 biological replicates with 2-3 technical replicates each).

DESCRIPTION OF EMBODIMENTS

Definitions

Definitions of common terms in cellular and molecular biology, and biochemistry can be found in The Merck Manual of Diagnosis and Therapy, 20th Edition, published by Merck Sharp & Dohme Corp., 2018 (ISBN 9780911910421, 0911910425); Robert S. Porter et al. (eds.), The Encyclopedia of Molecular Cell Biology and Molecular Medicine, published by Blackwell Science Ltd., 2008 (ISBN 3527305424, 9783527305421); and Robert A. Meyers (ed.), Molecular Biology and Biotechnology: a Comprehensive Desk Reference, published by VCH Publishers, Inc., 1995 (ISBN 1-56081-569-8); Immunology by Weiner Luttmann, published by Elsevier, 2006; Janeway's Immunobiology, Kenneth Murphy, Allan Mowat, Casey Weaver (eds.), Taylor & Francis Limited, 2016 (ISBN 9780815345510, 0815345518); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al, Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Laboratory Methods in Enzymology: RNA, Jon Lorsch (ed.) Elsevier, 2013 (ISBN: 9780124200371, 0124200370); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), Immunological Methods, Ivan Lefkovits, Benvenuto Pemis, (eds.) Elsevier Science, 2014 (ISBN: 9781483269993, 148326999X), the contents of which are all incorporated by reference herein in their entireties. As used in this specification and the appended claims, terms in the singular and the singular forms "a," "an" and "the," for example, optionally include plural referents unless the content clearly dictates otherwise. Thus, for example, reference to "a kidney organoid" optionally includes one or more kidney organoid.

As used herein, the term "about", unless stated to the contrary, refers to +/−10%, more preferably +/−5%, more preferably +/−1%, of the designated value.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

As used herein a "transplant composition" refers to a composition comprising an in vitro-differentiated cell or a population thereof. The composition can be formulated for administration to a subject as a transplant. Transplant compositions will comprise a pharmaceutically acceptable carrier, and can optionally comprise a matrix or scaffold for the cells. A transplant composition can be formulated for administration by injection or, for example, by surgical implantation.

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment of any of the aspects, the subject is a mammal. In another embodiment of any of the aspects, the subject is human. In another embodiment, of any of the aspects, the subject is an experimental animal or animal substitute as a disease model. In another embodiment, of any of the aspects, the subject is a domesticated animal including companion animals (e.g., dogs, cats, rats, pigs, guinea pigs, hamsters etc.). A subject can have previously received a treatment for a disease, or have never received treatment for a disease. A subject can have previously been diagnosed with having a disease, or have never been diagnosed with a disease.

The term "healthy subject" as used herein refers to a subject that, at a minimum, lacks markers or symptoms of the disease or disorder to be treated.

As used herein the term "human stem cell" refers to a human cell that can self-renew and differentiate to at least one different cell type. The term "human stem cell" encompasses human stem cell lines, human-derived induced pluripotent stem (iPS) cells, human embryonic stem cells, human pluripotent stem cells, human multipotent stem cells, amniotic stem cells, placental stem cells, or human adult stem cells. In one embodiment of any of the aspects, the human stem cell is not derived from a human embryo. "Induced pluripotent stem cells (iPSCs) or (iPS cells)" is a designation that pertains to somatic cells that have been reprogrammed or "de-differentiated", for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., *Cell Stem Cell*, 1:39-49 (2007)). For example, in one instance, to create iPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., PNAS, 105:5856-5861(2008); Jaenisch et al., *Cell*, 132: 567-582 (2008); Hanna et al., *Cell*, 133:250-264 (2008); and Brambrink et al., *Cell Stem Cell*, 2:151-159 (2008). It is also possible that such cells can be created by specific culture conditions (exposure to specific agents) may also be created from a variety of different starting cell types. These references are all incorporated by reference for teaching iPSCs and methods for producing them.

iPSCs have many characteristic features of embryonic stem cells. For example, they have the ability to create chimeras with germ line transmission and tetraploid complementation and they can also form teratomas containing various cell types from the three embryonic germ layers. On the other hand, they may not be identical as some reports demonstrate. See, for example, Chin et al., *Cell Stem Cell* 5:111-123 (2009) showing that induced pluripotent stem cells and embryonic stem cells can be distinguished by gene expression signatures.

Cells such as iPSCs or their progeny (including differentiated progeny) as disclosed herein may in the context of the present specification be said to "express" or "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a reference cell (e.g. negative control cell) or than an average signal generated for the marker by a population of reference or negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of reference or negative control cells.

Embodiments disclosed herein also relate to progeny of such iPSCs, including differentiated progeny or a population of cells obtained from one or more of the populations of barcoded iPSCs. As used herein, the term "differentiated" or "differentiation" as used with respect to cells in a differentiating cell system refers to the process by which cells differentiate from one cell type (e.g., a multipotent, totipotent or pluripotent differentiable cell) to another cell type such as a target differentiated cell). Accordingly, the "cell differentiation", refers to a specialization process or a pathway by which a less specialized cell (e.g. stem cell) develops or matures to possess a more distinct form and function (i.e. more specialized).

As used herein, "in vitro-differentiated cells" refers to cells that are generated in culture, typically via step-wise differentiation from a precursor cell such as an induced pluripotent stem cell, an early mesodermal, ectodermal, or endodermal cell, or a progenitor cell. Thus, for example, in vitro-differentiated cardiomyocytes" are cardiomyocytes that are generated in culture, typically via step-wise differentiation from a precursor cell such as a human embryonic stem cell, an induced pluripotent stem cell, an early mesoderm cell, a lateral plate mesoderm cell or a cardiac progenitor cell.

The term "derived from," used in reference to a stem cell means the stem cell was generated by reprogramming of a differentiated cell to a stem cell phenotype. The term "derived from," used in reference to a differentiated cell means the cell is the result of differentiation, e.g., in vitro-differentiation, of a stem cell. As one example, "iPSC-CMs" or "induced pluripotent stem cell-derived cardiomyocytes" are used interchangeably to refer to cardiomyocytes derived from an induced pluripotent stem cell by in vitro differentiation of the stem cell.

The term "agent" refers to any entity to be administered to or contacted with a cell, tissue, organ or subject which is normally not present or not present at the levels being administered to the cell, tissue, organ, or subject. Agents can be selected from a group comprising: chemicals; small molecules; nucleic acids; nucleic acid analogues; proteins; peptides; peptidomimetics; peptide derivatives; peptide analogs; aptamers; antibodies; intrabodies; biological macromolecules; or functional fragments thereof. A nucleic acid can be RNA or DNA, and can be single or double stranded, and can include, for example, nucleic acids encoding a protein of interest, as well as nucleic acids such as RNA interference or small interfering RNA molecules, antisense RNA molecules, or aptamers that inhibit gene expression or protein function. Nucleic acids can include oligonucleotides, as well as nucleic acid analogues, for example, peptide-nucleic acid (PNA), pseudo-complementary PNA (pc-PNA), and locked nucleic acid (LNA), etc.

Nucleic acids can include sequence encoding proteins, for example, that act as transcriptional repressors, as well as sequence encoding antisense molecules, ribozymes, small inhibitory nucleic acids, for example, but not limited to RNAi, shRNAi, siRNA, micro RNAi (mRNAi), antisense oligonucleotides, etc. A protein and/or peptide or fragment thereof can be any protein of interest, for example, but not limited to; mutated proteins, therapeutic proteins, or truncated proteins, including, e.g., dominant negative mutant proteins, wherein the protein is normally absent or expressed at lower levels in the cell. Proteins can also include mutated proteins, genetically engineered proteins, recombinant proteins, chimeric proteins, antibodies, midibodies, tribodies, humanized proteins, humanized antibodies, chimeric antibodies, modified proteins and fragments thereof. An agent can be applied or introduced to cell culture medium, where it contacts the cell and induces its effects. Alternatively, an agent can be intracellular as a result of introduction of a nucleic acid encoding the agent into the cell and its transcription resulting in the production of the nucleic acid and/or protein agent within the cell. In some embodiments, the agent is any chemical, entity or moiety, including without limitation synthetic and naturally-occurring non-proteinaceous entities. In certain embodiments the agent is a small molecule. Small molecules can include chemical moieties including unsubstituted or substituted alkyl, aromatic, or heterocyclyl moieties including macrolides, leptomycins and related natural products or analogues thereof. In some embodiments, agents can be extracts made from biological materials such as bacteria, plants, fungi, or animal cells or tissues. In some embodiments, agents can be naturally occurring or synthetic compositions or functional fragments thereof. Agents can be known to have a desired activity and/or property, or can be selected from a library of diverse compounds.

The phrase "pharmaceutically acceptable" is employed herein to refer to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "administering" is used in the context of the placement of an agent (e.g. a small molecule) described herein, on or into a cell, tissue, organ or a subject, by a method or route which results in at least partial localization of the agent at a desired site, e.g., in vitro differentiated cells, the heart, kidney, blood, skin, or a region thereof, such that a desired effect(s) is produced (e.g., decreased ASIC1a level or activity). The agent described herein can be administered by any appropriate route which results in delivery to a desired location in the subject. The half-life of the agent after administration to a subject can be as short as a few minutes, hours, or days, e.g., twenty-four hours, to a few days, to as long as several years, i.e., long-term. "Administering" can also refer to the placement of in vitro differentiated cells, treated with an agent as described herein, into a tissue, organ or subject. In this context, "administering" is equivalent to "transplanting."

As used herein, the term "transplanting" is used in the context of the placement of cells, e.g. in vitro-differentiated cells as described herein, into a subject, by a method or route which results in at least partial localization of the introduced cells at a desired site, such as a site of injury or repair, such that a desired effect(s) is produced. In some embodiments, the cells, e.g., cardiomyocytes, can be implanted or injected directly into or on the organ, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years or more, i.e., long-term engraftment. As one of skill in the art will appreciate, long-term engraftment of the in vitro-differentiated cells is desired, as many mature adult cells (e.g., cardiomyocytes) do not proliferate to an extent that the organ (e.g., heart) can heal from an acute injury involving cell death.

In various aspects, the cardiomyocytes may be implanted in the culture medium in which they are differentiated. In other aspects, the cardiomyocytes may be isolated from the culture medium, and implanted. In further aspects, a pharmaceutically acceptable scaffold, as are known in the art, for the cardiomyocytes is implanted in the patient at the site at which the cardiomyocytes are implanted. Any suitable scaffold material may be used, including porous or semi-porous, natural, synthetic or semi-synthetic materials. As referred to herein, a "scaffold" is a material that contains or supports the cardiomyocytes, preferably enabling their growth at the site of implantation. The scaffold material may be implanted either before, after, or concurrent with implantation of the cardiomyocytes.

In certain aspects, the present disclosure provides methods of tissue-engineered constructs comprising differentiated cardiomyocytes derived from the iPSCs disclosed herein. More specifically, the inventive methods and compositions may comprise contacting an appropriate substrate with the iPSCs disclosed herein to form a cell-seeded construct, and cultivating the resulting cell-seeded construct under appropriate conditions e.g. in in the presence of a regimen of growth factors or biomimetic electrical stimulation or electrical stimulation, to form differentiated cardiomyocytes in a tissue-engineered construct. The cultivation is carried out under conditions and for a time period that allow the formation of a three-dimensional cell structure having structural and functional characteristics of tissue.

A "treatment" of a disorder or a disease, (e.g., a cardiovascular disease) as referred to herein refers to therapeutic intervention that enhances the function of a cell, tissue, or organ, and/or enhances engraftment, and/or enhances transplant or graft vascularization in a treated area, thus improving the function of the tissue or organ, as non-limiting example, the heart. That is, a "treatment" is oriented to the function of the tissue or organ being treated (e.g., enhanced function within an infarcted area of the heart), and/or other site treated with the compositions described herein. Effective treatment need not cure or directly impact the underlying cause of the disease or disorder to be considered effective treatment. For example, a therapeutic approach that improves the function of the heart, e.g., in terms of contractile strength, or rhythm can be effective treatment without necessarily treating the cause of an infarction or arrhythmia.

As used herein, the terms "disease" or "disorder" refers to a disease, syndrome, or disorder, partially or completely, directly or indirectly, caused by one or more abnormalities in the genome, physiology, behavior, or health of a subject. The disease or disorder can be a cardiac disease or disorder or a cardiovascular disease or disorder. Non-limiting examples of cardiac diseases include cardiomyopathy, cardiac arrhythmia, heart failure, arrhythmogenic right ventricular dysplasia (ARVD), long QT syndrome, catecholaminergic polymorphic ventricular tachycardia (CPVT), Barth syndrome, and cardiac involvement in Duchenne muscular dystrophy.

As used herein, "prevention" or "preventing," when used in reference to a disease, disorder or symptoms thereof, refers to a reduction in the likelihood that an individual will develop a disease or disorder, e.g., heart failure following myocardial infarction, as but one example. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

The terms "decrease", "reduced", "reduction", "to a lesser extent," or "inhibit" are all used herein to mean a decrease or lessening of a property, level, or other parameter by a statistically significant amount. In some embodiments, "reduced," "reduction," "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "increases", or "enhance" or "activate" or "to a greater extent" are all used herein to generally mean an increase of a property, level, or other parameter by a statistically significant amount; for the avoidance of any doubt, the terms "increased", "increase", "to a greater extent," "enhance" or "activate" can refer to an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, a "reference level" refers to the level of a marker or parameter in a normal, otherwise unaffected cell population or tissue (e.g., a cell, tissue, or biological sample obtained from a healthy subject, or a biological sample obtained from the subject at a prior time point, e.g., cell, tissue, or a biological sample obtained from a patient prior to being diagnosed with a disease, or a biological sample that has not been contacted with an agent or composition as disclosed herein). Alternatively, a reference level can also refer to the level of a given marker or parameter in a subject, organ, tissue, or cell, prior to administration of a treatment, e.g., with an agent or via administration of a transplant composition.

As used herein, an "appropriate control" refers to an untreated, otherwise identical cell, subject, organism, or population (e.g., a cell, tissue, or biological sample that was not contacted by an agent or composition described herein) relative to a cell, tissue, biological sample, or population contacted or treated with a given treatment. For example, an appropriate control can be a cell, tissue, organ or subject that has not been contacted with an agent or administered a cell as described herein.

Any example or embodiment herein shall be taken to apply mutatis mutandis to any other example or embodiment unless specifically stated otherwise.

The present disclosure is not to be limited in scope by the specific examples described herein, which are intended for the purpose of exemplification only. Functionally-equivalent methods and systems are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The disclosure is hereinafter described by way of the following non-limiting Examples and with reference to the accompanying drawings. Although the examples herein concern humans and the language is primarily directed to human concerns, the concepts described herein are applicable to genomes from other animals. These and other objects and features of the present disclosure will become more fully apparent from the following description and appended claims, or may be learned by the practice of the disclosure as set forth hereinafter.

A reference herein to a patent document or other matter which is given as prior art is not to be taken as an admission that that document or matter was known or that the information it contains was part of the common general knowledge as at the priority date of any of the claims.

Compositions:

Acid sensing ion channels (ASICs) are voltage-independent proton-gated cation channels of the degenerin/epithelial sodium channel superfamily. There are six ASIC isoforms derived from four genes (ACCN1-4), which assemble into homotrimeric or heterotrimeric channels. The pH sensitivity and kinetics of ASICs are determined by their subunit composition. ASICs are involved in extracellular acidification-induced calcium overload in neurons and cardiomyocytes. ASIC1a, a splice variant of the ACCN1 gene, is the most pH-sensitive ASIC channel. Activation begins at pH≤7, with half-maximal activation at pH 6.6(35, 36), and ASIC1a currents are potentiated by numerous metabolic events that occur during ischemia, including membrane stretch and increased levels of extracellular lactate, pyruvate, and arachidonic acid. The inventors have surprisingly found that genetic ablation of ASIC1a had no impact on cardiac ion channels regulating baseline electromechanical coupling and physiological performance but lead to improved functional recovery following myocardial ischemic reperfusion injury, an effect that can be recapitulated by therapeutic blockade of ASIC1a using specific and potent pharmacological inhibitors.

Thus, described herein are methods of promoting survival and/or engraftment of transplanted mesoderm lineage cells, the method comprising: administering to a subject in need thereof mesoderm lineage cells that have been to genetically modified so as to lack, or have decreased or [[disrupted]] expression and/or activity of ASIC1a. In one embodiment the cells are ASIC1a−/−.

In certain embodiments, the cells are in vitro-differentiated cells, including but not limited to in vitro differentiated cardiomyocytes, among others. In addition to methods for transplanting cells that have been to genetically modified so as to lack, or have decreased or disrupted expression and/or activity of ASIC1a and for promoting survival of such cells, the invention described herein includes compositions comprising cells that have been genetically modified. In addition to methods for transplanting cells that have been to genetically modified so as to lack, or have decreased or disrupted expression and/or activity of ASIC1a, also described herein are in vitro-differentiated cell compositions in admixture with an agent that decreases the level or activity of ASIC1a.

The following describes considerations relevant to the practice of the technology described.

Cell Preparations:

In certain embodiments, the compositions and methods described herein use in vitro-differentiated cells. Such cells can be differentiated from induced pluripotent stem cells (iPSCs).

The following describes various sources and stem cells that can be used to prepare cells for transplant or engraftment into a subject.

Stem cells are cells that retain the ability to renew themselves through mitotic cell division and can differentiate into more specialized cell types. Cells useful in the compositions and methods described herein can be differentiated from iPSCs, among others.

Induced Pluripotent Stem Cells (iPSCs): In some embodiments, the compositions and methods described herein utilize human cardiomyocytes or other human mesodermal or ectodermal lineage cells that are differentiated in vitro iPSCs. An advantage of using iPSCs to generate cells for the compositions and methods described herein is that, if so desired, the cells can be derived from the same subject to which the differentiated cells are to be administered. That is, a somatic cell can be obtained from a subject, reprogrammed to an induced pluripotent stem cell, and then re-differentiated into a human cardiomyocyte or other mesodermal lineage cell to be administered to the subject (i.e., autologous cells). The use of such cells and their differentiated progeny are essentially derived from an autologous source, which reduces the risk of engraftment rejection or allergic responses compared to the use of cells from allogeneic sources (i.e. another subject or group of subjects). While this is an advantage of iPS cells, in alternative embodiments, the cardiomyocytes and other human mesodermal lineage cells useful for the methods and compositions described herein are derived from non-autologous sources (i.e., allogenic cells). Under such circumstances, iPSCs or their differentiated progeny which are HLA matched to the subject to be treated may be utilised and administered. Accordingly, in one embodiment, iPSCs, including iPSCs which have been genetically modified to lack, or have decreased or disrupted expression and/or activity of ASIC1a, or progeny of such cells, are HLA matched to the subject to be treated. In one embodiment the iPSCs or progeny cells are selected from a bank of HLA typed iPSCs.

Although differentiation is generally irreversible under physiological contexts, several methods have been developed in recent years to reprogram somatic cells to induced pluripotent stem cells. Exemplary methods are known to those of skill in the art and are described in the definitions section above.

The cell to be reprogrammed can be either partially or terminally differentiated prior to reprogramming. Thus, cells to be reprogrammed can be terminally differentiated somatic cells, as well as adult or somatic stem cells.

In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell to an undifferentiated state (e.g., an embryonic-like cell). Reprogramming can result in expression of particular genes by the cells, the expression of which further contributes to reprogramming. In certain embodiments described herein, reprogramming of a differentiated cell causes the differentiated cell to assume an undifferentiated state with the capacity for self-renewal and differentiation to cells of all three germ layer lineages. These are induced pluripotent stem cells (iPSCs or iPS cells).

Methods of reprogramming somatic cells into iPS cells are also described, for example, in U.S. Pat. Nos. 8,129,187 B2; 8,058,065 B2; US Patent Application 2012/0021519 A1; Singh et al. Front. Cell Dev. Biol. (February, 2015); and Park et al, Nature 451:141-146 (2008); which are incorporated by reference in their entireties.

The specific approach or method used to generate pluripotent stem cells from somatic cells (e.g., any cell of the body with the exclusion of a germ line cell; fibroblasts, etc.) is not critical to the claimed invention. Thus, any method that re-programs a somatic cell to the pluripotent phenotype would be appropriate for use in the methods described herein.

Adult Stem Cells: Adult stem cells are stem cells derived from tissues of a post-natal or post-neonatal organism or from an adult organism. An adult stem cell is structurally distinct from a pluripotent stem cell (e.g. an embryonic stem cell or iPSC) not only in markers it does or does not express relative to the pluripotent stem cell, but also by the presence of epigenetic differences, e.g. differences in DNA methylation patterns. It is contemplated that cardiomyocytes and/or neurons differentiated from adult stem cells can also be used for the methods described herein. Methods of isolating adult stem cells are described for example, in U.S. Pat. No. 9,206,393 B2; and US Application No. 2010/0166714 A1; which are incorporated herein by reference in their entireties.

In Vitro-Differentiation

Certain methods and compositions as described herein use mesodermal lineage cells differentiated in vitro from stem cells. Generally, throughout the differentiation process, a pluripotent cell will follow a developmental pathway along a particular developmental lineage, e.g., the primary germ layers—ectoderm, mesoderm, or endoderm.

The embryonic germ layers are the source from which all tissues and organs derive. The mesoderm is the source of, for example, smooth and striated muscle, including cardiac muscle, connective tissue, vessels, the cardiovascular system, blood cells, bone marrow, skeleton, reproductive organs and excretory organs.

The germ layers can be identified by the expression of specific biomarkers and gene expression. Assays to detect these biomarkers include, e.g., RT-PCR, immunohistochemistry, and Western blotting. Non-limiting examples of biomarkers expressed by early mesodermal cells include HAND1, ESM1, HAND2, HOPX, BMP10, FCN3, KDR, PDGFR-a, CD34, Tbx-6, Snail-1, Mesp-1, and GSC, among others. Biomarkers expressed by early ectoderm cells include but are not limited to TRPM8, POU4F1, OFFM3, WNT1, FMX1A and CDH9, among others. Biomarkers expressed by early endoderm cells include but are not limited to FEFTY1, EOMES, NODAF and FOXA2, among others. One of skill in the art can determine which lineage markers to monitor while performing a differentiation protocol based on the cell type and the germ layer from which that cell is derived in development.

Induction of a particular developmental lineage in vitro is accomplished by culturing stem cells in the presence of specific agents or combinations thereof that promote lineage commitment. Generally, the methods described herein comprise the step-wise addition of agents (e.g., small molecules, growth factors, cytokines, polypeptides, vectors, etc.) into the cell culture medium or contacting a cell with agents that promote differentiation. In particular, mesoderm formation is induced by transcription factors and growth factor signalling which includes but is not limited to VEGF, Wnt signalling (e.g., via b-catenin), bone morphogenic protein (BMP) pathways, fibroblast growth factor (FGF) pathways, and TGF signalling (e.g., activin A). See e.g., Clemens el al. Cell Mol Life Sci. (2016), which is incorporated herein by reference in its entirety.

In the context of cell ontogeny, the term "differentiate", or "differentiating" is a relative term meaning a "differentiated cell" is a cell that has progressed further down the developmental pathway than its precursor cell. Thus, in some embodiments, a reprogrammed cell can differentiate to lineage-restricted precursor cells (such as a mesodermal stem cell), which in turn can differentiate into other types of precursor cells further down the pathway (such as a tissue specific precursor, e.g., a cardiomyocyte precursor), and then to an end-stage differentiated cell, which plays a characteristic role in a certain tissue type, and may or may not retain the capacity to proliferate further.

Generally, in vitro-differentiated cells will exhibit a down-regulation of pluripotency markers (e.g., HNF4-a, AFP, GATA-4, and GATA-6) throughout the step-wise process and exhibit an increase in expression of lineage-specific biomarkers (e.g., mesodermal, ectodermal, or endodermal markers). See for example, Tsankov et al. Nature Biotech (2015), which describes the characterization of human pluripotent stem cell lines and differentiation along a particular lineage. The differentiation process can be monitored for efficiency by a number of methods known in the art. This includes detecting the presence of germ layer biomarkers using standard techniques, e.g., immunocytochemistry, RT-PCR, flow cytometry, functional assays, optical tracking, etc.

In some embodiments of any of the aspects, the in vitro-differentiated cells are of a mesodermal lineage cell type selected from: cardiomyocytes, skeletal muscle cells, smooth muscle cells, kidney cells, liver cells, endothelial cells, skin cells, adrenal cortex cells, bone cells, white blood cells, and microglial cells.

Cardiomyocyte Differentiation:

In some embodiments of the methods and compositions described herein, the cells differentiated in vitro from stem cells are cardiomyocytes. Methods for the differentiation of cardiomyocytes from iPSCs are known in the art. In some embodiments of any of the aspects, the cardiomyocytes are differentiated from iPSCs derived from the transplant recipient, e.g., as described herein or as known in the art.

In certain embodiments, the step-wise differentiation of iPSCs to cardiomyocytes proceeds in the following order: iPSC>cardiogenic mesoderm>cardiac progenitor cells>cardiomyocytes (see e.g., Lian et al. Nat Prot (2013); US Applicant No. 2017/0058263 Al; 2008/0089874 Al; 2006/0040389 Al; U.S. Pat. Nos. 10,155,927 B2; 9,994,812 B2; and 9,663,764 B2, the contents of each of which are incorporated herein by reference their entireties). See also, e.g., LaFlamme el al, Nature Biotech 25: 1015-1024 (2007), and Friedman et al., Cell Stem Cell 23, 586-598.e588 (2018), which are incorporated herein by reference in their entireties. In these differentiation protocols, agents can be added or removed from cell culture media to direct differentiation to cardiomyocytes in a step-wise fashion. Non-limiting examples of factors and agents that can promote cardiomyocyte differentiation include small molecules (e.g., Wnt inhibitors, GSK3 inhibitors), polypeptides (e.g., growth factors), nucleic acids, vectors, and patterned substrates (e.g., nanopatterns). The addition of growth factors necessary in cardiovascular development, including but not limited to fibroblast growth factor 2 (FGF2), transforming growth factor b (TGF) superfamily growth factors Activin A and BMP4, vascular endothelial growth factor (VEGF), and the Wnt inhibitor DKK-1, can also be beneficial in directing differentiation along the cardiac lineage. Additional examples of factors and conditions that help promote cardiomyocyte differentiation include but are not limited to B27™ supplement lacking insulin, cell-conditioned media, and external electrical pacing.

In one embodiment, contractile cardiomyocytes are differentiated using a high-density monolayer format as described by Friedman et al. Cell Stem Cell 23, 586-598.e588 (2018). Briefly, hiPSCs are dissociated and single-cell suspensions are and cultured overnight in mTeSR™ medium supplemented with 10 µM Y-27632 dihydrochloride. Once the monolayer reach approximately 80% confluence (usually the following day), differentiation is induced (day 0). The cells are quickly washed with PBS followed by a change in medium to RPMI medium containing 3 µM CHIR99021, 500 µg/mL BSA and 213 µg/mL ascorbic acid. After 3 days of culture, the medium is exchanged to RPMI containing 500 µg/mL BSA, 213 µg/mL ascorbic acid, and 5 µM Xav-939. On day 5, the medium is replaced with RPMI containing BSA and ascorbic acid as on day 3. Starting on day 7, the cells are fed every other day with RPMI containing 1×B27™ supplement with insulin. Spontaneous beating is then typically observed between days 9 and 11 of differentiation.

Generally, cells being differentiated into cardiomyocytes will begin to beat and contract in culture about 12 days after the addition of activin A. This can be monitored using standard cell culture and microscopy techniques.

In addition to in vitro-differentiated cardiomyocyte functional readouts (e.g., beating, contractile cells), the in vitro-differentiated cardiomyocytes will also express biomarkers specific to adult cardiac cells. Non-limiting examples of cardiomyocyte biomarkers include cardiac troponin T (cTnT), a-actinin, or myosin heavy chain. While additional protein markers, and, e.g., functional hallmarks of cardiomyocyte maturity are preferred to be present, at a minimum in vitro-differentiated human cardiomyocytes useful in the methods and compositions described herein will express cardiac troponin T. If necessary or desired, the cardiomyocytes can then be enriched for using a Percoll gradient or a cell sorting technique (e.g., flow cytometry) for cardiomyocyte biomarkers (e.g., troponin T, a-actinin, myosin heavy chain, or ryanodine receptor 2). Examples of cardiomyocyte enrichment are found, e.g., in Xu et al. Circ Res. (2002); Laflamme et al. Am. J. Pathol. 167, 663-671 (2005); and Miltenyi Biotec MACS® Characterization by flow cytometry PSC-derived cardiomyocyte subtypes (2017); which are incorporated herein by reference in their entireties.

In vitro-differentiated cardiomyocyte maturity can be assessed by a number of parameters such as electrical maturity of a cell, metabolic maturity of a cell, or contractile maturity of an in vitro-differentiated cell. Examples of cardiomyocyte maturity proteins, biochemical, and electrical maturity markers are found, e.g., in WO2019/035032 A2, which is incorporated herein by reference in its entirety.

Non-limiting examples of such methods to determine electrical maturity of a cell include whole cell patch clamp (manual or automated), multielectrode arrays, field potential stimulation, calcium imaging and optical mapping, among others. Cells can be electrically stimulated during whole cell current clamp or field potential recordings to produce an electrical and/or contractile response. Measurement of field potentials and biopotentials of cardiomyocytes can be used to determine the differentiation stage and cell maturity.

With regard to cardiomyocytes, electrical maturity is determined by one or more of the following markers as compared to a reference level: increased gene expression of one or more ion channel genes, increased sodium current density, increased inwardly-rectifying potassium channel current density, increased action potential frequency, increased calcium wave frequency, and increased field potential frequency. Methods of measuring gene expression are known in the art, e.g., RT-PCR and transcriptomic sequencing.

Metabolic assays can be used to determine the differentiation stage and cell maturity of the in vitro-differentiated cells as described herein. Non-limiting examples of metabolic assays include cellular bioenergetics assays (e.g., Seahorse Bioscience XF Extracellular Flux Analyzer), and oxygen consumption tests. Specifically, cellular metabolism can be quantified by oxygen consumption rate (OCR), OCR trace during a fatty acid stress test, maximum change in OCR, maximum change in OCR after FCCP addition, and maximum respiratory capacity among other parameters. Furthermore, a metabolic challenge or lactate enrichment assay can provide a measure of cellular maturity or a measure of the effects of various treatments of such cells For example, metabolic maturity of in vitro-differentiated cardiomyocytes is determined by one or more of the following markers as compared to a reference level: increased activity of mitochondrial function, increased fatty acid metabolism, increased oxygen consumption rate (OCR), increased phosphorylated ACC levels or activity, increased level or activity of fatty acid binding protein (FABP), increased level or activity of pyruvate dehydrogenase kinase-4 (PDK4), increased mitochondrial respiratory capacity, increased mitochondrial volume, and increased levels of mitochondrial DNA relative to immature in vitro-differentiated cardiomyocytes. Mammalian cells generally use glucose as their main energy source. However, cardiomyocytes are capable of energy production from different sources such as lactate or fatty acids. In some embodiments, lactate-supplemented and glucose-depleted culture medium, or the ability of cells to use lactate or fatty acids as an energy source is useful to identify mature cardiomyocytes and variations in their function.

Contractile maturity of an in vitro-differentiated cell (e.g. cardiomyocytes, skeletal muscle, or smooth muscle) is determined by one or more of the following markers as compared to a reference level: increased beat frequency, increased contractile force, increased level or activity of a-myosin heavy chain (a-MHC), increased level or activity of sarcomeres, decreased circularity index, increased level or activity of troponin, increased level or activity of titin N2b, increased cell area, and increased aspect ratio. Contractility can be measured by optical tracking methods such as video analysis. For video tracking methods, displacement of tissues or single cells can be measured to determine contractile force, frequency, etc.

Additional Cell Types:

The methods and compositions described herein also use or are applicable to in vitro-differentiated mesodermal lineage cells including, skeletal muscle cells, smooth muscle cells, kidney cells, endothelial cells, skin cells, adrenal cortex cells, bone cells, white blood cells, and microglial cells.

Methods of differentiating stem cell-derived skeletal muscle cells, smooth muscle, and/or adipose cells are described, e.g., in U.S. Pat. No. 10,240,123 B2; and Cheng et al. Am J Physiol Cell Physiol (2014). Methods of differentiating kidney cells are described, e.g., in Tajiri el al. Scientific Reports 8: 14919 (2018); Taguchi et al. Cell Stem Cell 14:53-67 (2014); and US application 2010/0021438 Al. Methods of differentiating endothelial cells (e.g., vascular endothelium) are described in, e.g., U.S. Pat. No. 10,344,262 B2, and Olgasi et al., Stem Cell Reports 11:1391-1406 (2018). Methods of differentiating hormone-producing cells are described, e.g., in U.S. Pat. No. 7,879,603 B2, and Abu-Bonsrah etal. Stem Cell Reports 10: 134-150 (2018). Methods of differentiating bone cells are described, e.g., in Csobonyeiova et al. J Adv Res 8: 321-327 (2017), U.S. Pat. Nos. 7,498,170 B2; 6,391,297 Bl; and US application No. 2010/0015164 Al. Methods of differentiating microglial cells are described, e.g., in WO 2017/152081 Al. Methods of differentiating epithelial cells and skin cells are described, e.g., in Kim et al, Stem Cell Research and Therapy (2018); U.S. Pat. Nos. 7,794,742 B2; 6,902,881 B2. Methods of differentiating blood cells and white blood cells are described, e.g., in U.S. Pat. Nos. 6,010,696 A and 6,743,634 B2. Methods of differentiating stem cell-derived beta cells are described, e.g., in WO 2016/100930A1. Each of the above references are incorporated herein by reference in their entireties.

Methods of Enriching for Specific Cell Types:

The stem cells, progenitor cells, and/or in vitro-differentiated cells described herein can be cultured on a mouse embryonic fibroblast (MEF) feeder layer of cells, Matrigel®, collagenase IV, or any other matrix or scaffold that substantially promotes in-vitro differentiation of the desired cell type and/or maintains a mature, viable, phenotype of the desired cell. In some embodiments, antibodies or similar agents specific for a given marker, or set of markers, can be used to separate and isolate the desired cells using fluorescent activated cell sorting (FACS), panning methods, magnetic particle selection, particle sorter selection and other methods known to persons skilled in the art, including density separation (Xu etal. (2002) Circ. Res. 91:501; U.S.S.N. 20030022367) and separation based on other physical properties (Doevendans el al. (2000) J. Mol. Cell. Cardiol. 32:839-851). Negative selection can be performed, including selecting and removing cells with undesired markers or characteristics, for example fibroblast markers, epithelial cell markers etc.

Undifferentiated iPSCs express genes that can be used as markers to detect the presence of undifferentiated cells. Exemplary iPSC cell markers include stage-specific embryonic antigen (SSEA)-3, SSEA-4, TRA-I-60, TRA-1-81, or alkaline phosphatase. Exemplary markers expressed on cardiac progenitor cells include, but are not limited to, TMEM88, GATA4, ISL1, MYL4, and NKX2-5. Such markers can be assessed or used to remove or determine the presence of undifferentiated or progenitor cells in, e.g., a population of in vitro-differentiated cardiomyocytes. Similarly, the presence of markers of undifferentiated cells, whether pluripotency markers or otherwise, can be used to evaluate populations of other mesoderm lineage cell types useful in the methods and compositions described herein.

Gene Editing:

The skilled person is aware of a variety of means for genetic engineering in which DNA of a cell may be inserted, deleted, modified or replaced, such as through the use of targeted nuclease. Clustered regularly interspaced short palindromic repeats (CRISPR)-CRISPR-associated protein 9 (Cas9), transcription activator-like effector nucleases (TAL-ENs), and zinc-finger nucleases (ZFNs) represent three foundational technologies which may be employed in this respect to produce genetically modified iPSCs or progeny thereof as described herein. In one embodiment of the genetically modified iPSCs are produced using CRISPR-cas9.

Agents that Reduce the Levels and/or Activity of ASIC1a

In certain embodiments, methods and compositions described herein include the use of an agent or agents that inhibit or decrease the level or activity of ASIC1a in cells or cell preparations for transplant, e.g., in vitro-differentiated cells for transplant.

The levels of ASIC1a can be determined by methods known in the art, for example, immunoprecipitation or other pull-down assays, western blotting, qPCR, RT-PCR, and immunocytochemistry. Thus, these methods can be used to determine whether a given treatment or agent decreases the level of ASIC1a protein, mRNA, or both. Primers for RT-PCR can be prepared on the basis of the mRNA sequence, e.g., based on NM_001095.4: SEQ ID NO: 1.

In some embodiments, an agent decreases the activity of ASIC1a. In some embodiments the agent decreases the activity of ASIC1a by at least 20%, at least 30%, at least 40%, at least 50%, at least 60%, at least 70%, at least 80%, at least 90%, or more as compared to an appropriate control.

The activity of ASIC1a can be determined by any method known in the art, including the methods described hereinabove for determining electrical maturity and assessment of electrophysiology using patch clamp techniques described in the examples herein.

In one embodiment, the effect of an agent that decreases ASIC1a activity can be confirmed by contacting in vitro-differentiated cells, e.g., cells of a mesodermal lineage, e.g., in vitro-differentiated cardiomyocytes, with the agent and transplanting the cells into an appropriate animal model. An agent that promotes or further enhances survival of the transplanted cells relative to untreated cells is then confirmed to be an agent that decreases ASIC1a activity.

In some embodiments of any of the aspects, the agent is a small molecule, a polypeptide, an antibody, a nucleic acid molecule, an RNAi, a vector comprising a nucleic acid molecule, an antisense oligonucleotide, or a gene editing system (e.g. CRISPR/Cas9).

In some embodiments, an agent decreases the level of ASIC1a. In some embodiments the agent decreases the level of ASIC1a by at least 20%, at least 30%, at least 40%, at least 50%, at least 60%, at least 70%, at least 80%, at least 90%, or more as compared to an appropriate control.

In some embodiments, the agent that decreases the level or activity of ASIC1a is a small molecule. A small molecule is an organic or inorganic molecule, which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, and salts, esters, and other pharmaceutically acceptable forms of such compounds. Examples of "small molecules" include, but are not limited to, compounds described in Goodman and Gillman's The Pharmacological Basis of Therapeutics" 13 ed. (2018); incorporated herein by reference. Methods for screening small molecules are known in the art and can be used to identify a small molecule that is efficient at, for example, modulating ASIC1a levels or activity, given the desired target (e.g, ASIC1a polypeptide).

In preferred embodiments, the agent that decreases the level or activity of ASIC1a is selected from Hi1a and PcTx1. In a preferred embodiment the agent that decreases the level or activity of ASIC1a is Hi1a. Hi1a is a 76-residue double-knot peptide isolated from the venom of an Australian funnel-web spider; it is the most potent and selective inhibitor of ASIC1a identified to date, with an IC50 on rat and human ASIC1a of ~500 pM (I. R. Chassagnon et al., *Proc. Natl. Acad. Sci. U.S.A.* 114, 3750-3755 (2017)). PcTx1, a single-knot peptide from the venom of a tarantula, is also a potent and selective inhibitor of ASIC1a (IC50 ~1 nM) (C. A. McCarthy et al., *Neuropharmacology* 99, 650-657 (2015)).

In some embodiments of any of the aspects, the agent that decreases the level or activity of ASIC1a comprises or encodes a nucleic acid molecule comprising an antisense sequence, an aptamer or an RNA interference molecule (RNAi) that targets ASIC1a or its RNA transcript.

In some embodiments, of any of the aspects, the inhibitory nucleic acid is an inhibitory RNA or RNA interference molecule (iRNA).

RNAi, also referred to as interfering RNA (iRNA) is any of a class of agents that contain RNA (or modified nucleic acids as described, for example, herein below) and which mediates the targeted cleavage of an RNA transcript via a highly conserved RNA-induced silencing complex (RISC) pathway. An iRNA for use as the agent that decreases the level or activity of ASIC1a effects inhibition of the expression and/or activity of ASIC1a and contacting a cell with the iRNA results in a decrease in the target mRNA level in a cell by at least about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. In one embodiment, the iRNA can be or include a single strand of RNA that folds back on itself through self complementarity to form a base-paired duplex that targets a transcript of interest. These are referred to as short hairpin RNAs or shRNAs, and can, if so desired, be encoded by a construct introduced to a cell. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e. cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length, as noted above.

Exemplary embodiments of types of inhibitory nucleic acids can include, e.g., siRNA, shRNA, and/or miRNA, which are known in the art. One of ordinary skill in the art can design and test an RNAi agent that targets ASIC1a mRNA. Publicly available RNAi design software permits one of skill in the art to select one or more sequences within a given target transcript that is or are likely to mediate efficient knock-down of target gene expression, and there are commercial sources for both design and preparation of RNAi agents.

Preparation of the modified nucleic acids, backbones, and nucleobases described above are known in the art.

In one embodiment of any of the aspects, the agent that decreases ASIC1a is an antisense oligonucleotide, e.g., a nucleic acid with a sequence complementary to a target mRNA sequence. Antisense oligonucleotides are typically designed to block expression of a DNA or RNA target by hybridizing to the target and halting expression at the level of transcription, translation, or splicing. Antisense oligonucleotides as described herein are designed to hybridize to a target under typical intracellular conditions. Thus, oligonucleotides are chosen that are sufficiently complementary to the target, i.e., that hybridize sufficiently well and with sufficient specificity in the context of the cellular environment, to give the desired effect. For example, an antisense oligonucleotide that decreases the level of ASIC1a may comprise at least 10, at least 15, at least 20, at least 25, at least 30, or more bases complementary to a portion of the coding sequence of the human ASIC1a gene (e.g., SEQ ID NO: X), respectively.

In certain embodiments, a vector is useful to express an agent described herein that reduces the levels or activity of ASIC1a in the in vitro-differentiated cells described herein, including but not limited to one or more polypeptides, peptides, ribozymes, peptide nucleic acids, siRNAs, or RNAi molecules, including for example, antisense oligonucleotides, antisense polynucleotides, siRNAs, shRNAs, micro-RNAs, and their antisense counterparts (e.g., antagoMiR)), antibodies, antigen binding fragments, or any combination thereof.

A vector is a nucleic acid construct designed for delivery to a host cell or for transfer of genetic material between different host cells. As used herein, a vector can be viral or non-viral. The term "vector" encompasses any genetic element that is capable of replication when associated with the proper control elements and that can transfer genetic material to cells. A vector can include, but is not limited to, a cloning vector, an expression vector, a plasmid, phage, transposon, cosmid, artificial chromosome, virus, virion, etc.

In some embodiments of any of the aspects, the vector is selected from the group consisting of: a plasmid and a viral vector.

Integrating vectors have their delivered RNA/DNA permanently incorporated into the host cell chromosomes. Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector.

Non-integrative vectors include non-integrative viral vectors. Non-integrative viral vectors eliminate one of the primary risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. Containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free host cells. Other non-integrative viral vectors include adenoviral vectors and the adeno-associated viral (AAV) vectors.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages). This permits a self-limiting transient expression of a chosen heterologous gene or genes in a target cell.

Another example of a non-integrative vector is a minicircle vector. Minicircle vectors are circularized vectors in which the plasmid backbone has been released leaving only the eukaryotic promoter and cDNA(s) that are to be expressed.

As noted above, in some embodiments, the agent described herein is expressed in the cells from a viral vector. A "viral vector" includes a nucleic acid vector construct that includes at least one element of viral origin and has the capacity to be packaged into a viral vector particle. The viral vector can contain a nucleic acid encoding a polypeptide agent as described herein in place of non-essential viral genes. The vector and/or particle may be utilized for the purpose of transferring nucleic acids into cells either in vitro or in vivo.

In some embodiments, the nucleic acids and vectors described herein can be used to provide an antisense nucleic acid, a RNAi, an aptamer, or a vector comprising nucleic acids, to a cell in vitro or in vivo. The nucleic acids described herein can be delivered using any transfection reagent or other physical means that facilitates entry of nucleic acids into a cell. Methods and compositions for administering, delivering, or contacting a cell with a nucleic acid are known in the art, e.g., liposomes, nanoparticles, exosomes, nanocapsules, conjugates, alcohols, polylysine-rich compounds, arginine-rich compounds, calcium phosphate, microvesicles, microinjection and electroporation. An "agent that increases cellular uptake" is a molecule that facilitates transport of a molecule, e.g., nucleic acid, or peptide or polypeptide, or other molecule that does not otherwise efficiently transit the cell membrane across a lipid membrane. For example, a nucleic acid can be conjugated to a lipophilic compound (e.g., cholesterol, tocopherol, etc.), a cell penetrating peptide (CPP) (e.g., penetratin, TAT, Syn1B, etc.), or a polyamine (e.g., spermine). Further examples of agents that increase cellular uptake are disclosed, for example, in Winkler (2013). Oligonucleotide conjugates for therapeutic applications. Ther. Deliv. 4(7); 791-809.

Assays known in the art can be used to test the efficiency of nucleic acid delivery to an in vitro-differentiated cell or tissue. Efficiency of introduction can be assessed by one skilled in the art by measuring mRNA and/or protein levels of a desired transgene (e.g., via reverse transcription PCR, western blot analysis, and enzyme-linked immunosorbent assay (ELISA)). In some embodiments, a vector described herein comprises a reporter protein that can be used to assess the expression of the desired transgene, for example by examining the expression of the reporter protein by fluorescence microscopy or a luminescence plate reader.

In some embodiments, the agent that reduces the levels or activity of ASIC1a is a nucleic acid encoding a polypeptide or a vector encoding a polypeptide. A polypeptide can encompass a singular "polypeptide" as well as plural "polypeptides," and includes any chain or chains of two or more amino acids.

In some embodiments, the agent that reduces the levels or activity of ASIC1a is a dominant negative mutant of ASIC1a or ASIC1a comprising one or more point mutations.

Transplant Compositions

In one aspect, described herein is a method of promoting survival and/or engraftment of transplanted human, in vitro-differentiated cells, the method comprises contacting, human cells with an agent that decreases the level or activity of ASIC1a, and transplanting the cells or cells that are derived therefrom, e.g. in vitro-differentiated cells, into a tissue of a subject in need thereof. In some embodiments, the in-vitro differentiated cells are of a mesodermal lineage. In some embodiments, the in vitro-differentiated cells are cardiomyocytes. The in vitro-differentiated cells can be any of those described above, or other mesodermal lineage cells differentiated in vitro as known herein in the art.

For the treatment of cells with an agent that decreases the level or activity of ASIC1a, the formulation, dosage and timing of the treatment with the agent will vary with the nature of the agent. For example, a small molecule or other agent that crosses the cell's plasma membrane can simply be administered to the culture medium in which the cells are maintained, while a small molecule or other agent that does not readily cross the plasma membrane can be formulated with a moiety that facilitates delivery into the cell. The factors that determine whether a given agent will transit the plasma membrane on its own, e.g., by passive transport, or whether it will require formulation with another agent or entity that promotes or facilitates membrane transit are discussed, for example, in a review article "Getting Across the Cell Membrane: An Overview for Small Molecules, Peptides, and Proteins," by Yang & Hinner, Methods Mol. Biol. 1266: 29-53 (2015), which is incorporated herein by reference in its entirety. The authors note that small, nonpolar gases such as oxygen, carbon dioxide and nitrogen and small polar molecules such as ethanol readily cross membranes, but that even slightly larger metabolites such as urea and glycerol have lower permeability, and the plasma membrane is virtually impermeable to larger, uncharged polar molecules and all charged molecules, including ions. Thus, approaches that engage other mechanisms need to be considered for many peptides, polypeptides, oligo- or polynucleotides and many organic compounds and small molecules.

Many molecules, including sugars (glucose, galactose, fructose), amino acids and nucleotides are transported across the cell membrane by membrane transporter proteins. Conjugating an agent one wishes to transport across the membrane with a natural substrate for a transporter protein can be effective for delivery of some agents to the cytosol. See, e.g., Dahan el al, Expert Opin. Drug Deliv. 9: 1001-1013 (2012), and Majumdar et al, Adv. Drug Deliv. Rev. 56: 1437-1452 (2004), each of which is incorporated herein by reference.

Lipid and polymer-based formulations for delivery of an agent across the cell membrane include those that encapsulate the agent in liposomes or that complex the agent with lipids. Such approaches are well established for introducing nucleic acids (e.g., siRNAs, antisense oligonucleotides, ribozymes, aptamers, constructs encoding protein agents, shRNAs, antisense expression cassettes, aptamers etc.) to cells. Commercial preparations for lipofection are readily available, e.g., LIPOFECTAMINE™ (ThermoFisher Scientific) transfection reagents, among others. A mixture of cationic and neutral lipids has been reported to translocate negatively charged proteins (see, e.g., Zelphati et al, J. Biol. Chem. 276: 35103-35110 (2001) and Torchilin, Drug Discov. Today Technol. 5: e95-el03 (2008), each of which is incorporated herein by reference). Polymer-based formulations including polyethylenimine (PEI) and poly-P-amino ester nanoparticles enhance endosomal escape of cargos including proteins when administered to cells (see, e.g., Behr, Chim. Int. J. Chem. 51:34-36 (1997), and Su et al, Biomacromolecules 14: 1093-1102 (2013), each of which is incorporated herein by reference). Further examples of delivery formulations include but are not limited to multilamellar vesicles (MLV), unilamellar vesicles (UMVs), PEG-coated liposomes, exosomes, nanoparticles, and FuGENE® (Promega Corporation, Madison WI).

Any of these or other approaches or formulations known in the art can be applied to a given agent for introduction of an agent that decreases the level or activity of ASIC1a to in vitro-differentiated cells as described herein.

In the context of delivering an agent described herein, the term "contacting," "delivering" or "delivery" is intended to encompass both delivery of an agent that reduces the levels or activity of ASIC1a from outside the cell, and delivery from within the cell, e.g., by expression from a nucleic acid construct or vector or gene-editing system. For example, agents described herein can be introduced from outside the cell by adding the agent to the cell culture medium in which in vitro-differentiated cells as described herein are maintained or grown. Alternatively, the agents described herein can be delivered by expression within the cell from an exogenous construct, e.g., a viral or other expression vector. Such a construct can be episomal or stably integrated within the cell's genome. In one embodiment, the step of contacting an in vitro-differentiated mesodermal lineage cell or cardiomyocyte with an agent described herein comprises the use of cells that stably express the agent from a construct. In another embodiment, the step of contacting an in vitro-differentiated cell or cardiomyocyte with an agent described herein comprises the use of cells that transiently express the agent from a construct.

With respect to dosage, the amount to use of an agent that decreases the level or activity of ASIC1a will depend upon the nature of the agent and the formulation. Thus, agents that transit cell membranes without requiring conjugation or complex formation with another agent can be applied to cultured cells at picomolar to micromolar concentrations which can be optimized in a straightforward manner via a dose response titration. Agents that require conjugation or complex formation with another agent for transmembrane delivery can also be titrated over a range of concentrations for effective knockdown of ASIC1a mRNA, protein or activity. Once a working range that knocks down the level or activity of the ASIC1a is identified, in vivo experiments in which treated cells are injected or otherwise administered to, for example, an animal model can be used to identify the dosage that provides the best results for survival and/or engraftment.

With respect to timing, the duration of treatment of cells with a given agent or formulation and the timing of such treatment relative to the administration of the treated cells to the subject can also vary with the nature of the agent and the nature of the cells (e.g., cardiomyocytes vs kidney, bone or other mesodermal lineage cell type). However, one of ordinary skill in the art can determine for a given agent and formulation how long to treat the cells to achieve optimal ASIC1a inhibition or knockdown, and how far in advance of cell administration to the subject to initiate the treatment of the cells. In general, agents that take longer to achieve knockdown or inhibition should be administered earlier with respect to the planned time of cell administration. In some embodiments of any of the aspects, the in vitro-differentiated cells are contacted with an agent that decreases the levels or activity of ASIC1a in the range of 1-48 hours prior to administration of the cells to a subject, e.g., 1-36 hours, 1-24 hours, 1-18 hours, 1-12 hours, 1-6 hours, 1-4 hours or 1-2 hours before the cells are to be administered to a subject. In some embodiments of any of the aspects, the cells are contacted with the agent that decreases the levels or activity of ASIC1a at least 1 hour before, at least 2 hours before, at least 3 hours before, at least 4 hours before, at least 6 hours before, at least 8 hours before, at least 10 hours before, at least 12 hours before, at least 14 hours before, at least 16 hours before, at least 18 hours before, at least 24 hours before, at least 30 hours before, at least 36 hours before, at least 42 hours before, or at least 48 hours before the cells are administered to a subject.

Transplant compositions as described herein comprise in vitro-differentiated cells derived from stem cells which have been genetically modified to lack or have decreased expression and/or activity of ASIC1a, or otherwise treated with an agent that decreases the level or activity of ASIC1a, in those cells, in admixture with a pharmaceutically acceptable carrier. The transplant composition can be formulated, for example, for administration by injection to a tissue or organ in need of repair or functional augmentation.

The compositions may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like. This pharmaceutical composition can contain additional additives such as mannitol, dextran, sugar, glycine, lactose or polyvinylpyrrolidone or other additives such as antioxidants or inert gas, stabilizers or recombinant proteins (e. g. human serum albumin) suitable for in vivo administration.

As used herein, the term "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In one embodiment, the compositions may additionally comprise additional bioactive factors. Such additional factors include growth factors. Examples of growth factors include platelet derived growth factor (PDGF), transforming growth factor alpha or beta (TGFP), bone morphogenic protein 4 (BMP4), fibroblastic growth factor 7 (FGF7), fibroblast growth factor 10 (FGF10), epidermal growth factor (EGF/TGFP), vascular endothelium growth factor (VEGF), some of which are also angiogenic factors. These factors are known to those skilled in the art and are available commercially or described in the literature.

In another embodiment the transplant compositions may comprise one or more additional agents which promotes or enhances the survival of the cells of said composition when administered to a subject. In embodiments, the agent is an apoptosis inhibitor, and/or a necrosis inhibitor. Various apoptosis inhibitors are known in the art.

Alternatively, the transplant composition can be formulated on or in a scaffold as described herein or as known in the art, e.g., to assist with retaining the transplanted cells in a given physical location or to further augment survival and/or engraftment. Cells associated with a scaffold can also be formulated for injection, e.g., where the scaffold is a gel or other matrix with a fluid consistency. Alternatively, where the scaffold is more solid, cells associated with a scaffold can be formulated to apply to a tissue or organ or to implant surgically into or onto a tissue or organ.

For therapy, in vitro-cells prepared as described herein and exemplified herein and pharmaceutical compositions according to the invention may be administered via any appropriate route. The dose and the number of administrations can be optimized by those skilled in the art in a known manner. One of skill in the art can determine the number of cells needed for a transplant or graft depending, for example, upon the extent of damage to be repaired and the cell type. For example, in vitro-differentiated cardiomyocytes as described herein can be administered to a subject in need of improved cardiac function. In some embodiments, about 10 million to about 10 billion cardiomyocytes are administered to the subject. For use in the various aspects described herein, an effective amount of human cardiomyocytes can comprise at least $1 \times 10^6$, at least $2 \times 10^6$, at least $3 \times 10^6$, at least $4 \times 10^6$, at least $5 \times 10^6$, at least $6 \times 10^6$, at least $7 \times 10^6$, at least $8 \times 10^6$, at least $9 \times 10^6$, at least $1 \times 10^7$, at least $2 \times 10^7$, at least $3 \times 10^7$, at least $4 \times 10^7$, at least $5 \times 10^7$, at least $6 \times 10^7$, at least $7 \times 10^7$, at least $8 \times 10^7$, at least $9 \times 10^7$, at least $1 \times 10^8$, at least $2 \times 10^8$, at least $3 \times 10^8$, at least $4 \times 10^8$, at least $5 \times 10^8$, at least $6 \times 10^8$, at least $7 \times 10^8$, at least $8 \times 10^8$, at least $9 \times 10^8$, at least $1 \times 10^9$, at least $2 \times 10^9$, at least $3 \times 10^9$, at least $4 \times 10^9$, at least $5 \times 10^9$, at least $6 \times 10^9$, at least $7 \times 10^9$, at least $8 \times 10^9$, at least $9 \times 10^9$, at least $1 \times 10^9$, at least $1 \times 10^{10}$ or more cells for transplant or graft. Similar numbers of other in vitro-differentiated mesoderm lineage cells can be used for transplant or graft to different tissues.

While the cells described herein for graft or transplant may generally be fully differentiated, they can have limited proliferative potential, meaning that long-term survival and/or engraftment is preferred, and the treatment to knockout, or decrease the level or expression and activity of ASIC1a in the cells can promote such survival and engraftment. Cells differentiated in vitro from pluripotent stem cells to a stem or precursor cell of the mesodermal lineage upstream developmentally from a desired cell type can be treated as described herein to knockout, or decrease the level of expression and activity of ASIC1a and be administered, such that the treated cells expand in number and differentiate after administration to the subject.

The transplant compositions described herein may, in some embodiments, lack or substantially lack the agent that decreases the level of ASIC1a. That is, the cells can be treated transiently in vitro with the agent, then formulated for transplant without the agent. By "substantially lack" in this context, the transplant composition or formulation would have only that agent that remains in the cells after treatment and before or during administration. It is not necessarily required, but in some embodiments, and depending upon the nature of the agent and the delivery formulation used with it, it can be advantageous to wash out or remove the agent from adherent cells in culture prior to formulation for transplant. In other embodiments, it is contemplated that the cells can be formulated and administered in a transplant composition that includes the agent, for example in solution or suspension with the cells.

Scaffold Compositions:

In one aspect, the in vitro-differentiated cells described herein can be admixed with or grown in or on a preparation that provides a scaffold or substrate to support the cells. A scaffold is a structure comprising a biocompatible material including but not limited to a gel, sheet, matrix or lattice that can contain cells in a desired location but permit the entry or diffusion of factors in the environment necessary for survival and function. A number of biocompatible polymers suitable for a scaffold are known in the art.

Such a scaffold or substrate can provide a physical advantage in securing the cells in a given location, e.g., after implantation, as well as a biochemical advantage in providing, for example, extracellular cues for the further maturation or, e.g., maintenance of phenotype until the cells are established.

Biocompatible synthetic, natural, as well as semi-synthetic polymers can be used for synthesizing polymeric particles that can be used as a scaffold material. In general, for the practice of the methods described herein, it is preferable that a scaffold biodegrades such that the in vitro-differentiated cells can be isolated from the polymer prior to implantation or such that the scaffold degrades overtime in a subject and does not require removal. Thus, in one embodiment, the scaffold provides a temporary structure for growth and/or delivery of in vitro-differentiated cells to a subject in need thereof. In some embodiments, the scaffold permits human cells to be grown in a shape suitable for transplantation or administration into a subject in need thereof, thereby permitting removal of the scaffold prior to implantation and reducing the risk of rejection or allergic response initiated by the scaffold itself.

Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA or PLA/PGA copolymer), and other polyhydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin and silk, polysaccharides such as alginate, heparin and other naturally occurring biodegradable polymers of sugar units. Alternatively, combinations of the aforementioned polymers can be used. In one aspect, a natural polymer that is not generally found in the extracellular matrix can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature.

In some embodiments, attachment of the cells to a polymer is enhanced by coating the polymers with compounds such as basement membrane components, fibronectin, agar, agarose, gelatin, gum arabic, collagen type I, II, III, IV, and V, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments it can be desirable to add bioactive molecules/factors to the scaffold. A variety of bioactive molecules can be delivered using the matrices described herein.

In one embodiment, the bioactive factors include growth factors. Examples of growth factors include platelet derived growth factor (PDGF), transforming growth factor alpha or beta (TGFP), bone morphogenic protein 4 (BMP4), fibroblastic growth factor 7 (FGF7), fibroblast growth factor 10 (FGF10), epidermal growth factor (EGF/TGFP), vascular endothelium growth factor (VEGF), some of which are also angiogenic factors. These factors are known to those skilled in the art and are available commercially or described in the literature. Bioactive molecules can be incorporated into the matrix and released over time by diffusion and/or degradation of the matrix, or they can be suspended with the cell suspension.

Pharmaceutically Acceptable Carriers:

The in vitro-differentiated cells derived from stem cells which have been genetically modified to lack or have decreased expression and/or activity of ASIC1a, or otherwise treated with an agent that decreases the level or activity of ASIC1a, can be formulated for transplant by admixture with a pharmaceutically acceptable carrier. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as toxicity, transplant rejection, allergic reaction, and the like. A pharmaceutically acceptable carrier will not promote the raising of an immune response to an agent with which it is admixed, unless so desired.

In general, the compositions comprising in vitro-differentiated cells described herein are administered as liquid suspension formulations including the cells in combination with the pharmaceutically acceptable carrier. One of skill in the art will recognize that a pharmaceutically acceptable carrier to be used in a transplant composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the cells as described herein using routine experimentation.

Transplant compositions can optionally contain additional bioactive ingredients that further promote the survival, engraftment or function of the administered cells or, optionally, the tissue, organ or subject to which the composition is administered. Examples include, but are not limited to growth factors, nutrients, analgesics, anti-inflammatories and small molecule drugs, such as kinase activators, among others.

Physiologically tolerable carriers for the suspension of cells for a transplant composition include sterile aqueous physiological saline solutions that contain no additional materials other than the cells, or that contain a buffer such as sodium phosphate at physiological pH value, such as phosphate-buffered saline. Still further, aqueous carriers can contain more than one buffer salt, as well as salts such as sodium and potassium chlorides, dextrose, polyethylene glycol and other solutes.

Administration and Efficacy

Described herein are compositions and methods that promote the survival and/or engraftment of transplanted, in vitro-differentiated human cells, including cells of the mesodermal lineage, including, but not limited to cardiomyocytes. Transplantation of cells derived from stem cells which have been genetically modified to lack or have decreased expression and/or activity of ASIC1a, or otherwise treated with an agent that decreases the level or activity of ASIC1a, can involve the injection of a transplant composition comprising cells in a suspension, with or without a matrix or scaffold, into a desired location, e.g., a tissue in need of repair. Alternatively, transplantation can involve the surgical placement of a transplant composition comprising cells in a matrix or on a scaffold, onto or into a desired location, tissue or organ, e.g., a tissue or organ in need of repair.

The survival or engraftment of transplanted cells can be determined by any method known in the art, for example, by monitoring tissue or organ function following transplantation. Measured or measurable parameters for efficacy include clinically detectable markers of function or disease, for example, elevated or depressed levels of a clinical or biological marker, functional parameters, as well as parameters related to a clinically accepted scale of symptoms or markers for health or a disease or disorder. The survival and engraftment of the transplanted cells can be quantitatively or qualitatively determined by histological and molecular methods. In one approach, survival and engraftment can be evaluated in an appropriate animal model, e.g., a NOD scid gamma mouse model as discussed in the Examples herein. Using such a model, human cells can be injected and then evaluated for survival and engraftment by measuring human specific markers in the recipient tissue, e.g., cardiac tissue. In brief, measurement of the number of cells injected versus the number engrafted provides a measure of engraftment efficiency. Measurement of viable transplanted cells in the tissue provides a measure of survival. Viability of engrafted cells can be determined or measured by any of several methods, including, for example, histology and/or immunohistochemistry for human markers. The identification of cells as being from the transplant is based on the presence of human markers, and the morphology of the cells and/or their organization in the tissue can indicate cell viability. As but one example, Masson elastic trichrome or Movat pentachrome histological stains are particularly useful to assess interstitial fibrosis, cardiomyocyte necrosis and disarray, in addition to the presence of contraction bands in cardiac tissues. Alternatively, one can use laser capture microdissection and quantitation of human DNA sequence (e.g., human ALU repeat sequence). As yet another alternative for the evaluation of graft survival, one can quantitate human DNA sequence in homogenized tissue, e.g., heart tissue. For example, cells, e.g., cardiomyocytes prepared as described and exemplified herein can be transplanted into tissue, e.g., cardiac tissue, of a plurality of mice. At selected timepoints after transplant, tissue from individual mice can be harvested and evaluated for the presence and/or amount of human DNA as measure of the maintenance or persistence of the transplanted cells.

The term "effective amount" as used herein refers to the amount of a population of in vitro-differentiated cells treated as described herein needed to alleviate at least one or more symptoms of a disease or disorder, including but not limited to an injury, disease, or disorder. An "effective amount" relates to a sufficient amount of a composition to provide the desired effect, depending upon the cell type administered and the disease or disorder addressed, e.g., the amount necessary to treat a subject having an infarct zone following myocardial infarction, improve cardiomyocyte engraftment, prevent onset of heart failure following cardiac injury, enhance vascularization of a graft, enhance renal function, etc. The term "therapeutically effective amount" therefore refers to an amount of human in vitro-differentiated cells treated with an agent that decreases ASIC1a level or activity, or a composition including such cells that is sufficient to promote a particular effect when administered to a typical subject, such as one who has, or is at risk for, a cardiac disease, among others. An effective amount as used herein also includes an amount sufficient to prevent or delay the development of a symptom of the disease, alter the course of a disease symptom (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as being at risk of developing a disease (e.g., heart failure following myocardial injury or kidney disease) or disorder prior to administering the cells.

As noted above, for use in the various aspects described herein, an effective amount of human cardiomyocytes is at least $1 \times 10^7$, at least $2 \times 10^7$, at least $3 \times 10^7$, at least $4 \times 10^7$, at least $5 \times 10^7$, at least $6 \times 10^7$, at least $7 \times 10^7$, at least $8 \times 10^7$, at least $9 \times 10^7$, at least $1 \times 10^8$, at least $2 \times 10^8$, at least $3 \times 10^8$, at least $4 \times 10^8$, at least $5 \times 10^8$, at least $6 \times 10^8$, at least $7 \times 10^8$, at least $8 \times 10^8$, at least $9 \times 10^8$, at least $1 \times 10^9$, at least $2 \times 10^9$, at least $3 \times 10^9$, at least $4 \times 10^9$, at least $5 \times 10^9$, at least $6 \times 10^9$, at least $7 \times 10^9$, at least $8 \times 10^9$, at least $9 \times 10^9$, at least $1 \times 10^9$, at least $1 \times 10^{10}$ or more cells for transplant or graft. Similar numbers of other in vitro-differentiated mesoderm lineage cells can be used for transplant or graft to different tissues. Effective amounts of cells or a transplant composition comprising them can be initially estimated through use of an appropriate animal model. As but one example, murine, canine and porcine models of cardiac infarction are known and can be used to gauge the amounts of cells or transplant compositions comprising them effective for treatment.

In some embodiments, a composition comprising human in vitro-differentiated cells treated with an agent that decreases ASIC1a level or activity permits engraftment of the cells in the desired tissue or organ at an efficiency at least 20% greater than the engraftment when such cells are administered without such treatment; in other embodiments, such efficiency is at least 30%, at least 40%, at least 50%, at least 60%, at least 70%, at least 80%, at least 90%, at least 1-fold, at least 2-fold, at least 5-fold, at least 10-fold, at least 100-fold or more than the efficiency of engraftment when cells are administered without such treatment.

When the cells are in vitro-differentiated cardiomyocytes, an effective amount of cardiomyocytes is administered to a subject by intracardiac administration or delivery. In this context, "intracardiac" administration or delivery refers to all routes of administration whereby a population of cardiomyocytes is administered in a way that results in direct contact of these cells with the myocardium of a subject, including, but not limited to, direct cardiac injection, intramyocardial injection(s), intra infarct zone injection, ischemic- or peri-ischemic zone injection, injection into areas of wall thinning, injection into areas at risk for maladaptive cardiac remodeling, injection or implantation during surgery (e.g., cardiac bypass surgery, during implantation of a cardiac mini-pump or a pacemaker, etc.). In some such embodiments, the cells are injected into the myocardium (e.g., cardiomyocytes), or into the cavity of the atria and/or ventricles. In some embodiments, intracardiac delivery of cells includes administration methods whereby cells are administered, for example as a cell suspension, to a subject undergoing surgery via a single injection or multiple "mini" injections into the desired region of the heart.

The choice of formulation will depend upon the specific composition used and the number of treated cells to be administered; such formulations can be adjusted by the skilled practitioner. However, as an example, where the composition includes cardiomyocytes in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells. Alternatively, as noted herein above, the formulation can comprise a scaffold, such as a biodegradable scaffold as described herein or as known in the art.

In some embodiments, additional agents to aid in treatment of the subject can be administered before or following treatment with the cells as described. Such additional agents can be used, for example, to prepare the target tissue for administration of the cells. Alternatively, the additional agents can be administered after the cells to support the engraftment and growth or integration of the administered cells into the tissue or organ. In some embodiments, the additional agent comprises growth factors, such as VEGF, PDGF, FGF, aFGF, bFGF, IGF or Notch signaling compounds. Other exemplary agents can be used, for example, to reduce the load on the heart while cardiomyocytes are engrafting (e.g., beta blockers, medications to lower blood pressure, etc.).

In some embodiments of any of the aspects, the additional agent is administered beginning at least 1 hour, at least 5 hours, at least 10 hours, at least 15 hours, at least 20 hours, at least 1 day, at least 2 days, at least 3 days, at least 4 days, at least 5 days, at least 6 days, at least 7 days at least 8 days, at least 9 days, at least 10 days, prior to administration of the treated cells. In some embodiments of any of the aspects, the additional agent is administered concurrently with or following administration of the treated cells.

The efficacy of treatment can be determined by the skilled clinician. However, a treatment is considered "effective treatment," as the term is used herein, if any one or all of the symptoms, or other clinically accepted symptoms or markers of disease, e.g., cardiac disease, heart failure, cardiac injury or a cardiac disorder, renal disease or disorder, etc. are reduced, e.g., by at least 10% and including, for example, at least 20%, at least 30%, at least 40%, at least 50%, at least 60%, at least 70%, at least 80%, at least 90% or more following administration of a transplant composition comprising treated cells as described herein. Methods of measuring these indicators are known to those of skill in the art and/or described herein.

Where the transplanted cells are cardiomyocytes, indicators of a cardiac disease or cardiac disorder, or cardiac injury include functional indicators or parameters, e.g., stroke volume, heart rate, left ventricular ejection fraction, heart rhythm, blood pressure, heart volume, regurgitation, etc. as well as biochemical indicators, such as a decrease in markers of cardiac injury, such as serum lactate dehydrogenase, or serum troponin, among others. As one example, myocardial ischemia and reperfusion are associated with reduced cardiac function. Subjects that have suffered an ischemic cardiac event and/or that have received reperfusion therapy have reduced cardiac function when compared to that before ischemia and/or reperfusion. Measures of cardiac function include, for example, ejection fraction and fractional shortening. Ejection fraction is the fraction of blood pumped out of a ventricle with each heartbeat. The term ejection fraction applies to both the right and left ventricles. LVEF refers to the left ventricular ejection fraction (LVEF). Fractional shortening refers to the difference between end-diastolic and end-systolic dimensions divided by end-diastolic dimension.

Non-limiting examples of clinical tests that can be used to assess cardiac functional parameters include echocardiography (with or without Doppler flow imaging), electrocardiogram (EKG), exercise stress test, Holter monitoring, or measurement of natriuretic peptide (e.g., atrial natriutetic peptide).

Where necessary or desired, animal models of injury or disease can be used to gauge the effectiveness of a particular composition as described herein. For example, an isolated working rabbit or rat heart model, or a coronary ligation model in either canines or porcines can be used. Animal models of cardiac function are useful for monitoring infarct zones, coronary perfusion, electrical conduction, left ventricular end diastolic pressure, left ventricular ejection fraction, heart rate, blood pressure, degree of hypertrophy, diastolic relaxation function, cardiac output, heart rate variability, and ventricular wall thickness, etc.

For the monitoring of engraftment or survival of transplanted cells, the cells can be marked or tagged, for example, by introduction of a construct that directs the expression of a marker, such as, but not limited to GFP or other fluorescent protein, or an epitope tag or a genetic barcode. When cells expressing such a marker are administered to an animal model, functional parameters can be gauged as for any cell, but tissue can also be removed after cell administration and tested or assayed, e.g., via fluorescence microscopy or immunohistochemistry, for the expression of the marker. Persistence or level of marker expression can thus be used to gauge the efficacy of the cell treatment described herein in enhancing or promoting cell survival and/or engraftment using such an animal model.

In addition to treatment of cells with an agent that decreases the level or activity of ASIC1a, when the cells are cardiomyocytes, other approaches or treatments known in the art to promote or enhance the survival, engraftment, maturity and/or function of transplanted cardiomyocytes can be performed before, concurrently or in parallel with, or after administration of the treated cells. See, for example, WO2018/170280, which describes, among other things, the in vitro differentiation and co-transplantation of epicardial cells with in vitro-differentiated cardiomyocytes. Such treatment was also found to promote cardiomyocyte engraftment and to enhance cardiac function upon transplant. WO2018/170280 is incorporated herein by reference in its entirety, but with particular note of methods described therein for transplant of cardiomyocytes, markers and measurement of cardiomyocyte maturity, co-transplant with epicardial cells, measurement of transplant engraftment, survival and/or function, and the measurement of efficacy of such transplants.

In other embodiments, the transplant compositions described herein may be used to treat a disease or improve survival, e.g., to reduce the onset, incidence of severity of a cardiovascular disease. The efficacy of a therapeutic treatment can be assessed by the presence or absence of a symptom of a disease by functional output (e.g., measuring cardiac output or renal function), markers, levels or expression (e.g., serum levels of cardiac enzymes, markers of ischemia, renal function or insufficiency), and/or electrographic means (e.g., an electrocardiogram). Further, as will be appreciated by a skilled physician, the ability to modify the transplant compositions described herein can permit them to customize a treatment based on a subject's particular set of symptoms and/or severity of disease and further to minimize side effects or toxicity.

These and other aspects of the invention are illustrated by the following non-limiting examples. It should be appreciated that in some aspects one or more embodiments described in the examples may be generally applicable in combination with one or more embodiments described above.

EXAMPLES

Materials and Methods

Materials and methods utilized for the Examples described below are as follows:

Study Design. All animal experiments were performed in accordance with protocols approved by the Animal Ethics Committee of The University of Queensland (UQ) (IMB/171/18) and Garvan Institute of Medical Research (16/38). All hiPSC studies were performed with consent from the UQ Institutional Human Research Ethics approval (HREC #2015001434). Additional information for each set of experiments, such as statistical analyses, exclusion criteria, and sample size, are detailed in the relevant methods section or figure legend. All data and materials associated with this study can be provided upon request.

Animals. All animals used in this study received humane care in compliance with Australian National Health and Medical Research Council guidelines and the *Guide for the Care and Use of Laboratory Animals* (U.S. National Institutes of Health). To test the therapeutic efficacy of ASIC1a inhibitors, male C57BL/6 mice (Langendorff IRI experiments) or male Wistar rats (donor organ preservation experiments) were purchased from the Animal Resource Centre (Canning Vale, Western Australia).

For genetic ablation studies, ASIC1a−/− mice were generated at the Australian Phenomics Facility. CRISPR/Cas9 technology was used to specifically target the mouse ASIC1a sequence. Use of guide RNAs (gRNA) with sequences CCGAGGAGGAGGAGGTGGGTGGT (SEQ ID No. 20) and GTACCATGCTGGGGAACTGCTGG (SEQ ID No. 21) resulted in single nucleotide deletions within both targeted regions, at positions 22 and 341 (NM_009597.2(ASIC1_v001):c.22del and NM_009597.2(ASIC1_v001):c.341del). These deletions predicted a disrupted ASIC1a protein sequence (p.Glu8Argfs*9 and p.Leu114Argfs*94, respectively). The founder mouse was backcrossed to C57BL/6 background. Both hetero- and homozygous mice were viable and showed no obvious phenotype. Total RNA was isolated from brain tissue using Trizol Reagent (ThermoFisher Scientific, Massachusetts, USA), and contaminant genomic DNA was removed with DNA-free reagents (Ambion/Life Technologies, Austin, USA). Primer sequences designed to distinguish between ASIC1a and ASIC1b transcripts were used to determine gene expression levels in ASIC1a KO and WT animals(73). Primer sequences used in this study were ASIC1a forward 5'-CTGTACCATGCTGGGGAACT-3' (SEQ ID No. 2) and reverse 5'-GCTGCTTTTCATCAGCCATC-3' (SEQ ID No. 3); ASIC1b forward 5'-TGCCAGCCATGTCTTTGTG-3' (SEQ ID No. 4) and reverse 5'-CACAG-GAAGGCACCCAGT-3' (SEQ ID No. 5) and RPL32 (for sample normalization) forward 5'-GAGGTGCTGCT-GATGTGC-3' (SEQ ID No. 6) and reverse 5'-GGCGTTGG-GATTGGTGACT-3'(SEQ ID No. 7). For quantitative real-time (qRT)-PCR, oligo-dT primed cDNA was synthesized from 500 ng of total RNA using Murine Moloney Leukaemia Virus reverse transcriptase (Promega, USA). qRT-PCR was performed using a ViiA Real-Time PCR System (Applied Biosystems, CA, USA) using SYBR® green master mix (Promega, USA) according to manufacturer protocols. Relative ASIC1a and ASIC1b gene expression values were obtained from ASIC1a−/− mice and WT (ASIC1a+/+) mice (calibrator) by normalization to the reference gene RPL32 using the 2-ΔΔCt method, where 2-ΔΔCt=ΔCt sample−ΔCt calibrator.

IRI in Langendorff-perfused mouse hearts. Isolated hearts were assessed for tolerance to IRI as previously described (L. E. See Hoe et al., *J Pharmacol Exp Ther* 369, 37-46 (2019); M. E. Reichelt, et al. *Exp Physiol* 94, 54-70 (2009)). Mice (12-14 weeks) were anesthetized via an intraperitoneal injection of 10 mg/mL ketamine and 1.6 mg/mL xylazil. The heart was excised via thoracotomy and the aorta cannulated. The hearts were retrogradely perfused under constant hydrostatic pressure (80 mmHg) with oxygenated (95% O2; 5% CO2) modified Krebs-Henseleit buffer (composition in mM: 119 NaCl, 22 NaHCO3, 4.7 KCl, 1.2 MgCl2, 1.2 KH2PO4, 0.5 EDTA, 1.85 CaCl2), 11 D-(+)-glucose, 2 Na+ pyruvate, all from Sigma-Aldrich). Temperature was continuously measured with thermocouple needle microprobes (SDR Scientific) and maintained at 37° C. with circulating water baths. Contractile function was measured via a fluid-filled balloon inserted in the left ventricle and connected to a pressure transducer (ADInstruments Pty Ltd.). Coronary flow was measured with an in-line Doppler flow probe positioned above the aortic cannulae (Transonic Systems Inc.). All functional data were recorded on a four-channel MacLab system (ADInstruments Pty Ltd.). Following 15-30 min of equilibration, hearts were switched to ventricular pacing at 420 beats/min (BPM) using a SD9 stimulator (Grass Instruments, Inc.). Baseline measurements were made for 10-20 min followed by 25 min of global normothermic ischemia and 45 min of reperfusion. Pacing was stopped during ischemia and resumed after 15 min of reperfusion. For peptide-treated experimental groups, 1 μM peptide solution was infused with a syringe pump (World Precision Instruments, LLC.) into the buffer, directly upstream of the cannula, at a rate of 1% of CF, for a final working concentration of 10 nM. Peptide was infused for 10 min prior to the onset of ischemia and during the first 15 min of reperfusion. To assess cell death, effluent was collected at 2 and 45 min after the start of reperfusion. Effluent levels of LDH were measured using a cytotoxicity detection kit (Roche). Normalized absorbance values (absorbance at 492 nm minus absorbance at 690 nm) were measured using a PHERAStar FS microplate reader (BMG Labtech). Standard curves were generated with bovine LDH (Sigma-Aldrich) and used to convert sample absorbance values to units of LDH. Data were normalized to CF and heart weight and then expressed as U/min/g. For all analyses, hearts were excluded if they met the following criteria: abnormally high coronary flow (>8 mL/min), delayed onset of ischemic contracture (time to onset of ischemic contracture (TOIC) >20 min), poor contractile function after equilibration (significant arrhythmias and/or left ventricular systolic pressure <80 mmHg), or technical issues with the perfusion rig.

In vivo myocardial IRI surgery. Surgeries were performed on 10-week-old male mice (C57BL/6). The surgeon was blinded to the treatments in all surgery. Prior to anaesthesia, mice were injected with 1 mg/kg Hi1a or vehicle control (0.1% BSA in saline) via tail vein injection. Mice were anesthetized by 4% isoflurane followed by endotracheal intubation and mechanical ventilation. Analgesia was provided by subcutaneous injection of buprenorphine (0.05 mg/kg). Isoflurane was reduced to 2-2.5% to maintain anaesthetic plane for the remainder of the procedure. A lateral thoracotomy was performed, the left anterior descending artery (LAD) identified and temporarily occluded (40 minutes of ischemia) 2 mm below the left atrial appendage with 7-0 prolene suture (Ethicon, Somerville, NJ, USA) tied around a piece of PE10 tubing placed on the LAD. Successful ligation was confirmed by significant blanching of the myocardium below the point of ligation. At the end of the ischemic period, the suture and tubing were removed and reperfusion was confirmed with returned pallor of the myocardium. After surgery, the chest and skin were closed with 5-0 prolene suture (Ethicon, Somerville, NJ, USA) and the mice allowed to recover. Sham operated mice underwent the same procedure without LAD ligation. Body temperature was controlled and monitored via a rectal probe for the duration of the surgery to maintain 37.0±0.5° C. Buprenorphine (0.05 mg/kg) was administered every 12 hours for three additional days and the overall post-operative health of the animals were closely monitored every day.

Echocardiography

Echocardiography was performed prior to surgery (baseline), and at 1- and 4-weeks post-surgery using a Vevo3100 ultrasound system (VisualSonics, Toronto, Canada) with a 25-55 MHz transducer (MX550D). All echocardiographic measurement and analysis were conducted in a blinded manner. Mice were anesthetized with 2.5% isoflurane and general anaesthesia was maintained with 1% isoflurane during echocardiography. Mice in supine position were placed on a heating pad and heart rate (HR) and electrocardiography were recorded. Body temperature was controlled and monitored for the duration of the echocardiography to maintain 37.0±0.5° C. Two-dimensional B-mode images were recorded in the parasternal long axis view and used to determine left ventricle end-diastolic volume (LVEDV), left ventricle end-systolic volume (LVESV), ejection fraction (EF), and cardiac output (CO). LVEDV, LVESV, and CO were normalized to body weight [left ventricle end-diastolic volume index (LVEDVI), left ventricle end-systolic index (LVESVI), and cardiac index (CI), respectively]. The recorded images were analysed using Vevo LAB 3.1.1 software (VisualSonics, Toronto, Canada). All parameters were measured at least three times and the averages are presented.

Histology.

At the experimental endpoint (4 weeks), the mice were euthanized with an overdose of ketamine (10 mg/mL ketamine) and xylazil (1.6 mg/mL). The hearts were perfused with 3-4 mL PBS via intracardiac injection followed by excision of the heart. The hearts were briefly submerged in supersaturated KCl (>5M) to arrest the heart in diastole followed by overnight fixation in 4% paraformaldehyde at 4° C. Samples were transferred to 70% EtOH and paraffin processed and embedded. 4 μm sections were cut and stained for Masson's trichrome blue. Stained sections were imaged at 10× resolution with a slide scanner (Zeiss Axioscan), and analysed with ZEN Lite 3.1. For each heart, the area of fibrosis was measured in 4 separate sections (2 mm tiles from apex to base) with ImageJ software. Values are presented as a summation of fibrosis area in all 4 sections divided by total LV area.

Peptide production. Recombinant Hi1a was produced by expression as a His6-maltose-binding protein (MBP) fusion protein in the periplasm of *Escherichia coli* as previously described (I. R. Chassagnon et al., Proc. Natl. Acad. Sci. U.S.A. 114, 3750-3755 (2017)), but with optimisation of the expression and purification conditions to improve the yield. Briefly, *E. coli* BL21(DE3) cells were grown at 30° C. in Terrific Broth until the optical density at 600 nm reached 2.0-2.5, at which point the temperature was reduced to 17° C. and expression of the Hi1a fusion protein was induced with 1 mM IPTG. Cells were harvested after a further 21 h growth. PcTx1 and the PcTx1-R27A/V32A analogue were produced in the same manner with minor modifications to the expression protocol. *E. coli* were grown at 37° C. for the entire expression period and harvested approximately 4-5 h after induction. Cell pellets were resuspended in 50 mM Tris, 300 mM NaCl, 5% glycerol, 15 mM imidazole (pH 8.3 for Hi1a or pH 8.0 for PcTx1), and the cells were lysed by high-pressure cell disruption (Constant Systems Limited, UK). The His6-MBP-peptide fusion proteins were purified from the clarified soluble lysate over a nickel affinity resin. The resin was washed with the same buffer to elute weakly bound proteins before eluting the Hi1a fusion protein with the same buffer containing 300 mM imidazole. Fusion proteins were exchanged into low (<30 mM) imidazole buffer using an Amicon Ultra-15 centrifugal concentrators (Merck Millipore, Germany) with a 30 kDa molecular weight cut-off in preparation for liberation of Hi1a from the fusion tag using tobacco etch virus (TEV) protease. The fusion proteins were cleaved in redox buffer containing 3 mM reduced glutathione and 0.3 mM oxidised glutathione at pH 8.3 for Hi1a or pH 8.0 for PcTx1, using ~1 mg of TEV protease per 50 mg of fusion protein. For Hi1a the cleavage reaction was allowed to proceed at 4° C. over 3-6 days. For the PcTx1 peptides, cleavage was performed at room temperature for a minimum of 16 h. The recombinant peptides each contain a non-native N-terminal serine residue, which is a vestige of the TEV protease recognition site. The released peptides were purified from the cleavage reaction solutions using reverse phase high-performance liquid chromatography. The mass of the purified peptides were confirmed by electrospray-ionisation mass spectrometry and pure peptides were lyophilised prior to confirmation of ASIC1a inhibitory activity using two-electrode voltage-clamp electrophysiology, as described previously for Hi1a (I. R. Chassagnon et al.) and PcTx1 (N. J. Saez et al. Mol Pharmacol 80, 796-808 (2011), C. A. McCarthy, et al Neuropharmacology 99, 650-657 (2015), N. J. Saez et al., Br J Pharmacol 172, 4985-4995 (2015)). Unless otherwise noted, lyophilized stocks of peptide were reconstituted in sterile deionised water prior to use.

Generation of cardiomyocytes from hiPSCs. Cardiomyocytes generated in this study were derived from the WTC-11 hiPSC line (Gladstone Institute of Cardiovascular Disease, UCSF) (Y. Miyaoka et al., Nat Methods 11, 291-293 (2014), F. R. Kreitzer et al. Am J Stem Cells 2, 119-131 (2013)). Undifferentiated hiPSCs were maintained on Vitronectin XF (5 µg/mL, Stem Cell Technologies) coated tissue culture dishes as per manufacturer recommendation with either mTeSR™ or mTeSR™ PLUS medium with supplementation (Stem Cell Technologies). Contractile cardiomyocytes were differentiated using a high-density monolayer format as described (C. E. Friedman et al., Cell Stem Cell 23, 586-598.e588 (2018)). hiPSCs were dissociated with 0.5 mM EDTA solution supplemented with 1.1 mM D-glucose. Single-cell suspensions were plated at a density of 1.2×105 cells/cm2 and cultured overnight in mTeSR™ medium supplemented with 10 µM Y-27632 dihydrochloride (Stem Cell Technologies). Once the monolayer reached approximately 80% confluence (usually the following day), differentiation was induced (day 0). The cells were quickly washed with PBS followed by a change in medium to RPMI (ThermoFisher) containing 3 µM CHIR99021 (Stem Cell Technologies), 500 µg/mL BSA (Sigma Aldrich), and 213 µg/mL ascorbic acid (Sigma Aldrich). After 3 days of culture, the medium was exchanged to RPMI containing 500 µg/mL BSA, 213 µg/mL ascorbic acid, and 5 µM Xav-939 (Stem Cell Technologies). On day 5, the medium was replaced with RPMI containing BSA and ascorbic acid as on day 3. Starting on day 7, the cells were fed every other day with RPMI containing 1×B27™ supplement with insulin (Life Technologies). Spontaneous beating was typically observed between days 9 and 11 of differentiation.

In vitro ischemia-acidosis injury model with hiPSC-CMs. Differentiated cardiomyocytes were replated on either day 15 or day 17 of differentiation for in vitro ischemia/acidosis assays. At the time of replating, a subset of cells (~500,000) was set aside for flow cytometry analysis of cardiomyocyte purity (see supplemental methods). For all experiments, only cell preparations with >80% sarcomeric α-actinin-positive cardiomyocytes were used. After re-plating, the cells were maintained for an additional 7 days in RPMI+B27™. To prepare media for ischemia/acidosis injury, 10×HBSS without sodium bicarbonate (Sigma) was diluted to 1× concentration in sterile tissue culture-grade water. Solutions were buffered with either 12 mM HEPES (for pH 7.4 media, Sigma Aldrich) or 12 mM MES (for pH <6.5, Sigma Aldrich) and the pH adjusted accordingly with 1 M NaOH. The medium was sterile filtered with 0.22 µm syringe filters (Millipore). Unless otherwise noted, the replated cells were treated overnight (18 h) in HBSS with or without peptide under either normoxic (~18.5% O2; 5% CO2) or hypoxic (0.5% O2; 5% CO2) culture conditions. For reperfusion experiments, the medium was replaced with HBSS pH 7.4 (with or without peptide) after overnight incubation and cultured for 1 h under normoxic conditions. To assess cell death, supernatant was collected and LDH levels were measured using a cytotoxicity detection kit (Roche). For all cell culture experiments, percent cell death was calculated using low and high controls. For low control (LC), cardiomyocytes were cultured overnight in standard culture media (RPMI+B27™). For high control (HC), cells were cultured in RPMI+B27™ containing 1% Triton™ X-100 (Sigma-Aldrich).

hiPSC-CM calcium analysis. Cardiomyocytes were replated (2×104 per well) in 384-well plates (CellBIND black with clear bottom, Corning) and cultured for 7 days in RPMI+B27™. On the day of the experiment, the cells were loaded for 1.5 h at 37° C. with FLIPR calcium 4 dye (Molecular Devices) diluted in HBSS pH 7.4. After loading, the plate was transferred to a FLIPR Tetra fluorescent plate reader (Molecular Devices). Calcium transients were measured with excitation wavelengths at 470-495 nm and emission at 515-575 nm. For each plate, the camera gain and intensity were adjusted to optimize signal intensity. Data for each well were expressed as normalized arbitrary fluorescence units. All data were acquired at 0.5 s per read, with baseline measurements for 45 s followed by at least 100 s of data collection after each peptide addition. Peptide solutions (in HBSS pH 7.4) were added to each well to give a final concentration of 1 nM, 10 nM, 100 nM, or 1 µM. Calcium amplitude, maximum calcium, minimum calcium, and spontaneous beating rate were analysed using ScreenWorks software (Molecular Devices) and normalized to baseline measurements.

Analysis of GWAS studies. To assess whether genetic variation of ASIC1 associates with cardiovascular disease and stroke, inventors performed a gene-based level test on GWAS summary data using fastBAT (A. Bakshi et al., Sci Rep 6, 32894 (2016)) implemented in the Complex-Traits Genetics Virtual Lab (CTG-VL) (G. Cuellar-Partida et al., BioRxiv, 518027 (2019)). GWAS summary data contains the statistical information of the association of all the genetic variants included in a GWAS against a particular trait. fastBAT tests the aggregated effects of a set of genetic variants within or close to (±50 kb) each tested gene (ACCN1 in this case) using a set-based association approach which accounts for the correlation between genetic variants (i.e. linkage disequilibrium). This provides a more powerful approach over single-variant tests. Specifically, the inventors performed analyses using GWAS summary data for acute MI (Ncases=5,948, Ncontrols=354,176), major coronary heart disease (Ncases=10,157, Ncontrols=351,037) and MI (Ncases=7,018, Ncontrols=354,176) from Neale's UK Biobank GWAS database (The UK Biobank, nealelab.is/uk-biobank, 2018) and stroke (including any type of stroke, ischemic stroke, large artery stroke, cardioembolic stroke and small vessel stroke (R. Malik et al., Nat Genet 50, 524-537 (2018)) (Ncases=40,585, Ncontrols=406,111).

Statistical Analysis. All data are presented as mean±SEM. Statistical analyses were performed with GraphPad Prism and comparisons were made using Student's t-test, one-way analysis of variance (ANOVA), or two-way ANOVA. All data were derived from a minimum of three independent experiments with specific information for each experiment detailed in the relevant figure legend. Differences were considered significant with p<0.05.

Figure 1:
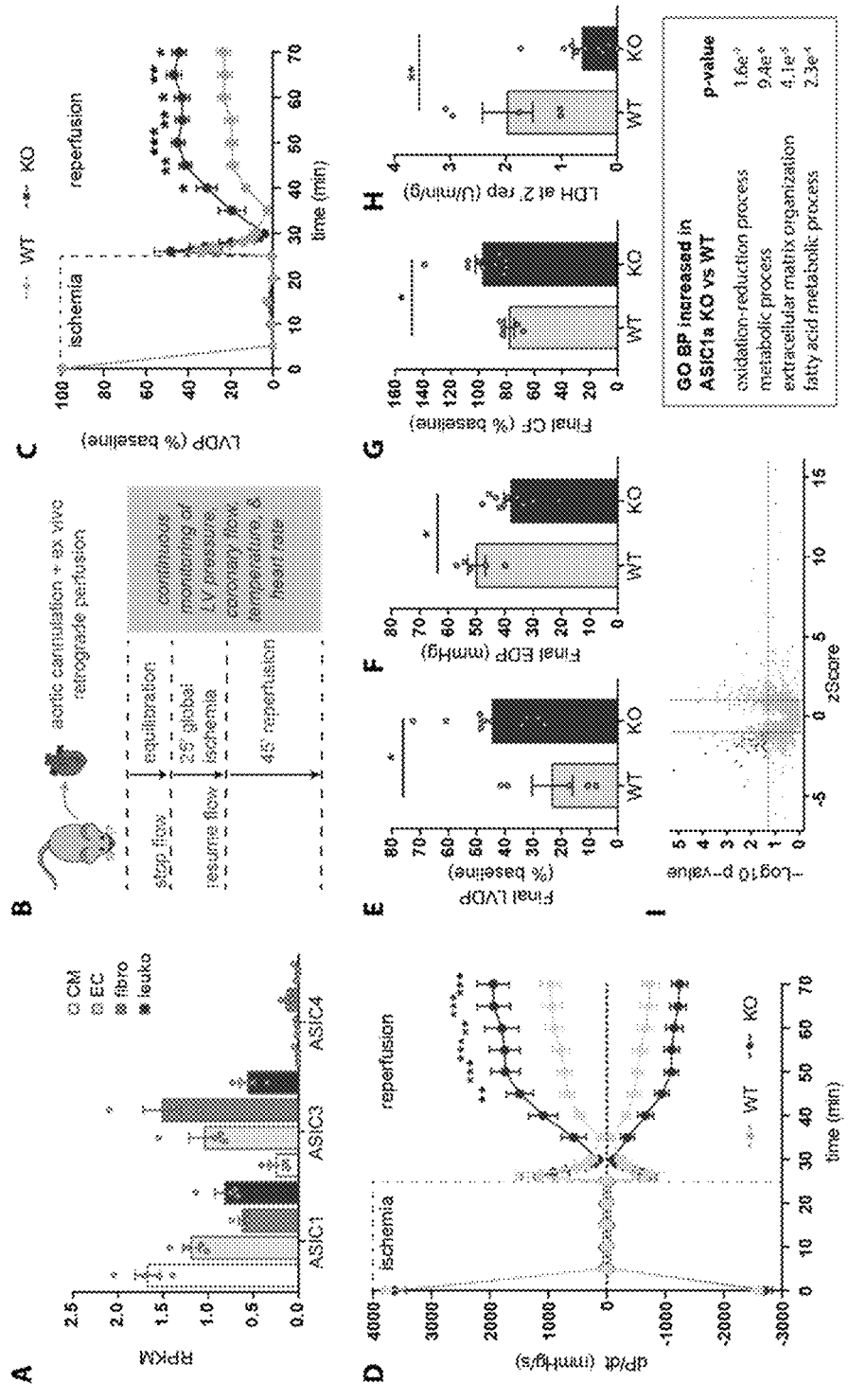
FIG. 1. Genetic knockout of ASIC1a protects mouse hearts from ex vivo IRI. (A) mRNA expression (reads per kilobase million, RPKM) analysis of sorted cardiac cell populations from P56 adult mouse hearts (data extracted from Ref. (6)). ASIC2 was not detected. (B-F) Langendorff-perfused hearts from ASIC1a KO (ASIC1a−/−, n=10) and WT (ASIC1a+/+, n=5) mice were subjected to 25 min of global ischemia followed by 45 min of reperfusion. (C) LVDP, expressed as % of pre-ischemia baseline, over time. (D) Positive and negative rate of change in pressure over time in ASIC1a KO vs WT hearts. (E-F) Functional parameters after 45 min of reperfusion including (E) LVDP, percent baseline (p=0.025) and (F) EDP, p=0.013. (G) CF, percent baseline (p=0.049). (H) Cell death after 2 min of reperfusion (units/mL of LDH normalized to reperfusion flow rate and heart weight, U/min/g, p=0.006). For LVDP and CF, baseline values were obtained immediately prior to ischemia. (I) Quantitative proteomic analysis showing volcano plot and all biological processes significantly increased in ASIC1a KO hearts compared to WT. All data are expressed as mean±SEM. Statistical significance was determined using two-way ANOVA (panels c and d) or two-tailed unpaired Student's t-test (panels e-h) (*p<0.05; p<0.01; *p<0.001).

Example 1. Genetic Ablation of ASIC1a Improves Functional Recovery Following Cardiac IRI The inventors assessed ASIC isoform expression in the adult mouse heart using transcriptomic data of sorted cardiac cell populations (G. A. Quaife-Ryan et al., Circulation 136, 1123-1139 (2017)). ASIC1 expression was highest in cardiomyocytes, while endothelial cells and fibroblasts expressed both ASIC1 and ASIC3. In all three cell types, ASIC4 and ASIC2 had low and undetectable expression, respectively (FIG. 1A).

ASIC1 encodes two isoforms from the same genetic locus, ASIC1a and ASIC1b, that are genetically conserved in bilaterians. As opposed to ASIC1b, which is primarily involved in nociception, the inventors focused on ASIC1a due to its known role in mediating ischemic injuries of the brain.

To determine whether ASIC1a plays a functional role during cardiac ischemia, the inventors assessed IRI tolerance of Langendorff-perfused isolated hearts from ASIC1a-specific knockout (KO) mice. To generate the ASIC1a KO mouse strain, the inventors used CRISPR editing to target the ACCN1 locus. Specificity of the knockout was confirmed using qRT-PCR, which showed that only ASIC1a, but not ASIC1b mRNA was reduced in brain tissue from KO mice (FIG. 5A-B). Baseline function and heart rate in ASIC1a KO (ASIC1a−/−) isolated hearts were comparable to those measured in wild-type (WT) control hearts (ASIC1a+/+) (Table 1).

TABLE 1

Baseline functional parameters of isolated hearts from wild-type and ASIC1a KO mice

| Genotype | Heart Rate (bpm) | LVDP (mmHg) | EDP (mmHg) | +dP/dt (mmHg/s) | −dP/dt (mmHg/s) | CF (mL/min/g) |
|---|---|---|---|---|---|---|
| Wildtype (ASIC1a$^{+/+}$) | 353 ± 23 | 105 ± 4 | 6.8 ± 0.7 | 3777 ± 139 | −2592 ± 144 | 35 ± 5 |
| KO (ASIC1a$^{-/-}$) | 339 ± 17 | 101 ± 4 | 5.1 ± 0.7 | 3647 ± 236 | −2702 ± 148 | 26 ± 3 |
| p-value | 0.67 | 0.54 | 0.13 | 0.66 | 0.64 | 0.25 |

All pre-ischemia functional parameters were measured in Langendorff perfused hearts after more than 30 min of stabilization, except for heart rate, which was measured after 15 min of stabilization, prior to ventricular pacing. All values are expressed as mean ± SEM.

To assess tolerance to IRI, hearts were subjected to 25 min of global normothermic zero-flow ischemia, followed by 45 min of aerobic reperfusion (FIG. 1B). WT and ASIC1a KO hearts showed similar initial responses to ischemia with comparable levels of ventricular contracture (FIG. 5C). During reperfusion, both groups demonstrated gradual recovery of contractile function over time, with markedly improved contractile recovery in ASIC1a KO hearts as measured by LVDP and dP/dt (FIG. 1C-D). By the end of the reperfusion period, ASIC1a KO hearts had significantly higher left ventricular developed pressure (LVDP) (44±5% of baseline) and lower end diastolic pressure (EDP) (38±3 mmHg) compared to WT hearts (LVDP: 23±7% of baseline; EDP: 50±3 mmHg); FIG. 1E-F). ASIC1a KO hearts also had improved recovery of coronary flow (CF) by the end of reperfusion (KO: 97±6%; WT: 78±3%, percent baseline) (FIG. 1G and FIG. 5D-E). To assess cell death, lactate dehydrogenase (LDH) efflux was measured in perfusate samples collected during reperfusion. LDH efflux from ASIC1a KO hearts was significantly lower compared to WT hearts after 2 min of reperfusion (FIG. 1H), with a similar trend at the end of reperfusion (FIG. 5F). Our data indicate that ASIC1a does not play a role in maintaining functional homeostasis, but it is a critical mediator of the organ response to myocardial IRI.

Among proteins with significantly different abundance, gene ontology analysis revealed no significant differences in down-regulated biological processes in ASIC1a KO vs WT hearts. However, ASIC1a KO hearts showed significant increases in proteins related to oxidation-reduction, fatty acid metabolism, and extracellular matrix organization (FIG. 1I and Supplemental FIG. 5G-H). These data suggest that improved survival and functional performance of ASIC1a hearts is at least in part mediated through increased abundance of molecules maintaining metabolic and structural homeostasis under conditions of severe acute myocardial ischemia.

Example 2. ASIC1a Inhibitors Protect Mouse Hearts Against IRI

Despite significant investment and preclinical testing, drug development pipelines have failed to identify effective small molecule inhibitors of ASIC1a with therapeutically useful specificity, potency, and functional efficacy. The inventors also sought to determine whether pharmacological inhibition of ASIC1a is cardioprotective during an acute cardiac ischemic insult. The inventors therefore took advantage of two venom-derived peptides that are both potent and selective inhibitors of ASIC1a, with no activity on other ASIC isoforms. Hi1a is a 76-residue double-knot peptide isolated from the venom of an Australian funnel-web spider (FIG. 2A); it is the most potent and selective inhibitor of ASIC1a identified to date, with an IC50 on rat and human ASIC1a of ~500 pM. PcTx1, a single-knot peptide from the venom of a tarantula, is also a potent and selective inhibitor of ASIC1a (IC50 ~1 nM). Although the two peptides are closely related (Hi1a is comprised of two PcTx1-like domains joined by a short linker; FIG. 2B-C), they have distinct inhibitory modes of action. Hi1a inhibits ASIC1a activation whereas PcTx1 promotes and stabilizes a desensitized state of the channel. The inventors also utilized an analogue of PcTx1 that contains mutations of two pharmacophore residues (R27A/V32A), which dramatically reduces its inhibitory effect on ASIC1a.

To examine if these ASIC1a inhibitors are cardioprotective, the inventors assessed tolerance to IRI in Langendorff-perfused isolated mouse hearts with and without peptide treatment. Consistent with genetic ablation of ASIC1a, Hi1a, PcTx1, and PcTx1-R27A/V32A had no effect on baseline contractile function during the first 10 min of peptide infusion prior to ischemia (FIG. 2D). Contractile recovery after IRI measured by LVDP and dP/dt was greater in hearts exposed to Hi1a or PcTx1 (10 nM) compared to control hearts (FIG. 2E-F). At the end of reperfusion, Hi1a- and PcTx1-treated hearts, but not hearts treated with the PcTx1-R27A/V32A analogue, had markedly improved recovery of LVDP (Hi1a: 60±4%, PcTx1: 49±12%, PcTx1-R27A/V32A: 36±6%) compared to vehicle controls (20±4%) (FIG. 2G). Similarly, treatment with Hi1a and PcTx1, but not PcTx1-R27A/V32A, led to reduced EDP after 45 min reperfusion (Hi1a: 35±4 mmHg; PcTx1: 33±8 mmHg; PcTx1-R27A/V32A: 48±3 mmHg) compared to vehicle controls (57±2 mmHg) (FIG. 2H). No differences in final CF were observed between groups (FIG. 2I), although hearts treated with PcTx1, but not Hi1a, displayed significant reactive hyperaemia during early reperfusion, as evidenced by increased CF during the first 5 min of reperfusion (FIG. 6A,B). To demonstrate specificity of Hi1a, the inventors also show that exposure of hearts to Hi1a in an ASIC1a KO background shows no additive effect in functional recovery after global IRI (FIG. 6C-F). Taken together, these data show that ASIC1a inhibitors protect the heart from myocardial IRI and recapitulate the functional benefits of genetic ablation of the channel.

Example 3. ASIC1a Blockade Prevents Adverse Chamber Remodelling and Improves Cardiac Function Post IRI In Vivo The inventors next evaluated whether Hi1a treatment improves recovery of function in vivo in a murine model of myocardial IRI (FIG. 5). The inventors carried out a preconditioning model in which Hi1a was delivered by bolus intravenous injection (1 mg/kg) in mice just prior to anaesthesia (FIG. 5A). Mice were anaesthetised and intubated followed by surgical thoracotomy to enable ligation of the proximal left anterior descending (LAD) coronary artery. Cardiac ischemia was induced for 40 min followed by reperfusion. Mice were evaluated by serial echocardiography over 4 weeks to assess functional recovery, and terminal histological analysis of hearts was performed to examine fibrosis. At four weeks, analysis of fibrosis measured by Mason's trichrome as a percent of the left ventricle showed significant reduction in collagen deposition in Hi1a-treated hearts compared to vehicle-treated animals (FIG. 5B-C). Histological data were supported by assessment of functional performance. As expected, vehicle treated animals showed significant dilation of ventricular volumes at end systole and diastole with a concomitant decrease in ejection fraction compared to sham animals (FIG. 5D-G). In contrast, ejection fraction was improved at one week in Hi1a-treated animals compared to vehicle controls, demonstrating a therapeutic functional benefit during the early remodelling phase that remained improved, albeit not significant, at 4 weeks (p=0.08) (FIG. 5D). Hi1a-treated hearts also showed no significant difference in ventricular volumes compared to sham at four weeks post-IRI, demonstrating that ASIC1a blockade prevents adverse myocardial remodelling post MI (FIG. 5F-G). This preconditioning in vivo model provides evidence of efficacy by pharmacological blockade of ASIC1a, resulting in significantly improved cardiac geometry and function post IRI.

Example 4. ASIC1 is Expressed in the Human Heart and Polymorphisms in its Genetic Locus are Associated with Ischemic Disease To assess conservation of ASIC1a biology in humans, the inventors analysed ASIC expression patterns from mRNA-seq and ribo-seq data collected from human left ventricular cardiac tissue, which revealed highest expression of ASIC1 and ASIC3 in the human left ventricle and similar levels of ASIC1 expression in samples from HF and non-HF patients (FIG. 7A,B). The inventors next assessed whether natural variation in the genetic locus encoding ASIC1a (ACCN1) is associated with ischemic diseases using human population statistical genetics. While fewer than 10% of new molecular entities that pass through clinical trials are approved for therapeutic use, evidence of human genetic association between the gene target and traits sufficiently similar to the indication being treated increases the likelihood of approval to as high as 50%. The inventors utilized summary data from genome-wide association studies (GWAS) and calculated the statistical significance (using fastBAT) of genetic variants encompassing the ACCN1 locus with human cardiac and cerebral ischemic phenotypes. These data revealed a significant association between genetic variation in ACCN1 and major coronary heart disease and MI (P<0.05) (Table 2). The inventors also found that genetic variation in ACCN1 associates with small-vessel ischemic stroke (p=3.94×10-3), but not other stroke subtypes (Table 2). Taken together, these data provide evidence that ACCN1 polymorphisms within the human population are associated with ischemic diseases of the heart and brain.

TABLE 2

Association of polymorphisms in ACCN1 with ischemic conditions. ACCN1 gene position: chromosome 12, start: 50451419, end: 50477405)

| Genotype | No. of SNPs | SNP start | SNP end | $\chi^2$ statistic | Mean p-value |
| --- | --- | --- | --- | --- | --- |
| Acute myocardial infarction [1] | 75 | rs11377593 | rs2242507 | 152.45 | 1.4E−02 |
| Major coronary heart disease excluding revascularizations [1] | 75 | rs11377593 | rs2242507 | 199.11 | 1.8E−03 |
| Myocardial infarction [1] | 75 | rs11377593 | rs2242507 | 186.59 | 3.1E−03 |
| Any stroke [2] | 61 | rs78972052 | rs2242507 | 81.81 | 1.5E−01 |
| Any ischemic stroke [2] | 62 | rs78972052 | rs2242507 | 77.28 | 2.0E−01 |
| Large artery stroke [2] | 63 | rs78972052 | rs2242507 | 67.30 | 3.5E−01 |
| Cardioembolic stroke [2] | 61 | rs78972052 | rs2242507 | 71.63 | 2.5E−01 |
| Small vessel stroke [2] | 64 | rs78972052 | rs2242507 | 147.48 | 3.9E−03 |

The number of SNPs inside the ACCN1 locus was used to calculate the $\chi 2$ statistic and p-value. Source data: GWAS results from [1] UK Biobank from Neale Lab (The UK Biobank, http://www.nealelab.is/uk-biobank, 2018)) or [2] Malik et al. (R. Malik et al., Nat Genet 50, 524-537 (2018)).

Example 5. ASIC1a Inhibition Prevents Cell Death in In Vitro Human Models of IRI To examine whether pharmacological blockade of ASIC1a might provide therapeutic benefit in the context of human tissue, the inventors used human induced pluripotent stem cell-derived cardiomyocytes (hiPSC-CMs). Contractile cardiomyocytes were generated from stem cells using a standard monolayer-based differentiation protocol involving bi-phasic Wnt regulation (FIG. 6A and FIG. 7C). Analysis of mRNA transcripts from single-cell RNA sequencing data over a time course of cardiac differentiation from pluripotency revealed that ASIC1, ASIC3, and ASIC4 expression increased starting in day-5 cardiac progenitor populations and peaked in day-15 definitive cardiomyocytes. ASIC1 was the most highly expressed ASIC subtype, with expression levels comparable to other cardiac ion channels, such as TRPV1 and NaV1.5 (FIG. 6 B-C).

Since ASIC1a mediates influx of calcium in addition to sodium, the inventors performed calcium imaging after acute addition of Hi1a and PcTx1 to assess whether ASIC1a inhibition alters physiological electromechanical coupling in cardiomyocytes. Replated hiPSC-CMs were loaded with a fluorescent calcium dye and calcium transients were recorded before and after peptide addition. Neither Hi1a nor PcTx1 altered calcium amplitudes or spontaneous beating rate at any evaluated concentration (FIG. 6D). To further demonstrate safety of ASIC1a blockade, the inventors performed industry-standard patch-clamp electrophysiology analysis to examine the effect of Hi1a on the major off-target cardiac ion channels (Table 3). At 1 μM concentration, Hi1a had no major impact on hNaV1.5, hKV4.3/hKChIP2, hCaV1.2, hKV11.1/hERG, hKV7.1/hKCNQ1, or hKir2.1 currents.

TABLE 34

Eurofins data of patch clamp electrophysiology results for off target inhibition of cardiac ion channel currents hNav1.5

| Compound ID | Client Compound ID | Batch Number | Concentration (µM) | % inhibition n1 | n2 | n3 | mean |
|---|---|---|---|---|---|---|---|
| US034-0009110-1 | Hi1a WT | | 1 | 7.31 | 10.96 | 7.10 | 8.46 |
| Time-Matched Vehicle Control | DMSO | | 0.003 | 5.81 | 3.48 | | 4.65 |
| Time-Matched Vehicle Control | DMSO | | 0.003 | 5.88 | 8.34 | | 7.11 |
| Time-Matched Vehicle Control | DMSO | | 0.003 | 6.00 | 13.39 | | 9.70 |
| Time-Matched Vehicle Control | DMSO | | 0.003 | 6.94 | 16.38 | | 11.66 |
| Time-Matched Vehicle Control | DMSO | | 0.003 | 14.55 | 20.06 | | 17.31 |
| Positive Reference Control | Tetracaine | | 0.03 | 6.26 | 6.62 | | 6.44 |
| Positive Reference Control | Tetracaine | | 0.3 | 28.83 | 25.58 | | 27.20 |
| Positive Reference Control | Tetracaine | | 3 | 74.19 | 68.47 | | 71.33 |
| Positive Reference Control | Tetracaine | | 30 | 93.85 | 88.76 | | 91.30 |
| Positive Reference Control | Tetracaine | | 300 | 96.60 | 95.17 | | 95.88 | hKv4.3/hKChIP2

| Compound ID | Client Compound ID | Measurement | Concentration (µM) | % inhibition n1 | n2 | n3 | mean |
|---|---|---|---|---|---|---|---|
| US034-0009110-1 | Hi1a WT | Peak | 1 | 7.01 | 10.29 | 2.15 | 6.48 |
| Time-Matched Vehicle Control | DMSO | Peak | 0.003 | 9.52 | 10.19 | | 9.85 |
| Time-Matched Vehicle Control | DMSO | Peak | 0.003 | 9.44 | 10.74 | | 10.09 |
| Time-Matched Vehicle Control | DMSO | Peak | 0.003 | 10.53 | 11.25 | | 10.89 |
| Time-Matched Vehicle Control | DMSO | Peak | 0.003 | 11.69 | 13.62 | | 12.66 |
| Time-Matched Vehicle Control | DMSO | Peak | 0.003 | 12.91 | 14.91 | | 13.91 |
| Positive Reference Control | Flecainide | Peak | 0.03 | 7.41 | 10.98 | | 9.20 |
| Positive Reference Control | Flecainide | Peak | 0.3 | 4.05 | 12.76 | | 8.40 |
| Positive Reference Contml | Flecainide | Peak | 3 | 10.63 | 14.48 | | 12.55 |
| Positive Reference Control | Flecainide | Peak | 30 | 57.45 | 53.03 | | 55.24 |
| Positive Reference Control | Flecainide | Peak | 300 | 97.40 | 97.33 | | 97.37 |
| US034-0009110-1 | Hi1a WT | End | 1 | 6.42 | 9.65 | -2.27 | 4.60 |
| Time-Matched Vehicle Control | DMSO | End | 0.003 | 8.79 | 9.35 | | 9.07 |
| Time-Matched Vehicle Control | DMSO | End | 0.003 | 7.83 | 11.49 | | 9.66 |
| Time-Matched Vehicle Control | DMSO | End | 0.003 | 13.16 | 15.82 | | 14.49 |
| Time-Matched Vehicle Control | DMSO | End | 0.003 | 8.79 | 18.01 | | 13.40 |
| Time-Matched Vehicle Control | DMSO | End | 0.003 | 10.10 | 19.62 | | 14.86 |
| Positive Reference Control | Flecainide | End | 0.03 | 5.29 | 8.57 | | 6.93 |
| Positive Reference Control | Flecainide | End | 0.3 | 2.84 | 11.49 | | 7.17 |
| Positive Reference Contml | Flecainide | End | 3 | 25.60 | 27.93 | | 26.76 |
| Positive Reference Control | Flecainide | End | 30 | 69.25 | 74.44 | | 71.84 |
| Positive Reference Control | Flecainide | End | 300 | 90.01 | 90.99 | | 90.50 | hCav1.2

| Compound ID | Client Compound ID | Batch Number | Concentration (µM) | % inhibition n1 | n2 | n3 | mean |
|---|---|---|---|---|---|---|---|
| US034-0009110-1 | Hi1a WT | | 1 | 2.79 | 13.20 | 10.94 | 8.98 |
| Time-Matched Vehicle Control | DMSO | | 0.003 | 4.58 | 6.34 | | 5.46 |
| Time-Matched Vehicle Control | DMSO | | 0.003 | 16.52 | 18.39 | | 17.45 |
| Time-Matched Vehicle Control | DMSO | | 0.003 | 18.02 | 21.14 | | 19.58 |
| Positive Reference Control | Nifedipine | | 0.001 | 21.65 | 8.54 | | 15.09 |
| Positive Reference Control | Nifedipine | | 0.01 | 38.19 | 31.48 | | 34.83 |
| Positive Reference Control | Nifedipine | | 0.1 | 53.13 | 58.25 | | 55.69 |
| Positive Reference Control | Nifedipine | | 1 | 56.76 | 65.20 | | 60.98 |
| Positive Reference Control | Nifedipine | | 10 | 81.42 | 86.13 | | 83.78 |
| Positive Reference Control | Nifedipine | | 100 | 95.15 | 94.45 | | 94.80 | hNav1.5 Late current antagonist assay

| Compound ID | Client Compound ID | Batch Number | Concentration (µM) | % inhibition n1 | n2 | n3 | mean |
|---|---|---|---|---|---|---|---|
| US034-0009110-1 | Hi1a WT | | 1 | -9.74 | -13.93 | -13.45 | -12.37 |
| Time-Matched Vehicle Control | ATXII | | 0.1 | 12.22 | 12.95 | | 12.59 |
| Time-Matched Vehicle Control | ATXII | | 0.1 | 12.69 | 11.67 | | 12.18 |
| Time-Matched Vehicle Control | ATXII | | 0.1 | 12.21 | -1.06 | | 5.57 |
| Positive Reference Control | Ranolazin | | 1 | 6.36 | 5.73 | | 6.04 |
| Positive Reference Contml | Ranolazine | | 3 | 18.25 | 20.77 | | 19.51 |
| Positive Reference Control | Ranolazine | | 10 | 39.00 | 33.34 | | 36.17 |

TABLE 34-continued

Eurofins data of patch clamp electrophysiology results for off target inhibition of cardiac ion channel currents

| | | | | | |
|---|---|---|---|---|---|
| Positive Reference Control | Ranolazine | | 30 | 53.79 | 54.57 | 54.18 |
| Positive Reference Control | Ranolazine | | 100 | 80.54 | 81.39 | 80.97 |
| Positive Reference Control | Ranolazine | | 300 | 95.69 | 95.31 | 95.50 | hERG

| Compound ID | Client Compound ID | Batch Number | Concentration (µM) | % inhibition n1 | n2 | n3 | mean |
|---|---|---|---|---|---|---|---|
| US034-0009110-1 | Hi1a WT | | 1 | −7.50 | 1.58 | −12.68 | −6.20 |
| Time-Matched Vehicle Control | DMSO | | 0.003 | −8.30 | 0.64 | | −3.83 |
| Time-Matched Vehicle Control | DMSO | | 0.003 | −8.37 | 2.77 | | −2.80 |
| Time-Matched Vehicle Control | DMSO | | 0.003 | −6.85 | 5.17 | | −0.84 |
| Time-Matched Vehicle Control | DMSO | | 0.003 | −5.18 | 6.60 | | 0.71 |
| Time-Matched Vehicle Control | DMSO | | 0.003 | −1.07 | 10.86 | | 4.90 |
| Positive Reference Control | E-4031 | | 0.003 | 5.98 | 1.55 | | 3.77 |
| Positive Reference Control | E-4031 | | 0.01 | 22.13 | 17.61 | | 19.87 |
| Positive Reference Control | E-4031 | | 0.03 | 50.00 | 38.10 | | 44.05 |
| Positive Reference Control | E-4031 | | 0.1 | 90.16 | 79.29 | | 84.72 |
| Positive Reference Control | E-4031 | | 0.3 | 98.67 | 93.69 | | 96.18 | hKCNQ1 /mink

| Compound ID | Client Compound ID | Batch Number | Concentration (µM) | % inhibition n1 | n2 | n3 | mean |
|---|---|---|---|---|---|---|---|
| US034-0009110-1 | Hi1a WT | | 1 | 1.87 | −0.67 | −0.68 | 0.17 |
| Time-Matched Vehicle Control | DMSO | | 0.003 | 4.27 | 1.17 | | 2.72 |
| Time-Matched Vehicle Control | DMSO | | 0.003 | −1.91 | 5.71 | | 1.90 |
| Time-Matched Vehicle Control | DMSO | | 0.003 | −1.47 | 12.48 | | 5.51 |
| Positive Reference Control | Chromanol 293B | | 0.3 | 1.35 | 7.13 | | 4.24 |
| Positive Reference Control | Chromanol 293B | | 1 | 9.45 | 15.04 | | 12.25 |
| Positive Reference Control | Chromanol 293B | | 3 | 21.34 | 24.36 | | 22.85 |
| Positive Reference Control | Chromanol 293B | | 10 | 39.37 | 41.20 | | 40.28 |
| Positive Reference Control | Chromanol 293B | | 30 | 74.46 | 73.39 | | 73.92 |
| Positive Reference Control | Chromanol 293B | | 100 | 96.45 | 95.16 | | 95.80 | hKir2.1

| Compound ID | Client Compound ID | Measurement | Concentration (µM) | % inhibition n1 | n2 | n3 | mean |
|---|---|---|---|---|---|---|---|
| US034-0009110-1 | Hi1a WT | Peak | 1 | 1.94 | −0.02 | −0.97 | 0.31 |
| Time-Matched Vehicle Control | DMSO | Peak | 0.003 | −5.63 | 0.05 | — | −2.79 |
| Time-Matched Vehicle Control | DMSO | Peak | 0.003 | −4.98 | 1.50 | — | −1.74 |
| Time-Matched Vehicle Control | DMSO | Peak | 0.003 | −3.13 | 6.70 | — | 1.78 |
| Positive Reference Control | Barium | Peak | 0.3 | 1.78 | 2.96 | — | 2.37 |
| Positive Reference Control | Barium | Peak | 1 | 7.99 | 4.90 | — | 6.45 |
| Positive Reference Control | Barium | Peak | 3 | 14.88 | 10.25 | — | 12.57 |
| Positive Reference Control | Barium | Peak | 10 | 16.68 | 9.94 | — | 13.31 |
| Positive Reference Control | Barium | Peak | 30 | 38.78 | 25.19 | — | 31.99 |
| Positive Reference Control | Barium | Peak | 100 | 63.60 | 61.68 | — | 62.64 |
| US034-0009110-1 | Hi1a WT | End | 1 | 1.81 | −0.51 | −3.14 | −0.62 |
| Time-Matched Vehicle Control | DMSO | End | 0.003 | −5.71 | −0.06 | — | −2.89 |
| Time-Matched Vehicle Control | DMSO | End | 0.003 | −6.61 | 1.59 | — | −2.51 |
| Time-Matched Vehicle Control | DMSO | End | 0.003 | −6.64 | 8.78 | — | 1.07 |
| Positive Reference Control | Barium | End | 0.3 | 6.49 | 7.53 | — | 7.01 |
| Positive Reference Control | Barium | End | 1 | 19.93 | 16.65 | — | 18.29 |
| Positive Reference Control | Barium | End | 3 | 39.87 | 42.88 | — | 41.38 |
| Positive Reference Control | Barium | End | 10 | 79.79 | 81.66 | — | 80.72 |
| Positive Reference Control | Barium | End | 30 | 93.64 | 92.93 | — | 93.28 |
| Positive Reference Control | Barium | End | 100 | 98.46 | 98.47 | — | 98.46 |

Cardiac CiPA Reference Compound Panel

| ITEM | Assay Name | Mode | Reference Compound | Estimated $IC_{50}$ (µM) |
|---|---|---|---|---|
| CYL8004QP2DR | Nav1.5 Human Sodium Ion Channel Cell Based QPatch CiPA Assay | Antagonist | Tetracaine | 0.94 |
| CYL8038QP2DR | hERG Human Potassium Ion Channel Cell Based QPatch CiPA Assay | Antagonist | E-4031 | 0.032 |
| CYL8007QP2DR | KCNQ1/minK Human Potassium Ion Channel Cell Based QPatch | Antagonist | Chromanol 293B | 11.5 |

TABLE 34-continued

Eurofins data of patch clamp electrophysiology results for off target inhibition of cardiac ion channel currents

| | | | | |
|---|---|---|---|---|
| CYL8032QP2DR | Kir2.1 Human Potassium Ion Channel Cell Based QPatch CiPA Assay | Antagonist | Barium Chloride | 62.3 (Peak) & 3.6 (End) |
| CYL8069QP2DR | Kv4.3 /KChIP2 Human Potassium Ion Channel Cell Based QPatch CiPA Assay | Antagonist | Flecainide | 22.5 (Peak) & 10.0 (End) |
| CYL8051QP2DR | Cav1.2 (L-type) Human Calcium Ion Channel Cell Based QPatch CiPA Assay | Antagonist | Nifedipine | 0.090 |
| CYL7004QP2DR | Nav1.5 Late Current Human Ion Channel Cell Based Antagonist QPatch CiPA Assay | Antagonist | Ranolazine | 20.1 |

Lastly, the inventors showed that exposure of hiPSC-CMs to Hi1a for 48 h led to no significant alteration in cell viability compared to controls (FIG. 7D).

To assess whether ASIC1a inhibition is cardioprotective in hiPSC-CMs, the inventors evaluated cell death in response to in vitro acidosis, induced by culturing hiPSC-CMs in Hank's buffered sodium salt (HBSS) with pH adjusted to pH 7.4, 6.0, or 5.0. The requirement to expose cells to severe acidosis is consistent with previous studies showing reduced pH sensitivity in immature iPSC-derived cardiomyocytes and is consistent with testing acid-sensitive ion channels in vitro. ASIC1 mRNA expression was not significantly altered by low pH treatment, but significant cell death (>40%), as assessed by LDH secretion, was observed in cultures treated overnight at pH 5.0, with minimal cell death occurring at pH 7.4 or pH 6.0 (FIG. 7 E-F). Treatment with either Hi1a or PcTx1 resulted in nearly complete cardioprotection, even at concentrations as low as 1 nM (FIG. 4E and FIG. 7 G-H). To further confirm that ASIC1a plays a direct role in mediating cell death, the inventors treated hiPSC-CMs overnight with 20 nM MitTx, a potent agonist of ASIC1a from snake venom. Consistent with ASIC1a mediating the injury response to cardiac ischemia, treatment of hiPSC-CMs with MitTx resulted in increased cell death at both pH 7.4 and pH 6.0 (FIG. 4F). The inventors next evaluated the cardioprotective effect of Hi1a and PcTx1 in an in vitro model of ischemia/acidosis with reperfusion. To mimic ischemia/acidosis in vitro, hiPSC-CMs were incubated overnight in combined hypoxic (0.5% O2) and acidic (pH 5.0) conditions with or without peptide. After 18 h of incubation, the low-pH medium was replaced with medium at physiological pH 7.4 with or without peptide, and the cells were incubated for an additional hour under normoxic conditions. Significant cell death was observed in control hiPSC-CMs, but this was blocked by either 10 nM Hi1a or PcTx1 (FIG. 6 G-H). These data suggest that ASIC1a mediates cell death responses in human cardiomyocytes and that pharmacological inhibition of ASIC1a confers significant protection against ischemia-induced cell stress.

Example 6. Hypoxia-Reoxygenation Injury Prevention in ASIC1a KO hiPSC-Derived Cardiomyocytes

Materials and Methods

Asic1a CRIPSR KO WTC hiPSC lines: Asic1a CRIPSR KO WTC hiPSC lines were generated at Queensland Facility for Advanced Genome Editing (QFAGE), The University of Queensland. In brief, three guide RNA (sgRNA) targeting the first coding exon of human Asic1a with specificity score higher than 80 (Hsu et al. Nat Biotech 2013) were designed as follows: gRNA1 (protospacer sequence: CCGCTCGTAGGAGAAGATGT) (SEQ ID No. 8), gRNA2 (protospacer sequence: CCATGTCACCAAGCTCGACG) (SEQ ID No. 9) and gRNA3 (protospacer sequence: GGCTAAAGCGGAACTCGTTG) (SEQ ID No. 10).

For CRISPR cell engineering, 10 pmol each of gRNAs (synthetic crRNA:tracrRNA duplex, IDT) were mixed with equal amount of spCas9 protein (IDT) and incubated at room temperature for 10 min to assemble into ribonucleoprotein (RNP) complex. hiPSC cells were treated with Rock inhibitor (1:1000) for one hour prior to transfection. Cultures were washed once with PBS and incubated with 1×TrypLE™ (Thermofisher) for 3 min at 37° C. to be dissociated into single cell suspension. For each transfection, assembled RNPs were delivered into 100K iPSCs by electroporation (Thermofisher Neon) using the following protocol: 1300V/30 ms/1 pulse. Transfected cells were seeded into 12 well plate and further expanded for 4~5 days for backup and 100 k cells were collected for genomic DNA extraction and CRISPR analysis. The following primers have been used for PCR amplification of the target region:

```
Forward:
                                   (SEQ ID No. 11)
CCTCAACCTCGGATGACTATATCTG;

Reverse:
                                   (SEQ ID No. 12)
CGAGCTGTTCTGGACTATGCTG.
```

Editing efficiency was analysed by genomic PCR, T7E1 (T7 Endonuclease I) assay and ICE analysis (Hsiau et al. BioRxiv, 2019). Above 90% editing efficiency was achieved by co-delivery two or three gRNA into hiPSCs.

hiPSC maintenance and cardiomyocyte differentiation: Undifferentiated hiPSCs were maintained on Vitronectin XF (5 μg/mL, Stem Cell Technologies) coated tissue culture dishes as per manufacturer recommendation with mTeSR™ PLUS medium with supplementation (Stem Cell Technologies). Contractile cardiomyocytes were differentiated using a high-density monolayer format (3). hiPSCs were dissociated with 0.5 mM EDTA solution supplemented with 1.1 mM D-glucose. Single-cell suspensions were plated at a density of $1.8 \times 10^5$ cells/cm$^2$ and cultured overnight in mTeSR™ medium supplemented with 10 μM Y-27632 dihydrochloride (Stem Cell Technologies). The following day, when the monolayer reached approximately 90-95% confluence, the cells were washed with PBS and media changed to RPMI (ThermoFisher) containing 3 μM CHIR99021 (Stem Cell Technologies), 500 μg/mL BSA (Sigma Aldrich), and 213 μg/mL ascorbic acid (Sigma Aldrich). After 3 days of culture, the medium was exchanged to RPMI containing 500 μg/mL BSA, 213 μg/mL ascorbic acid, and 5 μM Xav-939 (Stem Cell Technologies). On day 5, the medium was replaced with RPMI containing BSA and ascorbic acid as on day 3. Starting on day 7, the cells were fed every other day with RPMI containing 1×B27™ supplement with insulin (Life Technologies). Spontaneous beating was typically observed after 7 or 9 days of differentiation.

Flow cytometry analysis of cardiomyocyte purity: day 15 cell populations were fixed with 4% paraformaldehyde (Sigma Aldrich), permeabilized in 0.75% saponin (Sigma Aldrich), and labelled with Phycoerythrin (PE)-conjugated sarcomeric α-actinin (SA) antibody (Miltenyi Biotec Australia Pty) or PE-conjugated mouse isotype (IgG) control (Miltenyi Biotec Australia Pty). Stained samples were analysed on a FACS CANTO II (Becton Dickinson) machine with FACSDiva software (BD Biosciences). Data were analysed was using FlowJo software and cardiac populations were determined with population gating from isotype controls.

qRT-PCR analysis of ASIC1a mRNA transcript levels: total RNA was extracted from day 5, day 7, and day 15 cell populations using a RNeasy® Mini Kit (QIAGEN). SuperScript™ III First Strand Synthesis (ThermoFisher) was used to generate cDNA and qRT-PCR was performed on ViiA 7 Real-Time PCR Machine (Applied Biosystems) with SYBR® Green PCR Master Mix (ThermoFisher). Transcript copy numbers were calculated using 2-ΔΔCt method with normalization to HPRT1 housekeeping gene. The following primer sequences were used:

```
ASIC1α:
forward
                                     (SEQ ID No. 13)
5'-CCGCTTTAGCCAAGTCTCCA-3'
and reverse
                                     (SEQ ID No. 14)
5'-CTGCCATCTGTGTGTCTGGT-3';
HPRT1:
forward
                                     (SEQ ID No. 15)
5'-TGACACTGGCAAAACAATGCA-3'
and reverse
                                     (SEQ ID No. 16)
5'-GGTCCTTTTCACCAGCAAGCT-3'.
```

Hypoxia-reoxygenation injury model. ASIC1a KO hiPSC-derived cardiomyocytes were replated on day 15 of differentiation for in vitro hypoxia-reoxygenation experiments. Briefly, cardiomyocyte monolayers were washed with PBS, enzymatically digested with 0.5% Trypsin for 7 minutes at 37° C., and collected in 50% FBS in RPMI to stop the reaction. The cell suspension was passed through a 100 μm cell strainer to obtain single cells and centrifuged at 1000 RPM for 5 minutes. Cardiomyocytes were replated at a density of $6.3 \times 10^4$ cells/cm$^2$ in 96 well plate (20,000 per well) in RPMI containing 1×B27™ supplement with insulin (Life Technologies), 5% FBS, and 10 μM Y-27632 dihydrochloride (Stem Cell Technologies). After re-plating, the cells were maintained for an additional 7 days with the medium changed to RPMI+B27™ the day after replating and every other day afterwards. To prepare media for the ischemia/acidosis injury, 10×HBSS without sodium bicarbonate (Sigma) was diluted to 1× concentration in sterile tissue culture-grade water. Solutions were buffered with either 12 mM HEPES (for pH 7.4 media, Sigma Aldrich) or 12 mM MES (for pH<6.5, Sigma Aldrich) and the pH adjusted accordingly with 1 M NaOH. The medium was sterile filtered with 0.22 μm syringe filters (Millipore). The replated cardiomyocytes were treated overnight (18 h) in HBSS pH 6.0 or HBSS pH 5.0 under hypoxic (0.5% $O_2$; 5% $CO_2$) culture conditions. After 18 h hypoxia, the medium was replaced with HBSS pH 7.4 and cultured for 4 h under normoxic conditions (~18.5% $O_2$; 5% $CO_2$). To assess cell death throughout the injury, 50 μL supernatant was collected from each well at the end of hypoxia and at 1 and 4 h of reperfusion. Supernatant lactate dehydrogenase (LDH) levels were measured using a cytotoxicity detection kit (Roche). Percent cell death was calculated using low and high controls. For low control (LC), cardiomyocytes were cultured overnight in standard culture media (RPMI+B27™) under normoxic conditions. For high control (HC), cells were cultured overnight in RPMI+B27™ containing 1% Triton™ X-100 (Sigma-Aldrich).

Results

Following cardiomyocyte differentiation protocol, populations derived from ASIC1a KO hiPSCs showed similar levels of cardiac purity compared to WTC wildtype controls with approximately 80-85% sarcomeric α-actinin-positive cardiomyocytes (FIG. 8). To assess whether genetic ablation of ASIC1a prevents cell death during in vitro ischemia-reperfusion injury (IRI), the inventors cultured ASIC1a KO and WTC wildtype hiPSC-derived cardiomyocytes overnight in combined hypoxic (0.5% $O_2$) and acidic (pH 6.0 or pH 5.0) conditions. After 18 h, the low-pH medium was replaced with medium at physiological pH 7.4 and the cells were incubated for an additional 4 hours under normoxic conditions. Significant cell death was observed in WTC wildtype cardiomyocytes throughout the injury timecourse, while ASIC1a KO cardiomyocyte populations showed reduced level of cell death at all timepoints (FIG. 8B-C). These findings are consistent with our prior results demonstrating that peptide inhibitors of ASIC1a confer significant cardioprotection, and further confirms that ASIC1a mediates cell death responses in human cardiomyocytes.

The invention claimed is:

1. A method of producing a transplant composition comprising cardiomyocytes having a ASIC1a−/− phenotype, the method comprising the steps of:
   a) genetically modifying stem cells to have a ASIC1a−/− phenotype;
   b) differentiating said stem cells having a ASIC1a−/− phenotype to cardiomyocytes, wherein the differentiation is performed in vitro; and
   c) admixing said cardiomyocytes with a pharmaceutically acceptable carrier.

2. The method of claim 1, wherein in step a) the stem cells are human induced pluripotent stem cells (iPSCs).

3. The method of claim 1, wherein in step a) the stem cells are from a healthy subject.

4. The method of claim 1, wherein in step a) the stem cells are from a subject in need of a treatment comprising the administration of the transplant composition.

5. The method of claim 1, further comprising adding an agent after step c), wherein the agent promotes the survival of the cardiomyocytes.

6. The method of claim 5, wherein the agent is an apoptosis inhibitor, or a necrosis inhibitor.

* * * * *